United States Patent
Cui et al.

(10) Patent No.: US 11,819,022 B2
(45) Date of Patent: Nov. 21, 2023

(54) STACKED HERBICIDE TOLERANCE EVENT 8264.44.06.1, RELATED TRANSGENIC SOYBEAN LINES, AND DETECTION THEREOF

(71) Applicants: Dow AgroSciences LLC, Indianapolis, IN (US); M.S. Technologies, L.L.C., West Point, IA (US)

(72) Inventors: Yunxing C. Cui, Carmel, IN (US); Thomas Hoffman, Zionsville, IN (US); Ning Zhou, Zionsville, IN (US); Stephen N. Novak, Westfield, IN (US); Julissa Colon, Cidra, PR (US); Dawn M. Parkhurst, Avon, IN (US); Sandra G. Toledo, West Lafayette, IN (US); Terry R. Wright, Westfield, IN (US); Sean M. Russell, Carmel, IN (US); Bruce Held, Ames, IA (US); Vaithilingam Sekar, Ames, IA (US)

(73) Assignees: Dow AgroSciences LLC, Indianapolis, IN (US); M.S. Technologies, L.L.C., West Point, IA (US)

( * ) Notice: Subject to any disclaimer, the term of this patent is extended or adjusted under 35 U.S.C. 154(b) by 0 days.

(21) Appl. No.: 17/897,988

(22) Filed: Aug. 29, 2022

(65) Prior Publication Data
US 2023/0143169 A1    May 11, 2023

Related U.S. Application Data

(60) Division of application No. 17/224,694, filed on Apr. 7, 2021, now Pat. No. 11,425,906, which is a division of application No. 16/434,995, filed on Jun. 7, 2019, now Pat. No. 10,973,229, which is a division of application No. 15/399,674, filed on Jan. 5, 2017, now Pat. No. 10,400,250, which is a continuation of application No. 13/991,246, filed as application No. PCT/US2011/063129 on Dec. 2, 2011, now Pat. No. 9,540,655.

(60) Provisional application No. 61/511,664, filed on Jul. 26, 2011, provisional application No. 61/471,845, filed on Apr. 5, 2011, provisional application No. 61/521,798, filed on Aug. 10, 2011, provisional application No. 61/419,706, filed on Dec. 3, 2010.

(51) Int. Cl.
| | | |
|---|---|---|
| C12N 15/82 | (2006.01) | |
| A01N 39/04 | (2006.01) | |
| C12N 9/10 | (2006.01) | |
| C12Q 1/6895 | (2018.01) | |
| C12N 9/00 | (2006.01) | |

(52) U.S. Cl.
CPC ........... *A01N 39/04* (2013.01); *C12N 9/1092* (2013.01); *C12N 9/93* (2013.01); *C12N 15/8241* (2013.01); *C12N 15/8274* (2013.01); *C12N 15/8275* (2013.01); *C12Q 1/6895* (2013.01); *C12Y 205/01019* (2013.01); *C12Y 604/01002* (2013.01); *C12Q 2600/13* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 7,626,077 B2 | 12/2009 | Held et al. | |
| 7,695,914 B2 | 4/2010 | Bing et al. | |
| 7,696,341 B2 | 4/2010 | Bing et al. | |
| 7,723,575 B2 | 5/2010 | Alibhai et al. | |
| 7,750,207 B2 | 7/2010 | Wu et al. | |
| 7,786,353 B2 | 8/2010 | Fernandes | |
| 7,807,791 B2 | 10/2010 | Sekar et al. | |

(Continued)

FOREIGN PATENT DOCUMENTS

| | | |
|---|---|---|
| CN | 1561167 | 1/2005 |
| CN | 1561168 | 1/2005 |

(Continued)

OTHER PUBLICATIONS

"Glycine max chromosome 15, whole genome shotgun sequence" [Jan. 11, 2010, online] retrieved from GenBank [retrieved on Jun. 23, 2016], accession No. CM000848 http://www.ncbi.nlm.nih.gov/nuccore/283570559?sat=16&satkey=5691280.

(Continued)

*Primary Examiner* — Weihua Fan
(74) *Attorney, Agent, or Firm* — Barnes & Thornburg LLP

(57) ABSTRACT

This invention relates in part to soybean event pDAB8264.44.06.1 and includes a novel expression cassettes and transgenic inserts comprising multiple traits conferring resistance to glyphosate, aryloxyalkanoate, and glufosinate herbicides. This invention also relates in part to methods of controlling resistant weeds, plant breeding and herbicide tolerant plants. In some embodiments, the event sequence can be "stacked" with other traits, including, for example, other herbicide tolerance gene(s) and/or insect-inhibitory proteins. This invention further relates in part to endpoint TaqMan PCR assays for the detection of Event pDAB8264.44.06.1 in soybeans and related plant material. Some embodiments can perform high throughput zygosity analysis of plant material and other embodiments can be used to uniquely identify the zygosity of and breed soybean lines comprising the event of the subject invention. Kits and conditions useful in conducting these assays are also provided.

3 Claims, 3 Drawing Sheets
Specification includes a Sequence Listing.

(56) References Cited

U.S. PATENT DOCUMENTS

| | | | |
|---|---|---|---|
| 7,834,146 | B2 | 11/2010 | Kovalic et al. |
| 7,883,850 | B2 | 2/2011 | Song et al. |
| 8,916,752 | B2 | 12/2014 | Wright et al. |
| 9,540,655 | B2 | 1/2017 | Cui et al. |
| 10,400,250 | B2 | 9/2019 | Cui et al. |
| 2002/0013958 | A1 | 1/2002 | Lalgudi et al. |
| 2004/0031072 | A1 | 2/2004 | La Rosa et al. |
| 2005/0216969 | A1 | 9/2005 | Song et al. |
| 2006/0282915 | A1 | 12/2006 | Malven et al. |
| 2007/0083945 | A1 | 4/2007 | Byrum et al. |
| 2007/0143873 | A1 | 6/2007 | Pratelli et al. |
| 2007/0143876 | A1 | 6/2007 | Song et al. |
| 2008/0051288 | A1 | 2/2008 | Cressman et al. |
| 2008/0312082 | A1 | 12/2008 | Kinney |
| 2009/0093366 | A1 | 4/2009 | Wright et al. |
| 2009/0104700 | A1 | 4/2009 | Samuel et al. |
| 2010/0197503 | A1 | 8/2010 | Hawkes et al. |
| 2010/0251432 | A1 | 9/2010 | Lira et al. |
| 2013/0055453 | A1 | 2/2013 | Hoffman et al. |
| 2015/0080218 | A1 | 3/2015 | Wright et al. |

FOREIGN PATENT DOCUMENTS

| | | | |
|---|---|---|---|
| CN | 101020905 | | 8/2007 |
| CN | 101861392 | | 10/2010 |
| EP | 2309843 | | 4/2011 |
| JP | A-2004-27091 | | 1/2004 |
| JP | A-2008-295322 | | 12/2008 |
| RU | 2337531 | | 11/2008 |
| UA | 200714839 | | 4/2008 |
| WO | 2003/014357 | | 2/2003 |
| WO | WO 2004/011601 | | 2/2004 |
| WO | WO 2004/074443 | | 9/2004 |
| WO | WO 2006/045633 | | 5/2006 |
| WO | WO2006/108675 | A2 | 1/2007 |
| WO | WO2007/053482 | A2 | 5/2007 |
| WO | WO-2007053482 | A2 * | 5/2007 ............ A01N 37/10 |
| WO | WO 2006/130436 | | 12/2007 |
| WO | WO 2008/141154 | | 11/2008 |
| WO | WO 2009/037329 | | 3/2009 |
| WO | 2009/064652 | | 5/2009 |
| WO | WO 2009/152359 | | 12/2009 |
| WO | WO 2010/002984 | | 1/2010 |
| WO | WO 2010/008760 | | 1/2010 |
| WO | WO 2010/015627 | | 2/2010 |
| WO | WO 2010/079032 | | 7/2010 |
| WO | WO 2011/063413 | | 5/2011 |
| WO | WO-2011063413 | A2 * | 5/2011 ............... A01H 5/00 |
| WO | WO 2011/066360 | | 6/2011 |
| WO | WO 2011/066382 | | 6/2011 |
| WO | WO 2011/066384 | | 6/2011 |
| WO | WO 2012/075426 | | 6/2012 |

OTHER PUBLICATIONS

EMBL Accession No. HN002532, GSS_Ba205J12.R GSS_Ba Glycine soja genomic 3', genomic survey sequence, May 9, 2010.
XP-002732015, AAD-12, 2mepsps, pat. Glycine max (L.) Merr. (DAS44406 OECD UI DAS-44406-6 AFFRC Feb. 7, 2011.
Lam, Hon-Ming, et al. "Resequencing of 31 wild and cultivated soybean genomes identifies patterns of genetic diversity and selection," 2010, Nature genetics 42,1053-1059.
Schmutz, J., et al. "Genome sequence of the palaeopolyploid soybean," 2010, Nature, 463, 178-183.
Zhong, Gan-Yuan, "Genetic issues and pitfalls in transgenic plant breeding," 2001, Euphytica 118, 137-144.
Database Geneseq [Online] Jul. 24, 2008 (Jul. 24, 2008), "B. napas PCR primer RflRV."
GenBank accession: HQ403648—Eleusine indica 5-enolpyruvylshikimate-3-phosphate synthase (epsps-R) mRNA, complete cds; plastid—May 27, 2011.
GenBank accession: HQ403647—Eleusine indica 5-enolpyruvylshikimate-3-phosphate synthase (EPSPS-S) mRNA, complete cds; plasmid—May 27, 2011.
GenBank accession: GU256772—Mutant Zoysia japonica 5-enolpyruvyl shikimate 3-phosphate synthase (EPSPS) mRNA, complete cds—Jan. 27, 2010.
GenBank accession: GU256771—Zoysia japonica 5-enolpyruvyl shikimate 3-phosphate synthase (EPSPS) mRNA, complete cds—Jan. 27, 2010.
http://www.bch.biodic.go.jp/download/en_lmo/H23_9_6_DAS44406. pdg-aad-12, 2mepsps, pat, Glycine max (L.) Merr. (OAS44406, OECO UI: OAS-44406-6)—Feb. 7, 2011.
GenBank accession: XM_002436379—Sorghum bicolor hypothetical protein, mRNA—Jul. 13, 2009.
GenBank accession: GX744067—Sequence 12246 from U.S. Pat. No. 7,834,146—Dec. 13, 2010.
GenBank accession: GX619320—Sequence 5 from U.S. Pat. No. 7,807,791—Dec. 13, 2010.
GenBank accession: GX315220—Sequence 9295 from U.S. Pat. No. 7,750,207—Dec. 12, 2010.
GenBank accession: GX270866—Sequence 47 from U.S. Pat. No. 7,723,575—Aug. 13, 2010.
GenBank accession: GY007493—Sequence 3 from U.S. Pat. No. 7,883,850—Apr. 30, 2011.
GenBank accession: JA216562—Sequence 39 from patent EP2309843—Apr. 26, 2011.
GenBank accession: FW377938—Transgenic plant event detection—Sep. 30, 2010.
GenBank accession: GX006377—Sequence 27 from U.S. Pat. No. 7,696,341—Aug. 13, 2010.
GenBank accession: GX006374—Sequence 24 from U.S. Pat. No. 7,696,341—Aug. 13, 2010.
GenBank accession: GX003492—Sequence 27 from U.S. Pat. No. 7,695,914—Aug. 13, 2010.
GenBank accession: GX003489—Sequence 24 from U.S. Pat. No. 7,695,914—Aug. 13, 2010.
GenBank accession: HD115809—Sequence 29 from Patent WO2010079032—Aug. 10, 2010.
GenBank accession: GQ497217—Glycine max transgenic GMO cassette genomic sequence—Sep. 28, 2009.
GenBank accession: FJ410919—Binary vector pWY109, complete sequence—Jan. 12, 2009.
GenBank accession: EU554319—Yeast selection vector pIS421, complete sequence—Sep. 23, 2008.
GenBank accession: DQ156557—Zea mays transgenic phosphinothricin acetyltransferase gene, partial cds; and beta lactamase and phosphinothricin acetyltransferase genes, complete cds—Mar. 1, 2006.
GenBank accession: AC217803—Canis familiaris chromosome 21, clone Work_Region, complete sequence—Feb. 28, 2008.
GenBank accession: AC187003—Canis Familiaris chromosome 21, clone XX-427H12, complete sequence—Jul. 29, 2006.
GenBank accession: AK157167—Mus musculus activated spleen cDNA, Riken full-length enriched library, clone: F830205P13 product: unclassifiable, full insert sequence—Oct. 16, 2010.
GenBank accession: AK081799—Mus musculus 16 days embryo head cDNA, Riken full-length enriched library, clone: C130078E19 product: unclassifiable, full insert sequence—Oct. 6, 2010.
GenBank accession: AB073156—Arabidopsis thaliana DNA, chromosome 4 centromere region, BAC clone: F13F19—Feb. 14, 2004.
GenBank accession: BT090294—Soybean clone JCVI-FLGm-4121 unknown mRNA—Aug. 6, 2009.
GenBank. Accesion AY395700—Eleusine indica 5-enolpyruvylshikimate-3-phosphate synthase (EPSPS-S) mRNA, partial cds—Oct. 29, 2006.
GenBank. Accesion AJ417034—Eleusine indica platid partial mRNA for 5-enolpyruvylshikimate-3-phosphate synthase (EPSPS-S gene)—Apr. 15, 2005.
GenBank. Accesion X63374—Z.mays mRNA for EPSP-synthase—May 18, 2005.
GenBank. Accesion AY106729—Zea mays PCO094563 mRNA sequence—Jun. 2, 2008.
GenBank. Accesion CQ868456—Sequence 3 from Patent WO2004074443—Sep. 13, 2004.

(56) References Cited

OTHER PUBLICATIONS

GenBank. Accession GP765237—Sequence 5 from U.S. Pat. No. 7,626,077—Dec. 14, 2009.
GenBank. Accession D1012786—*Chimera* gene with several herbicide resistant genes, plant cell and plant resistant to several herbicides—Feb. 21, 2008.
GenBank. Accession CS434496—Sequence 14 from Patent WO2006045633—Oct. 24, 2006.
GenBank. Accession EU090199—*Brassica napus* transgenic line Rfl right border junction sequence of transgenic event genomic sequence—Nov. 7, 2007.
GenBank. Accession GU574780—MISSA recipient vector BIBAC-LTR, complete sequence—May 6, 2010.
GenBank. Accession GN123171—Sequence 6067 from Patent WO2009037329—Apr. 24, 2009.
GenBank. Accession GN123168—Sequence 6064 from Patent WO2009037329—Apr. 24, 2009.
GenBank. Accession GN123173—Sequence 6069 from Patent WO2009037329—Apr. 24, 2009.
GenBank. Accession XM_002980455—Selaginella moellendorffii hypothetical protein, mRNA—Aug. 13, 2010.
Database Geneseq [Online] Jul. 9, 2009 (Jul. 9, 2009), «Soybean nucleic acid Seq ID No. 133298», retrieved from EBI accession No. GSN:ARD51602 Database accession No. ARD51602.
ARD51602, Database GeneSeq[online], Apr. 12, 2007/.
A59344, Database DDBJ[online], Mar. 6, 1998, A59344.1, http://getentry.ddbi.nig.ac.ip/getentry/na/A59344/?filetype=html.
A02774, Database DDBJ[online], Mar. 25, 1993, A02774.1, http://getentrv.ddbi.nig.ac.ip/getentrv/na/A02774/?filetype=html.
AAN50226, Database GeneSeq[online], Oct. 24, 2003.
AB027254, Database DDBJfonline], Jan. 24, 2004.
BC100043, Database DDBJ[online], Aug. 15, 2005.
ARU42167, Database GeneSeq1online], Aug. 21, 2008.
AQY41271, Database GeneSeq[online], Jul. 10, 2008.
Pakula, AA et al., "Genetic analysis of protein stability and function," 1989, Anna. Rev. Genet, 23, pp. 289-310. (abstract only).
Frankel, AE. et al., "Characterization of diphtheria fusion proteins targeted to the human interleukin-3 receptor," 2000, Protein Eng., vol. 13, No. 8, 575-581.
Database NCBI Reference Sequence: XM_002582376.1 from Sep. 16, 2009.
Database NCBI Reference Sequence: XM:_002980455.1 from Aug. 13, 2010 (see sequence).
https://www.jpo.go.jp/shiryou/s_sonata/hyoujun_gijutsu/kakusan/001.html.
GenBank; AK286292.1. Glycine max cDNA, clone: GMFL01-25-J19 [online] Nov. 19, 2008 [retrieved on Mar. 14, 2012]. Available on the internet: <URL:http:www.ncbi.nlm.nih.gov/nuccore/AK286292.1>. Especially p. 1.
GenBank EU721743.1. Glycine max clone BAC 71B1. [online] Dec. 5, 2008 [retrieved Mar. 14, 2012]. Available on the internet: <URL:http://www.ncbi.nlm.nih.gov/nuccore/EU721743>. Especially p. 2-4.
Database Geneseq [Online] Jul. 9, 2009 (Jul. 9, 2009), "Soybean nucleic acid SEQ ID No. 133298.", XP002721468, retrieved from EBI accession No. GSN:ARD51602.
Database Geneseq [Online] Jul. 9, 2009 (Jul. 9, 2009), "Soybean nucleic acid SEQ ID No. 33302.", XP002721469, retrieved from EBI accession No. GSN:ARC51605.
Database EMBL [Online] Oct. 28, 2006 (Oct. 28, 2006), "GM_WBa0024105.r GM_WBa Glycine max genomic clone GM_WBa0024105 3', genomic survey sequence.", XP002721470, retrieved from EBI accession No. EM_GSS:ED626487.
Database EMBL [Online] May 9, 2010 (May 9, 2010), "GSS_Ba098E14. R GSS_Ba Glycine soja genomic 3', genomic survey sequence.", XP002721471, retrieved from EBI accession No. EM_GSS:HN019107.
Database EMBL [Online] Nov. 1, 2008 (Nov. 1, 2008), "Glycine max clone BAC 71B1, * Sequencing in Progress *, 3 unordered pieces.", XP002721472, retrieved from EBI accession No. EM_HTG:EU721743.
Database EMBL [Online] Nov. 18, 2004 (Nov. 18, 2004), "Corn seedling-derived polynucleotide (cpds), SEQ ID 5567.", XP002721473, retrieved from EBI accession No. GSN:ADS70551.
Database Geneseq [Online] Aug. 23, 2007 (Aug. 23, 2007), "Cry1F event 281-24-236 transgene, SEQ ID 1.", XP002721474, retrieved from EBI accession No. GSN:AGD74685.
Database Geneseq [Online] Jul. 24, 2008 (Jul. 24, 2008), "B. napas PCR primer Rf1RV.", XP002721475, retrieved from EBI accession No. GSN:ARW87360.
Database Geneseq [Online] Apr. 1, 2010 (Apr. 1, 2010), "miRNA targeted gene sequence SEQ ID No. 237.", XP002721475, retrieved from EBI accession No. GSN:AXU86864.
Ron Brunoehler, Going public cuts soybean costs, corn and soybean digest, Feb. 2000.
Shaner, D. L. "Role of translocation as a mechanism of resistance to glyphosate." Weed Science 57.1 (2009): 118-123.
Database EMBL [Online] Jul. 18, 2022 (Jul. 18, 2002), "Agrobacterium tumefaciens str. C58 plasmid Ti, complete sequence.", retrieved from EBI accession No. EM_NEW:AE007871, Database accession No. AE007871.
Cloning vector pSLJ8313, T-DNA region disclosed in NCBI GenBank database accession Y18556 (published on Feb. 24, 1999).
European Search Report in EP18172142 completed Jun. 11, 2018.
International Search Report in PCT/US2011/063129 dated Apr. 17, 2012.
Supplementary European Search Report in EP 11845484 completed Mar. 11, 2014.
Baeumler et al. (2006). A Real-Time Quantitative PCR Detection Method Specific to Widestrike Transgenic Cotton (Event 281-24-236/3006-210-23). Journal of agricultural and food chemistry. 54. 6527-34. 10.1021/jf0610357.
Lebrun, *Z.mays* mRNA for EPSP-synthase, Genbank X63374 (Nov. 22, 1991).
Tengs et al., Glycine max transgenic GMO cassette genomic sequence, Genbank GQ497217 (Aug. 18, 2009).
Wohlleben et al., Nucleotide sequence of the phosphinothricin N-acetyltransferase gene from *Streptomyces viridochromogenes* Tü494 and its expression in *Nicotiana tabacum*, Gene, 70(1): 25-37 (Oct. 15, 1988).

\* cited by examiner

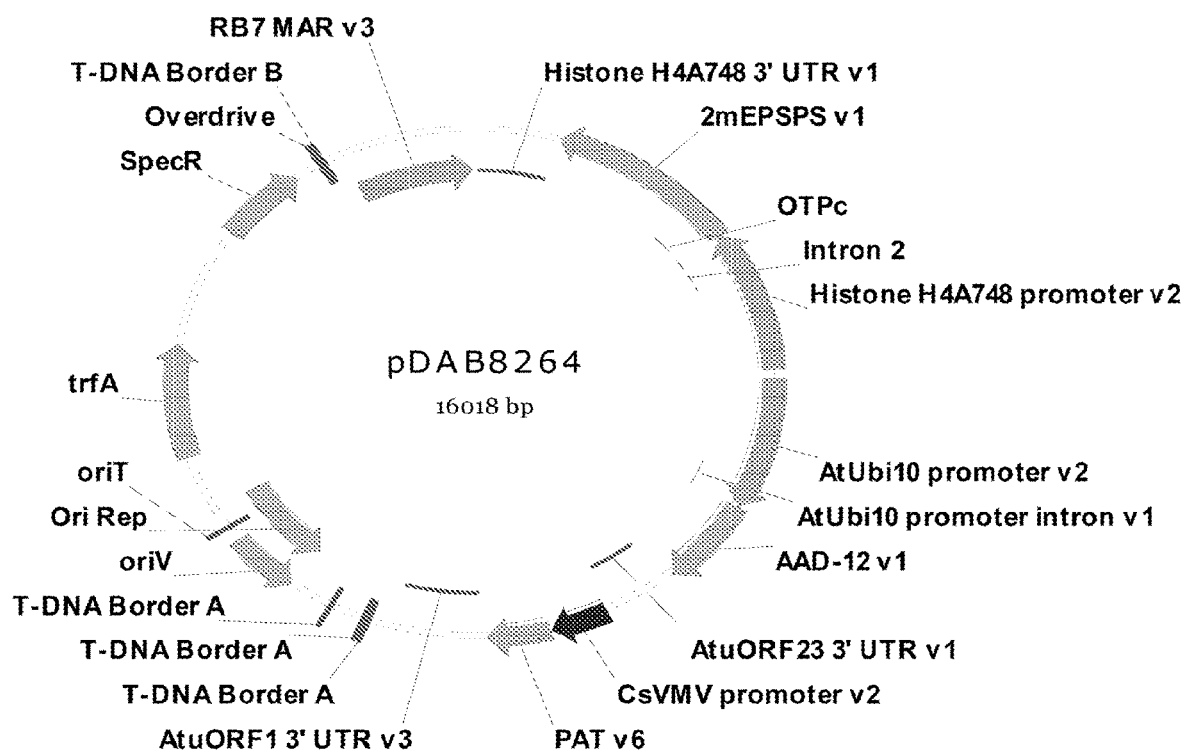
Figure 1. Plasmid Map of pDAB8264 containing the *2mepsps v1, aad*-12 and *pat* Expression Cassettes.

Figure 2. Schematic diagram of primer locations for soybean event pDAB8264.44.06.1 from 5' to 3' borders.
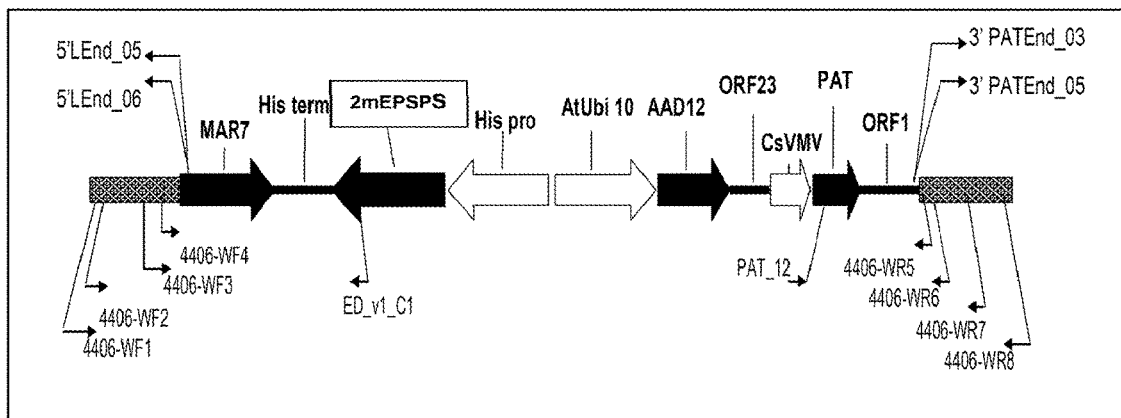
Figure 3. Schematic diagram depicting primer locations and genomic deletion in soybean event pDAB8264.44.06.1.
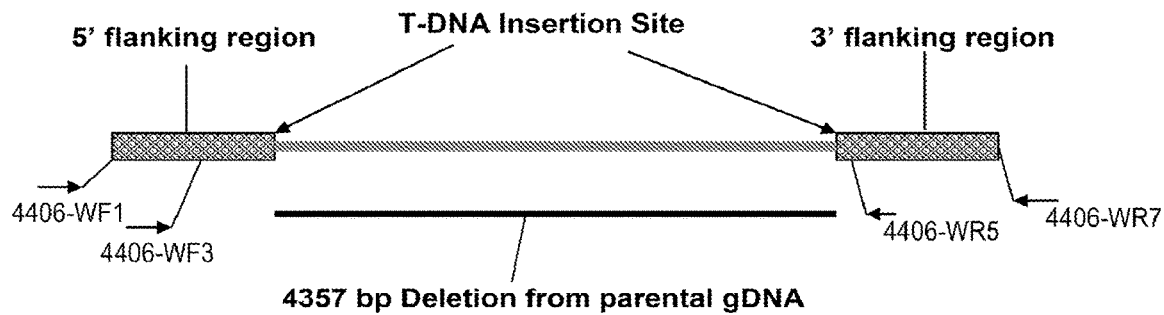

Figure 4. The schematic diagram depicts the primer locations for the Taqman assay of the soybean event pDAB8264.44.06.1.
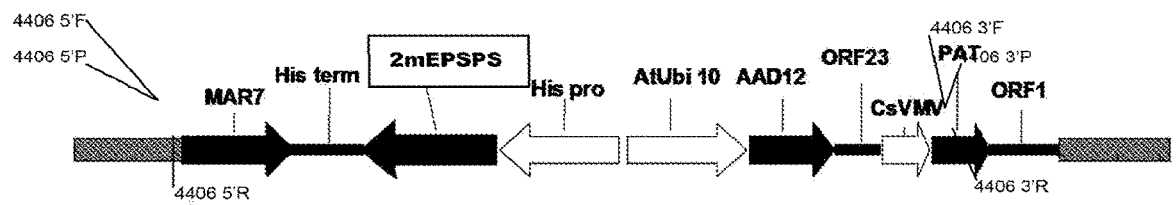

SEQUENCE LISTING

```
Sequence total quantity: 29
SEQ ID NO: 1              moltype = DNA  length = 570
FEATURE                   Location/Qualifiers
misc_feature              1..570
                          note = 5' flanking border sequence for the subject soybean
                          Event pDAB8264.44.06.1
source                    1..570
                          mol_type = other DNA
                          organism = synthetic construct
SEQUENCE: 1
agcttaacat acaagtaatg taatccacag tacgaaaaat gtgcaggttc ttatttgtgc   60
tccataattg tttcttgatt ccgatcaaag caagagcatc cagtctcaaa attttgtctt  120
ctcaattcac tcattcatca aaatcagcag ttttatgcat caacaagcat ggaatgttga  180
accacccatg attaagcccc atatcgttgt gttgagataa ctatcacctg aagttgtctt  240
ataaaaaaca catctgaata cttttataat catacctttc tcggccttt ggctaagatc   300
aagtgtagta tctgttctta tcagtttaat atctgatatg tgggtcattg gcccacatga  360
tattaaattt attttttgaa gggtggggcc tgacatagta gcttgctact ggggttctt   420
aagcgtagcc tgtgtcttgc actactgcat gggcctggcg caccctacga ttcagtgtat  480
atttatgtgt gataatgtca tgggttttta ttgttcttgt tgtttcctct ttaggaactt  540
acatgtaaac ggtaaggtca tcatggaggt                                    570

SEQ ID NO: 2              moltype = DNA  length = 1499
FEATURE                   Location/Qualifiers
misc_feature              1..1499
                          note = 3' flanking border sequence for the subject soybean
                          Event pDAB8264.44.06.1
source                    1..1499
                          mol_type = other DNA
                          organism = synthetic construct
SEQUENCE: 2
acagagaacg aatgtcgtgt gatatgtgga acaaggcaac gacaacaaca tacatgaatc   60
tcacaataga gtcggggtcg ccgagttgtg atgtaatcca tggcatggac atggtggccg  120
atcgaaaaag aaaaaagaaa tgcatgtata tgtgtgaaaa tgagagtttt ttttatccaa  180
ataataaaaa aaaattaatt atttacccaa aaaattattt acatgaccga tacgtacact  240
ttttccctta gttaagaaac accgatttct taattacatt tttttataca tttagaaatt  300
ggtttccttg gaaccgattt caaaatgttc atttttttt tcaaaccaa gttaagaaat   360
cggttccttg gaaacgact tcttaattgc tttttttttt gttttgtttt aaaattgttt  420
gtatttttat ttttttttgtt attaattgtc tatatttgtg ttctgtttaa attgaaaaca  480
atattatttt tcatatgttg ttaattctta atttcttatg catattttat gttttatcat  540
tttttaagag ttgaaatcct ttgtatttt atttatttg attattataa tacataatta   600
aacaacaact taattgaaat taaaaaatat atatttaact gacaagttga cttgaactaa  660
aatatttaaa ttacaaaata gatatgaaat tcaaacaat agaacaaaat atttaaattt  720
gaaataatac aacaaaaatt ttaaaataca aacaatatgg cataaaatta atgttgttgg  780
cctgagccta cacaatgggg ggaatgcgac acatggaaca tcattttggt ttacctgatt  840
cttggatatc cattttggtg tgtatacgag aggagacatg acaacctta gaatttcttt    900
tcattttgg gttggggcaa attcttggct tgtgacatgg tgaccaacat gcttcattgc   960
acaatttccc aagtaatcat ttgtacatgt tatagatact tttcagcgta tacacaagat 1020
gtatgtagtt cctatactca tggtgagcat gcttataaac aacaacatga gaacaaaaca 1080
tgtgcatttt ttgaaatttg tcacagtcac actacctttc atctagcttg accatgaaat 1140
ttctcactag ttgaatctct ctctccagtt aattgtctcc tagactaaga attgtatgtc 1200
```

```
gcattaatcg aactcaagaa caatgtgaga gtttgccttt ttctgtatgt ctttcatagc 1260
cttgtttaat acttttgtat aaacttcacc aaatgtaatc actcttgcga cttctctccc 1320
cctttggttg aacaatgcat tacacctagt ataggttgat tttaccaacr cacattgcca 1380
gattttgtgt tttcttgagt accaaattaa ttaactcagt gtccccatcg ccagccacca 1440
tcccatgcga gagtccactt ttcttgtgga atcttcctaa gctaattaat tgttagtta  1499

SEQ ID NO: 3            moltype = DNA   length = 25
FEATURE                 Location/Qualifiers
misc_feature            1..25
                        note = Primer 4406_WF1
source                  1..25
                        mol_type = other DNA
                        organism = synthetic construct
SEQUENCE: 3
aggttgtcat tccgctgaag aagat                                       25

SEQ ID NO: 4            moltype = DNA   length = 25
FEATURE                 Location/Qualifiers
misc_feature            1..25
                        note = Primer 4406_WF2
source                  1..25
                        mol_type = other DNA
                        organism = synthetic construct
SEQUENCE: 4
cacagtggac aattctgatt tctgg                                       25

SEQ ID NO: 5            moltype = DNA   length = 25
FEATURE                 Location/Qualifiers
misc_feature            1..25
                        note = Primer 4406_WF3
source                  1..25
                        mol_type = other DNA
                        organism = synthetic construct
SEQUENCE: 5
ggattgcatc tgaaacggat catat                                       25

SEQ ID NO: 6            moltype = DNA   length = 25
FEATURE                 Location/Qualifiers
misc_feature            1..25
                        note = Primer 4406_WF4
source                  1..25
                        mol_type = other DNA
                        organism = synthetic construct
SEQUENCE: 6
ggaatgttga accacccatg attaa                                       25

SEQ ID NO: 7            moltype = DNA   length = 25
FEATURE                 Location/Qualifiers
misc_feature            1..25
                        note = Primer 4406_WR5
source                  1..25
                        mol_type = other DNA
                        organism = synthetic construct
SEQUENCE: 7
catgtatgtt gttgtcgttg ccttg                                       25

SEQ ID NO: 8            moltype = DNA   length = 25
FEATURE                 Location/Qualifiers
misc_feature            1..25
                        note = Primer 4406_WR6
source                  1..25
                        mol_type = other DNA
                        organism = synthetic construct
SEQUENCE: 8
aacattttga aatcggttcc aagga                                       25

SEQ ID NO: 9            moltype = DNA   length = 25
FEATURE                 Location/Qualifiers
misc_feature            1..25
                        note = Primer 4406_WR7
source                  1..25
                        mol_type = other DNA
                        organism = synthetic construct
SEQUENCE: 9
aggctcaggc caacaacatt aattt                                       25

SEQ ID NO: 10           moltype = DNA   length = 27
FEATURE                 Location/Qualifiers
misc_feature            1..27
```

|  | note = Primer 4406_WR8 |  |
| --- | --- | --- |
| source | 1..27 |  |
|  | mol_type = other DNA |  |
|  | organism = synthetic construct |  |

SEQUENCE: 10
ggagagaagt cgcaacagtg attacat                                              27

| SEQ ID NO: 11 | moltype = DNA  length = 26 |
| --- | --- |
| FEATURE | Location/Qualifiers |
| misc_feature | 1..26 |
|  | note = Primer ED_v1_C1 |
| source | 1..26 |
|  | mol_type = other DNA |
|  | organism = synthetic construct |

SEQUENCE: 11
gagtaaagga gaccgagagg atggtt                                               26

| SEQ ID NO: 12 | moltype = DNA  length = 24 |
| --- | --- |
| FEATURE | Location/Qualifiers |
| misc_feature | 1..24 |
|  | note = Primer PAT_12 |
| source | 1..24 |
|  | mol_type = other DNA |
|  | organism = synthetic construct |

SEQUENCE: 12
gaacgcttac gattggacag ttga                                                 24

| SEQ ID NO: 13 | moltype = DNA  length = 10256 |
| --- | --- |
| FEATURE | Location/Qualifiers |
| misc_feature | 1..10256 |
|  | note = Plasmid pDAB8264 |
| source | 1..10256 |
|  | mol_type = other DNA |
|  | organism = synthetic construct |

SEQUENCE: 13
```
agtcagcatc atcacaccaa aagttaggcc cgaatagttt gaaattagaa agctcgcaat    60
tgaggtctac aggccaaatt cgctcttagc cgtacaatat tactcaccgg atcctaaccg   120
gtgtgatcat gggccgcgat taaaaatctc aattatattt ggtctaattt agtttggtat   180
tgagtaaaac aaattcgaac caaaccaaaa tataaatata tagtttttat atatatgcct   240
ttaagacttt ttatagaatt ttctttaaaa aatatctaga aatatttgcg actcttctgg   300
catgtaatat ttcgttaaat atgaagtgct ccattttttat taactttaaa taattggttg   360
tacgatcact ttcttatcaa gtgttactaa aatgcgtcaa tctctttgtt cttccatatt   420
catatgtcaa aacctatcaa aattcttata tatctttttc gaatttgaag tgaaatttcg   480
ataatttaaa attaaataga acatatcatt atttaggtat catattgatt tttatactta   540
attactaaat ttggttaact ttgaaagtgt acatcaacga aaaattagtc aaacgactaa   600
aataaataaa tatcatgtgt tattaagaaa attctcctat aagaatattt taatagatca   660
tatgttttgta aaaaaaatta attttttacta acacatatt ttacttatca aaaaatttgac   720
aaagtaagat taaataata ttcatctaac aaaaaaaaaa ccagaaaatg ctgaaaaccc   780
ggcaaaaccg aaccaatcca aaccgatata gttggtttgg tttgattttg atataaaccg   840
aaccaactcg gtccatttgc acccctaatc ataatagctt taatatttca agatattatt   900
aagttaacgt tgtcaaatatc ctggaaattt tgcaaaatga atcaagccta tatgcgtta   960
atatgaattt aaaagcagct cgatgtggtg gtaatatgta atttacttga ttctaaaaaa  1020
atatcccaag tattaataat ttctgctagg aagaaggtta gctacgattt acagcaaagc  1080
cagaatacaa tgaaccataa agtgattgaa gctcgaaata tacgaaggaa caaatatttt  1140
taaaaaaata cgcaatgact tggaacaaaa gaaagtgata tattttttgt tcttaaacaa  1200
gcatcccctc taaagaatgg cagttttcct ttgcatgtaa ctattatgct cccttcgtta  1260
caaaaatttt ggactactat tgggaacttc ttctgaaaat agtggccacc gcttaattaa  1320
ggcgcgccga cgaatgtccc cgatcaaatc tgagggacgt taaagcgatg ataaattgga  1380
accagaatat agaatctttg ttctgctcta gcttttcttc tgtacatttt ttacgattag  1440
actatgattt tcattcaata accaaaattc tgaagtttgt catcaagttg ctcaatcaaa  1500
cttgtaccgg tttgtttcgg ttttatatca gctcactgtt acactttaac caaaatcggt  1560
ttatgtctta ataaaggaat tgagtcggtt taactcatat ccgtaccaat cgacgtcgt  1620
gtccgcgttt cagtagcttt gctcattgtc ttctacggga actttcccgg acataggaac  1680
cgcccttcg ttatcctcat ccatcgtgaa atcaggaaat aagttcga agatttgagg  1740
tcaaagtcg aatttcatgt tgtctcttcc atttagatac aaaattgaag caattttcac  1800
caatttaatg ccaaaattta aaacaacgct gataaagtga aacttgattc gattttatatt  1860
tcaaccgaaa ctgctgaagc aagaagaaaa agcgtaatta cacataacaa gaacgctacc  1920
gcaaactact aaacgccaaa cccaatacaa agtaaaaacg cagacgctta agtgagaaac  1980
ccagaaaaca caaacgttga tcgggggatc cactagttct agagctttaa tcttgacgaa  2040
agtgctcagc acatcgaagt agtcgggaa ggtcttccgg gtgcacccag ggtcccggat  2100
ggtgacgggg acctcggcac aggcggcaag ggagaaagcc atcgccatcc tgtggtcgtc  2160
gtacgtgtcg atcgccgtca cgttcagctt ctccggcggc gtgatgatgc agtagtccgg  2220
cccttcctca acagatgctc ccagcttggt tagctccgtc cggatcgcaa ccatcctctc  2280
ggtctccttt actctccagg aagccacgtc tctgatggct gtcggggcat cgcaaagag  2340
ggcaaccaca gcaagagtca tggcgacatc aggcatcttg ttcatgttga catcaatcgc  2400
cttgaggtgt ttcctcccaa atggctcccg cggtgggcca gtaacagtta cgctagtctc  2460
ggtccatgta accttcgctc ccatcatctc cagtacctca gcaaacttca catcccctg  2520
caaactggtg gtgccacaac cttccacagt cacagtccct ccagtaattg cagcaccagc  2580
caagaaatag cttgcgcttg aggcatcacc ttcaacatag gcatttttag gggacttgta  2640
```

```
tttttgacct cccttaatgt agaatctgtc ccagctatca gaatgctctg ctttcacacc    2700
aaaacgctcc atcaatctca atgtcatttt gacgtacgga atggagatta atttatcaat    2760
gatttcaatc tccacatccc caagagccaa aggagcagcc atcagcaagg cactcaagta    2820
ctgactgctg atggagccag acagcttgac cttgccacca ggtagccctc cgattccatt    2880
gacacgaaca ggtgggcagt cagtgccaag gaaacaatca acatctgcac caagctgctt    2940
caatccgaca accaagtcgc caatgggtct ctcccctcatt cttggtactc catcaagcac    3000
gtaagttgca tttccaccag cagcagtaac agctgctgtc aaggaccgca ttgcgattcc    3060
agcattcccc aagaagagct gcacttcctc tttagcatcc tcaactggga actttccacc    3120
acagccaaca actacagctc tttttgcagc tttgtccgct tcgacagaga gaccaagagt    3180
cctcaaggcc ccgagcatgt agtggacatc ctcactgttc agcaggttat caaccactgt    3240
tgtcccctcg gacagggcgg cgagtaggag gatccggttg gaaagcgact tggaccccgg    3300
cagcttgacg gtgccggaga tctccttgat gggctgcagc acgatctcct cggcgccggc    3360
catgcaccgg atccttccgc cgttgctgac gttgccgagg cttctggagg agcggcgggc    3420
gacggggagg ctggcggtgg acttgagccc ctggaacgga gcgacggcgg tggccgacga    3480
ggccatcatc acggtgggcg ccatagacag cggcggcagg tacgacagcg tctcgaactt    3540
cttgttgccg taggccggcc acacctgcat acattgaact cttccaccgt tgctgggaag    3600
ggtggagaag tcgttagcct tcttggtggt ggggaaggcg gcgttggact taaggccggt    3660
gaacggagcc accatgttgg cctgagcagg ggcggtccgg ctaacggtcg cgactgagga    3720
ggagatcgaa gccatgggga tctgcgcatt taacaagaaa ttgaacagtc aattgggat    3780
tttcattatc cataactaaa ttttgaagaa attggaatac taaacgtcac cacttaaaac    3840
cctaatccag atgaatcgtt atcgaaccag atataaccaa aaggggcaaa attgactcga    3900
aaacccctagt tctcgataca cggctaggta atgacaatcg cacacagaca aatctggtta    3960
tacagaactt cgaagcaaga aaaaacgat gaagaatgca tcatccaata aatcgactag    4020
actcaatctt cacaggttta tcgatccagc aaacttaaaa gacggacctt tattttcaaa    4080
ctggaatggg acaaaacccg aaactctatt gtcgtaaaat cagatcgcgg agacagtaac    4140
agaaaaaaca ttaaaaagta atggaaagac ctaaacccct gatctaatta caaacaaatc    4200
atacctgttc ttcgcctgag gggttcgaaa tcgataagct tggatcctct agagtcgaga    4260
gaaattgatg tctgtagaag aagaagaacg gttaagagta gatttgggtg agaaagatgt    4320
gaaattgttt ttataggcaa agacggagag tctattttttt gagcaatcag atcgcatatt    4380
aaatctaacg gctgagatat cgatccgtgt gtacaataaa atgatgtata aaccgtcgat    4440
ctgtttttaat cgacggttca tattagtgat ccgcgtgatg gcagtgatag ccactaagaa    4500
tcgtctttttg ttttacatgt ggcgccacaa attagggtaa tgaagcggca atattttgga    4560
actcggaaaa taaaattgcg ccatcacatt atttgaaaat tttcacatgc ttttatttta    4620
aaaacccacg aattacaagt tacaaccgaa aaagatttat aatatagtga tttatactaa    4680
ttttgtagta gcttaatgta tattgatact ggaaaaacaa tgacaatcat atgttagtat    4740
tatcaagtta tcgtattgat attgatattg gaacatacaa tgggtattgc cttctttcga    4800
ccataaatat caccaaattt acaaagtttg tgtataccaa gttatcaatt gtaaatggga    4860
tgtcaacatt ttaatttccc tttgagaaac tatagaccaa aagaacacac ttcaatagat    4920
aaagtaacta tttacataag aggttttaaa atcacattaa caaaaataat taccaaccgg    4980
cactcacaaa tacaaacaga gcacacgaca tgtcaaagcc acaagtaaat tcgttgagtg    5040
gtggtttcat tacaattgtg tcacttgcag cacaaactat cttgctctgg aatcatctc    5100
agcatcaaag atcatgctca cttcagggga acttagtgta tccatgcctc gactcatatt    5160
tctcctcgac atgcatcctg caggggcgcg ccatgccgg gcaagcggcc gcacaagttt    5220
gtacaaaaaa gcaggctccg cggtgactgc ctgaaaagct tgtcgacctg caggtcaacg    5280
gatcaggata ttcttgttta agatgttgaa ctctatggag gtttgtatga actgatgatc    5340
taggaccgga taagttccct tcttcatagc gaacttattc aaagaatgtt ttgtgtatca    5400
ttcttgttac attgttatta atgaaaaaat attattggtc attggacgta acacgagtgt    5460
taaatatgga ccaggcccca aataagatcc attgatatat gaattaaata acaagaataa    5520
atcgagtcac caaccacttt gccttttttta acgagacttg ttccaccaact tgatacaaaa    5580
gtcattatcc tatgcaaatc aataatcata caaaatatc caataacact aaaaaattaa    5640
aagaaatgga taatttcaca atatgttata cgataaagaa gttacttttc caagaaattt    5700
actgatttta taagcccact tgcattagat aaatggcaaa aaaaaacaaa aaggaaaaga    5760
aataaagcac gaagaattct agaaaatacg aaatacgctt caatgcagtg ggacccacgg    5820
ttcaattatt gccaattttc agctccaccg tatatttaaa aaatttaacg ataatgctaa    5880
aaaaatataa atcgtaacga tcgttaaatc tcaacggctg gatcttatga cgaccgttag    5940
aaattgtggt tgtcgacgag tcagtaataa acggcgtcaa agtggttgca gccggcacac    6000
acgagtcgtg tttatcaact caaagcacaa atacttttcc tcaacctaaa aataaggcaa    6060
ttagccaaaa acaactttgc gtgtaaacaa cgctcaatac acgtgtcatt ttattattag    6120
ctattgcttc accgccttag ctttctcgtg acctagtcgt cctcgtcttt tcttcttctt    6180
cttctataaa acaatccca aagcttcttc ttcacaattc agatttcaat ttctcaaaat    6240
cttaaaaact ttctctcaat tctctctacc gtgatcaagg taaatttctg tgttccttat    6300
tctctcaaaa tcttcgattt tgttttcgtt cgatcccaat ttcgtatatg ttctttggtt    6360
tagattctgt taatcttaga tcgaagacga ttttctgggt ttgatcgtta gatatctct    6420
taattctcga ttagggtttc ataaaatatca tccgattttgt tcaaataatt tagtttttgt    6480
cgaataatta ctcttcgatt tgtgatttct atctagatct ggtgttagtt tctagtttgt    6540
gcgatcgaat ttgtcgatta atctgagttt ttctgattaa cagagatctc catggctcag    6600
accactctcc aaatcacacc cactggtgcc accttgggtg ccacagtcac tggtgttcac    6660
cttgccacac ttgacgatgc tggtttcgct gccctccatc agcctggct tcaacatgca    6720
ctcttgatct tccctgggca acacctcagc aatgaccaac agattaccttt tgctaaacgc    6780
tttggagcaa ttgagaggat tggcggaggt gacattgttg ccatatccaa tgtcaaggca    6840
gatggcacag tgcgccagca ctctcctgct gagtgggatg acatgatgaa ggtcattgtg    6900
ggcaacatgg cctggcacgc cgactcaacc tacatgccag tcatggctca aggagctgtg    6960
ttcagcgcag aagttgtccc agcagttggg ggcagaacct gctttgctga catgagggca    7020
ggctacgatg ccccttgatga ggcaacccgt gctcttgtca accaaaggtc tgctcgtcac    7080
tcccttgtgt attctcagag caagttggga catgtccaac aggccgggtc agcctacata    7140
ggttatggca tggacaccac tgcaactcct ctcagaccat tggtcaaggt gcatcctgag    7200
actggaaggc ccagcctctt gatcggccgc catgcccatg ccatccctgg catggatgca    7260
gctgaatcag agcgcttcct tgaaggactt gttgactggg cctgccaggc tcccagagtc    7320
catgctcacc aatgggctgc tggagatgtg gttgtgtggg acaaccgctg tttgctccac    7380
```

```
cgtgctgagc cctgggattt caagttgcca cgtgtgatgt ggcactccag actcgctgga    7440
cgcccagaaa ctgagggtgc tgccttggtt tgagtagtta gcttaatcac ctagagctcg    7500
gtcaccagca taatttttat taatgtacta aattactgtt ttgttaaatg caattttgct    7560
ttctcggat  tttaatatca aaatctattt agaaatacac aatattttgt tgcaggcttg    7620
ctggagaatc gatctgctat cataaaaatt acaaaaaaat tttatttgcc tcaattattt    7680
taggattggt attaaggacg cttaaattat ttgtcgggtc actacgcatc attgtgattg    7740
agaagatcag cgatacgaaa tattcgtagt actatcgata atttatttga aaattcataa    7800
gaaaagcaaa cgttacatga attgatgaaa caatacaaag acagataaag ccacgcacat    7860
ttaggatatt ggccgagatt actgaatatt gagtaagatc acggaatttc tgacaggagc    7920
atgtcttcaa ttcagcccaa atggcagttg aaatactcaa accgcccat  atgcaggagc    7980
ggatcattca ttgtttgttt ggttgccttt gccaacatgg gagtccaagg ttgcggccgc    8040
gcgccgaccc agctttcttg tacaaagtgg ttgcggccgc ttaattaaat ttaaatgccc    8100
gggcgtttaa acgcggccgc ttaattaagg ccggcctgca gcaaacccag aaggtaatta    8160
tccaagatgt agcatcaaga atccaagttt tacgggaaca actatggaag tattatgtaa    8220
gctcagcaag aagcagatca atatgcggca catatgcaac ctatgttcaa aaatgaagaa    8280
tgtacagata caagatccta tactgccaga atacgaagaa gaatacgtag aaattgaaaa    8340
agaagaacca ggcgaagaaa agaatcttga agacgtaagc actgacgaca caatgaaaa     8400
gaagaagata aggtcggtga ttgtgaaaga gacatagagg acacatgtaa ggtggaaaat    8460
gtaagggcgg aaagtaacct tatcacaaag gaatcttatc ccccactact tatccttta    8520
tattttccg tgtcattttt gcccttgagt tttcctatat aaggaaccaa gttcggcatt     8580
tgtgaaaaca agaaaaaatt tggtgtaagc tattttcttt gaagtactga ggatacaact    8640
tcagagaaat ttgtaagttt gtagatctcc atgtctccag agaggagacc agttgagatt    8700
aggccagcta cagcagctga tatggccgcg gtttgtgata tcgttaacca ttacattgag    8760
acgtctacag tgaactttag gacagagcca caaacaccac aagagtggat tgatgatcta    8820
gagaggttgc aagatagata cccttggttg gttgctgagg ttgagggtgt tgtggctggt    8880
attgcttacg ctgggccctg gaaggctagg aacgcttacg gttgacagt  tgagagtact    8940
gtttacgtgt cacataggca tcaaaggttg ggcctaggat ccacattgta cacacatttg    9000
cttaagtcta tggaggcgca aggttttaag tctgtggttg ctgttatagg ccttccaaac    9060
gatccatctg ttaggttgca tgaggctttg ggatacacag cccggggtac attgcgcgca    9120
gctgataca  agcatggtgg atggcatgat gttggttttt ggcaaaggga ttttgagttg    9180
ccagctcctc caaggccagt taggccagtt acccagatct gaggtaccct gagcttgagc    9240
ttatgagctt atgagcttag agctcggatc cactagtaac ggccgccagt gtgctggaat    9300
tcgcccttga ctagataggc gcccagatcg gcggcaatag cttcttagcg ccatcccggg    9360
ttgatcctat ctgtgttgaa atagttgcgg tgggcaaggc tctcttttcag aaagacaggc    9420
ggccaaagga acccaaggtg aggtgggcta tggctctcag ttccttgtgg aagcgcttgg    9480
tctaaggtgc agaggtgtta gcgggatgaa gcaaaagtgt ccgattgtaa caagatatgt    9540
tgatcctacg taaggatatt aaagtatgta ttcatcacta atataatcag tgtattccaa    9600
tatgtactac gatttccaat gtctttattg tcgccgtatg taatcggcgt cacaaaataa    9660
tccccggtga ctttctttta atccaggatg aaataatatg ttattataat ttttgcgatt    9720
tggtccgtta taggaattga agtgtgcttg cggtcgccac cactcccatt tcataatttt    9780
acatgtattt gaaaaataaa aatttatggt attcaattta aacacgtata cttgtaaaga    9840
atgatatctt gaaagaaata tagtttaaat atttattgat aaaaataacaa gtcaggtatt    9900
atagtccaag caaaaacata aatttattga tgcaagttta aattcagaaa tatttcaata    9960
actgattata tcagctgtta cattgccgta gatgaaagac tgagtgcgat attatggtgt   10020
aatacatagc ggccgggttt ctagtcaccg gttaggatcc gtttaaactc gaggctagcg   10080
catgcacata gacacacaca tcatctcatt gatgcttggt aataattgtc attagattgt   10140
ttttatgcat agatgcactc gaaatcagcc aatttttagac aagtatcaaa cggatgtgac   10200
ttcagtacat taaaaacgtc cgcaatgtgt tattaagttg tctaagcgtc aatttg        10256

SEQ ID NO: 14           moltype = DNA   length = 859
FEATURE                 Location/Qualifiers
misc_feature            1..859
                        note = Provides part of the 5' soybean genomic flanking and
                        part of the 5' insert sequence
source                  1..859
                        mol_type = other DNA
                        organism = synthetic construct
SEQUENCE: 14
agcttaacat acaagtaatg taatccacag tacgaaaaat gtgcaggttc ttatttgtgc      60
tccataattg tttcttgatt ccgatcaaag caagagcatc cagtctcaaa attttgtctt     120
ctcaattcac tcattcatca aaatcagcag ttttatgcat caacaagcat ggaatgttga     180
accacccatg attaagcccc atatcgttgt gttgagataa ctatcacctg aagttgtctt     240
ataaaaaaca catctgaata cttttataat catacctttc tcggccttt  ggctaagatc    300
aagtagtta tctgttctta tcagtttaat atctgatatg tgggtcattg gcccacatga     360
tattaaattt attttttgaa gggtggggcc tgacatagta gcttgctact gggggttctt     420
aagcgtagcc tgtgtcttgc actactgcat gggcctggcg cacccctacga ttcagtgtat    480
atttatgtgt gataatgtca tgggtttta ttgttcttgt tgtttcctct ttaggaactt      540
acatgtaaac ggtaaggtca tcatggaggt ccgaatagtt tgaaattaga aagctcgcaa     600
ttgaggtcta caggccaaat tcgctcttag ccgtacaata ttactcaccg gatcctaacc     660
ggtgtgatca tgggccgcga ttaaaaatct caattatatt tggtctaatt tagtttggta     720
ttgagtaaaa caaattcgaa ccaaaccaaa atataaatat atagtttta tatatatgcc      780
tttaagactt tttatagaat tttctttaaa aaatatctag aaatatttgc gactcttctg     840
gcatgtaata tttcgttaa                                                  859

SEQ ID NO: 15           moltype = DNA   length = 1719
FEATURE                 Location/Qualifiers
misc_feature            1..1719
                        note = Part of the 3' soybean genomic flanking and part of
                        the 3' insert sequence
```

```
source                  1..1719
                        mol_type = other DNA
                        organism = synthetic construct
SEQUENCE: 15
gcacatagac acacacatca tctcattgat gcttggtaat aattgtcatt agattgtttt      60
tatgcataga tgcactcgaa atcagccaat tttagacaag tatcaaacgg atgtgacttc     120
agtacattaa aaacgtccgc aatgtgttat taagttgtct aagcgtcaat ttgatttaca     180
attgaatata tcctgcccca gccagccaac agctcgattt acagagaacg aatgtcgtgt     240
gatatgtgga acaaggcaac gacaacaaca tacatgaatc tcacaataga gtcggggtcg     300
ccgagttgtg atgtaatcca tggcatggac atggtggccg atcgaaaaag aaaaagaaa      360
tgcatgtata tgtgtgaaaa tgagagtttt ttttatccaa ataataaaaa aaaattaatt     420
atttacccaa aaaattattt acatgaccga tacgtacact ttttccctta gttaagaaac     480
accgatttct taattacatt ttttttataca tttagaaatt ggtttccttg aaccgatttt     540
caaaatgttc atttttttt tcaaaaccaa gttaagaact cggttccttg gaaaacgact      600
tcttaattgc tttttttttt gttttgtttt aaaattgttt gtattttat ttttttttgtt     660
attaattgtc tatatttgtg ttctgtttaa attgaaaaca atattatttt tcatatgttg     720
ttaattctta atttcttatg catatttat gtttatcat tttttaagag ttgaaatcct       780
ttgtatttt atttttatttg attattataa tacataatta aacaacaact taattgaaat     840
taaaaaatat atatttaact gacaagttga cttgaactaa aatatttaaa ttacaaaata     900
gatatgaaat tacaaacaat agaacaaat atttaaattt gaataatac aacaaaaatt       960
ttaaaataca aacaatatgg cataaaatta atgttgttgg cctgagccta cacaatgggg    1020
ggaatgcgac acatggaaca tcattttggt ttacctgatt cttggatatc cattttggtg    1080
tgtatacgag aggagacatg acaacccttta gaatttcttt tcattttttgg gttgggggcaa 1140
attcttggct tgtgacatgg tgaccaacat gcttcattgc acaatttccc aagtaatcat   1200
ttgtacatgt tatagatact tttcagcgta tacacaagat gtatgtagtt cctatactca    1260
tggtgagcat gcttataaac aacaacatga gaacaaaaca tgtgcatttt ttgaaatttg    1320
tcacagtcac actaccttc atctagcttg accatgaaat ttctcactag ttgaatctct     1380
ctctccagtt aattgtctcc tagactaaga attgtatgtc gcattaatcg aactcaagaa    1440
caatgtgaga gtttgccttt ttctgtatgt ctttcatagc cttgtttaat acttttgtat    1500
aaacttcacc aaatgtaatc actcttgcga cttctctccc ccttggttg aacaatgcat     1560
tacacctagt ataggttgat tttaccaacr cacattgcca gattttgtgt tttcttgagt    1620
accaaattaa ttaactcagt gtccccatcg ccagccacca tcccatgcga gagtccactt    1680
ttcttgtgga atcttcctaa gctaattaat tgttagtta                          1719

SEQ ID NO: 16       moltype = DNA  length = 98
FEATURE             Location/Qualifiers
misc_feature        1..98
                    note = A 98 base pair sequence spanning the 5' integration
                    junction
source              1..98
                    mol_type = other DNA
                    organism = synthetic construct
SEQUENCE: 16
ttgttcttgt tgtttcctct ttaggaactt acatgtaaac ggtaaggtca tcatggaggt     60
ccgaatagtt tgaaattaga aagctcgcaa ttgaggtc                            98

SEQ ID NO: 17       moltype = DNA  length = 131
FEATURE             Location/Qualifiers
misc_feature        1..131
                    note = A 131 base pair sequence spanning the 3' integration
                    junction
source              1..131
                    mol_type = other DNA
                    organism = synthetic construct
SEQUENCE: 17
aaacgtccgc aatgtgttat taagttgtct aagcgtcaat ttgatttaca attgaatata     60
tcctgcccca gccagccaac agctcgattt acagagaacg aatgtcgtgt gatatgtgga    120
acaaggcaac g                                                        131

SEQ ID NO: 18       moltype = DNA  length = 26
FEATURE             Location/Qualifiers
misc_feature        1..26
                    note = Primer 4406_5'F
source              1..26
                    mol_type = other DNA
                    organism = synthetic construct
SEQUENCE: 18
ttgttcttgt tgtttcctct ttagga                                         26

SEQ ID NO: 19       moltype = DNA  length = 24
FEATURE             Location/Qualifiers
misc_feature        1..24
                    note = Primer 4406_5'R
source              1..24
                    mol_type = other DNA
                    organism = synthetic construct
SEQUENCE: 19
gacctcaatt gcgagctttc taat                                           24
```

```
SEQ ID NO: 20              moltype = DNA   length = 17
FEATURE                    Location/Qualifiers
misc_feature               1..17
                           note = Probe 4406_5'P
source                     1..17
                           mol_type = other DNA
                           organism = synthetic construct
SEQUENCE: 20
catggaggtc cgaatag                                                      17

SEQ ID NO: 21              moltype = DNA   length = 24
FEATURE                    Location/Qualifiers
misc_feature               1..24
                           note = Primer 4406_3'F
source                     1..24
                           mol_type = other DNA
                           organism = synthetic construct
SEQUENCE: 21
aaacgtccgc aatgtgttat taag                                              24

SEQ ID NO: 22              moltype = DNA   length = 22
FEATURE                    Location/Qualifiers
misc_feature               1..22
                           note = Primer 4406_3'R
source                     1..22
                           mol_type = other DNA
                           organism = synthetic construct
SEQUENCE: 22
cgttgccttg ttccacatat ca                                                22

SEQ ID NO: 23              moltype = DNA   length = 16
FEATURE                    Location/Qualifiers
misc_feature               1..16
                           note = Probe 4406_3'P
source                     1..16
                           mol_type = other DNA
                           organism = synthetic construct
SEQUENCE: 23
acagagaacg aatgtc                                                       16

SEQ ID NO: 24              moltype = DNA   length = 24
FEATURE                    Location/Qualifiers
misc_feature               1..24
                           note = Primer GMS116F
source                     1..24
                           mol_type = other DNA
                           organism = synthetic construct
SEQUENCE: 24
gtaatatggg ctcagaggaa tggt                                              24

SEQ ID NO: 25              moltype = DNA   length = 23
FEATURE                    Location/Qualifiers
misc_feature               1..23
                           note = Primer GMS116R
source                     1..23
                           mol_type = other DNA
                           organism = synthetic construct
SEQUENCE: 25
atggagaaga acattggaat tgc                                               23

SEQ ID NO: 26              moltype = DNA   length = 23
FEATURE                    Location/Qualifiers
misc_feature               1..23
                           note = Probe GMS116Probe
source                     1..23
                           mol_type = other DNA
                           organism = synthetic construct
SEQUENCE: 26
ccatggcccg gtaccatctg gtc                                               23

SEQ ID NO: 27              moltype = DNA   length = 13659
FEATURE                    Location/Qualifiers
misc_feature               1..13659
                           note = Event pDAB8264.44.06.1
source                     1..13659
                           mol_type = other DNA
                           organism = synthetic construct
SEQUENCE: 27
ccgctgaaga agatcaagtg tgtgaaccaa agtgaaaata atgtttagaa gccaacacag       60
```

```
tggacaattt tgatttctgg ttaatgggtg tattaaaaat atcagaaaac tttcaaatat    120
ctcgagcagg cagttgggtt gcctaatcca tcacttgatc tcaaagattc ttgttgtcaa    180
gcttcgatga gtagcgaaac ctaccgtgtg ggctctaagc tttaggttgc cattgacgat    240
cttgacacga catatgacct atgatagcaa ttcaaacatg gttcatatca gctgagttgc    300
agacttagct gctagcattt cacgttgtga atgcaagagg aaaaatacat agaaaaagag    360
ggaacaaaat tgttaaccct ccatatgtac aggttttagc ctcaatttta cccattgatt    420
gatttattat tgaaaagtaa tcacttatca gaaccagagt ttgtaattca gcttgtatcg    480
tacctatcta tatcttagtc aaatttgtgt ataataagta tttaaatgtg agtctctttt    540
atttaattag tttaaataat tggaatacaa ttggcaaatg ggcacttcaa ctataattag    600
tgaattgatt tagttgactg ttatgaagta ttttacttaa gttagtaata gtagagtgat    660
gtttgatgaa ttaaacttaa gattggttga agttattgat ctcactggat ccatagtttg    720
gtctgtggga ttgcatctga aacggatcat atggttttgt tttgtgactg aattgtggca    780
atgtaacacc tggactttt cacaactatt gtataaatcc agtatatctc acgtgaatct    840
gaaattagta gcatgcttaa catataagta tcgatttatc taatcagttt ccatatttat    900
gaaaactgca ctgttgaaaa ttgtgcaagc ttaacataca agtaatgtaa tccacagtac    960
gaaaaatgtg caggttctta tttgtgctcc ataattgttt cttgattccg atcaaagcaa   1020
gagcatccag tctcaaaatt ttgtcttctc aattcactca ttcatcaaaa tcagcagttt   1080
tatgcatcaa caagcatgga atgttgaacc acccatgatt aagccccata tcgttgtgtt   1140
gagataacta tcacctgaag ttgtcttata aaaacacat ctgaatactt ttataatcat    1200
acctttctcg gccttttggc taagatcaag tgtagtatct gttcttatca gtttaatatc   1260
tgatatgtgg gtcattggcc cacatgatat taaatttatt ttttgaaggg tggggcctga   1320
catagtagct tgctactggg ggttcttaag cgtagcctgt gtcttgcact actgcatggg   1380
cctggcgcac cctacgattc agtgtatatt tatgtgtgat aatgtcatgg gttttttattg   1440
ttcttgttgt ttcctctttta ggaacttaca tgtaaacggt aaggtcatca tggaggtccg   1500
aatagtttga aattagaaag ctcgcaattg aggtctacag gccaaattcg ctcttagccg   1560
tacaatatta ctcaccggat cctaaccggt gtgatcatga gccgcgatta aaaatctcaa   1620
ttatatttgg tctaatttag tttggtattg agtaaaacaa attcgaacca accaaaata    1680
taaatatata gttttatat atatgcctt aagactttt atagaatttt ctttaaaaaa    1740
tatctagaaa tatttgcgac tcttctggca tgtaatattt cgttaaatat gaagtgctcc   1800
atttttatta actttaaata attggttgta cgatcacttt cttatcaagt gttactaaaa   1860
tgcgtcaatc tctttgttct tccatattca tatgtcaaaa cctatcaaaa ttcttatata   1920
tcttttcga atttgaagtg aaatttcgat aatttaaaat taaatagaac atatcattat   1980
ttaggtatca tattgatttt tatacttaat tactaaattt ggttaacttt gaaagtgtac   2040
atcaacgaaa aattagtcaa acgactaaaa taaataaata tcatgtgtta ttaagaaaat   2100
tctcctataa gaatatttta atagatcata tgtttgtaaa aaaaattaat ttttactaac   2160
acatatattt acttatcaaa aatttgacaa agtaagatta aataatatt catctaacaa    2220
aaaaaaaacc agaaatgct gaaacccgg caaaacgaa ccaatccaaa ccgatatagt      2280
tggttggtt tgattttgat ataaaccgaa ccaactcggt ccatttgcac ccctaatcat    2340
aatagcttta atatttcaag atattattaa gttaacgttg tcaatatcct ggaaattttg   2400
caaaatgaat caagcctata tggctgtaat atgaatttaa aagcagctcg atgtggtggt   2460
aatatgtaat ttacttgatt ctaaaaaaat atcccaagta ttaataattt ctgctaggaa   2520
gaaggttagc tacgatttac agcaaagcca gaatacaatg aaccataaag tgattgaagc   2580
tcgaaatata cgaaggaaca aatatttta caattgacttg gaacaaaaga                2640
aagtgatata ttttttgttc ttaaacaagc atccccctcta aagaatggca gttttccttt   2700
gcatgtaact attatgctcc cttcgttaca aaaattttgg actactattg ggaacttctt   2760
ctgaaaatag tggccaccgc ttaattaagg cgcgccgacg aatgtccccg atcaaatctg   2820
agggacgtta aagcgatgat aaattggaac cagaatatag aatctttgtt ctgctctagc   2880
ttttcttctg tacattttt acgattagac tatgattttc attcaataac caaaattctg   2940
aagtttgtca tcaagttgct caatcaaact tgtaccggtt tgtttcggtt ttatatcagc   3000
tcactgttac actttaacca aaatcggttt atgtcttaat aaaggaattg agtcggttta   3060
actcatatcc gtaccaatgc gacgtcgtgt ccgcgtttca gtagctttgc tcattgtctt   3120
ctacgggaac tttcccggac ataggaaccg ccctttcgtt atcctcatcc atcgtgaaat   3180
caggaaataa atgttcgaag atttgaggtc aaaagtcgaa tttcatgttg tctcttctat   3240
ttagatacaa aattgaagca attttcacca atttaatgcc aaaatttaaa acaacgctga   3300
taaagtgaaa cttgattcga tttatatttc aaccgaagct gctgaagcaa gaagaaaaag   3360
cgtaattaca cataacaaga acgctaccgc aaactactaa acgccaaacc caatacaaaa   3420
gtaaaacgca gacgcttaag tgagaaaccc agaaaacaca aacgcggatc ggggggatcca   3480
ctagttctag agcttaattc ttgacgaaag tgctcagcac atcgaagtag tcggggaagg   3540
tcttccgggt gcacccaggg tcccggatgg tgacgggggac ctcggcacag gcggcaaggg   3600
agaaagccat cgccatcctg tggtcgtcgt acgtgtcgat cgccgtcacg ttcagcttct   3660
ccggcggcgt gatgatgcag tagtccggcc cttcctcaac agatgctccc agcttggtta   3720
gctccgtccg gatcgcaacc atcctctcgg tctccttac tctccaggaa gccacgtctc    3780
tgatggctgt cgggccatcg gcaaagaggg caaccacag aagagtcatg gcgacatcag    3840
gcatcttgtt catgttgaca tcaatcgcct tgaggtgttt cctcccaaat ggctccccaa   3900
gtgggccagt aacagttacg ctagtctcgg tccatgtaac cttcgctccc atcatctcca   3960
gtacctcagc aaacttcaca tcaccctgca aactggtggt gccacaacct tccacagtca   4020
cagtccctcc agtaattgca gcaccagcca agaaatagct tgcgcttgag gcatcacctt   4080
caacatagge atttttaggg gacttgtatt tttgacctcc cttaatgtag aatctgtccc   4140
agctatcaga atgctctgct ttcacaccaa aacgctccat caatctcaat gtcatttcga   4200
cgtacggaat ggagattaat ttatcaatga tttcaatctc cacatcccca agagccaaag   4260
gagcagccat cagcaaggca ctcaagtact gactgctgat ggagccagac agcttgacct   4320
tgccaccagg tagccctccg attccattga cacgaacagg tgggcagtca gtgccaagga   4380
aacaatcaac atctgcacca agctgcttca atccgacaac caagtcgcca atgggtctct   4440
ccctcattct tggtactcca tcaagcacgt aagttgcatt tccaccagca gcagtaacag   4500
ctgctgtcaa ggaccgcatt gcgattccag cattccccaa gaagagctgc acttcctctt   4560
tagcatcctc aactgggaac tttccaccac agccaacaac tacagctctt ttggcagctt   4620
tgtccgcttc gacagagaga ccaagagtcc tcaggccccc gagcatgtag tggacatcct   4680
cactgttcag caggttatca accactgttg tcccctcgga cagggcggcg agtaggagga   4740
tccggttgga aagcgacttg gaccccggca gcttgacggt gccggagatc tccttgatgg   4800
```

```
gctgcagcac gatctcctcg gcgccggcca tgcaccggat ccttccgccg ttgctgacgt  4860
tgccgaggct tctggaggag cggcgggcga cggggaggct ggcggtggac ttgagcccct  4920
ggaacggagc gacggcggtg gccgacgagg ccatcatcac ggtgggcgcc atagacagcg  4980
gcggcaggta cgacagcgtc tcgaacttct tgttgccgta ggccggccac acctgcatac  5040
attgaactct tccaccgttg ctgggaaggg tggagaagtc gttagccttc ttggtggtgg  5100
ggaaggcggc gttggactta aggccggtga acggagccac catgttggcc tgagcagggg  5160
cggtccggct aacggtcgcg actgaggagg agatcgaagc catggggatc tgcgcattta  5220
acaagaaatt gaacagtcaa ttggggattt tcattatcca taactaaatt ttgaagaaat  5280
tggaatacta aacgtcacca cttaaaaccc taatccagat gaatcgttat cgaaccagat  5340
ataaccaaaa ggggcaaaat tgactcgaaa accctagttc tcgatacacg gctaggtaat  5400
gacaatcgca cacagacaaa tctggttata cagaacttcg aagcaagaaa aaaacgatga  5460
agaatggatc atccaataaa tcgactagac tcaatcttca caggtttatc gatccagcaa  5520
acttaaaaga cggaccttta ttttcaaact ggaatgggac aaaacccgaa actctattgt  5580
cgtaaaatca gatcgcggag acagtaacag aaaaaacatt aaaaagtaat ggaaagacct  5640
aaaccccctga tctaattaca aacaaatcat acctgttctt cgcctgaggg gttcgaaatc  5700
gataagcttg gatcctctag agtcgagaga aattgatgtc tgtagaagaa gaagaacggt  5760
taagagtaga tttgggtgag aaagatgtga aattgttttt ataggcaaag acggagagtc  5820
tattttttga gcaatcagat cgcatattaa atctaacggc tgagatatcg atccgtgtgt  5880
acaataaaat gatgtataaa ccgtcgatct gttttaatcg acggttcata ttagtgatcc  5940
gcgtgatggc agtgatagcc actaagaatc gtcttttgtt ttacatgtgg cgccacaaat  6000
tagggtaatg aagcggcaat atttttggaac tcggaaaata aaattgcgcc atcacattat  6060
ttgaaaattt tcacatgctt ttattttaaa aacccacgaa ttacaagtta caaccgaaaa  6120
agatttataa tatagtgatt tatactaatt ttgtagtagc ttaatgtata ttgatactgg  6180
aaaaacaatg acaatcatat gttagtatta tcaagttatc gtattgatat tgatattgga  6240
acatacaatg ggtattgcct tctttcgacc ataaatatca ccaaatttac aaagtttgtg  6300
tataccaagt tatcaattgt aaatgggatg tcaacatttt aatttccctt tgagaaacta  6360
tagaccacaa gaacacactt caatagataa agtaactatt tacataagag gttttaaaat  6420
cacattaaca aaaataatta ccaaccggca ctcacaaata caaacagagc acacgacatg  6480
tcaaagccac aagtaaattc gttgagtggt ggtttcatta caattgtgtc acttgcagca  6540
caaactatct tgctctggga atcatctcag catcaaagat catgctcact tcaggggaac  6600
ttagtgtatc catgcctcga ctcatatttc tcctcgacat gcatcctgca ggggcgcgcc  6660
atgcccgggc aagcggccgc acaagtttgt acaaaaaagc aggctccgcg gtgactgact  6720
gaaaagcttg tcgacctgca ggtcaacgga tcaggatatt cttgtttaag atgttgaact  6780
ctatggaggt ttgtatgaac tgatgatcta ggaccggata agttcccttc ttcatagcga  6840
acttattcaa agaatgtttt gtgtatcatt ccttgttacat tgttattaat gaaaaaatat  6900
tattggtcat tggactgaac acgagtgtta aatatggacc aggccccaaa taagatccat  6960
tgatatatga attaaataac aagaataaat cgagtcacca aaccacttgc cttttttaac  7020
gagacttgtt caccaacttg atacaaaagt cattatccta tgcaaatcaa taatcataca  7080
aaaatatcca ataacactaa aaaattaaaa gaaatggatc atttcacaat atgttatacg  7140
ataaagaagt tacttttcca agaaattcac tgatttata agcccacttg cattagataa  7200
atggcaaaaa aaacaaaaa ggaaagaaa taaagcacga agaattctag aaaatacgaa  7260
atacgcttca atgcagtggg acccacggtt caattattgc caatttttcag ctccaccgta  7320
tattaaaaa ataaacgat aatgctaaaa aaatataaat cgtaacgatc gttaaatctc  7380
aacggctgga tcttatgacg accgttagaa attgtggttg tcgacgagtc agtaataaac  7440
ggcgtcaaag tggttgcagc cggcacacac gagtcgtgtt tatcaactca aagcacaaat  7500
acttttcctc aacctaaaaa taaggcaatt agccaaaaac aactttgcgt gtaaacaacg  7560
ctcaatacac gtgtcatttt attattagct attgcttcac cgccttagct ttctcgtgac  7620
ctagtcgtcc tcgtcttttc ttcttcttct tctataaaac aatacccaaa gcttcttctt  7680
cacaattcag atttcaattt ctcaaaatct taaaaacttt ctctcaattc tctctaccgt  7740
gatcaaggta aatttctgtg ttccttattc tctcaaaatc ttcgattttg ttttcgttcg  7800
atcccaattt cgtatatgtt ctttggttta gattctgtta gaagacgatt  7860
ttctgggttt gatcgttaga tatcatctta attctcgatt agggtttcat aaatatcatc  7920
cgatttgttc aaataatttg agttttgtcg ataattact cttcgatttg tgatttctat  7980
ctagatctgt tgttagtttc tagttgtgc gatcgaattt gtcgattaat ctgagttttt  8040
ctgattaaca gagatctcca tggctcagac cactctccaa atcacaccca ctggtgccac  8100
cttgggtgcc acagtcactg gtgttcacct tgccacactt gacgatgctg gtttcgctgc  8160
cctccatgca gcctggcttc aacatgcact cttgatcttc cctgggcaac acctcagcaa  8220
tgaccaacag attaccttg ctaaacgctt tggagcaatt gagaggattg gcggaggtga  8280
cattgttgcc atatccaatg tcaaggcaga tggcacagtg cgccagcact ctcctgctga  8340
gtgggatgac atgatgaagg tcattgtggg caacatggcc tggcacgccg actcaaccta  8400
catgccagtc atggctcaag gagctgtgtt cagcagcagaa gttgtcccag cagttggggg  8460
cagaacctgc tttgctgaca tgagggcagc ctacgatgcc cttgatgagg caacccgtgc  8520
tcttgttcac caaaggtctg ctcgtcactc ccttgtgtat tctcagagca agttgggaca  8580
tgtccaacag gccgggtcag cctacatagg ttatggcatg gacaccactg caactcctct  8640
cagaccattg gtcaaggtgc atcctgagac tggaaggccc agcctcttga tcggccgcca  8700
tgcccatgcc atccctggca tggatgcagc tgaatcagag cgcttccttg aaggacttgt  8760
tgactgggcc tgccaggctc ccagagtcca tgctcaccaa tgggctgctg gagatgtggt  8820
tgtgtgggac aaccgctgtt tgctccaccg tgctgagccc tgggatttca agttgccacg  8880
tgtgatgtgg cactccagac tcgctggacg cccagaaact gagggtgctg ccttggttg  8940
agtagttagc ttaatcacct agagctcggt caccagcata ttttttatta atgtactaaa  9000
ttactgtttt gttaaatgca attttgcttt tcgggatttt taatatcaaa atctatttag  9060
aaatacacaa tattttgttg caggcttgct ggagaatcga tctgctatca taaaattac  9120
aaaaaaattt tatttgcctc aattattta ggattggtat taaggacgct taaattttt  9180
gtcgggtcac tacgcatcat tgtgattgag aagtcagacg aatcgaaata ttcgtagtac  9240
tatcgataat ttatttgaaa attcataaga aaagcaaacg ttacatgaat tgatgaaaca  9300
atacaaagac agataaagcc acgcactttt aggatattgg ccgagattac tgaatattga  9360
gtaagatcac ggaattctg acaggagcat gtcttcaatt cagcccaaat ggcagttgaa  9420
atactcaaac cgcccccatat gcaggagcgg atcattcatt gtttgtttgg ttgccttgc  9480
caacatggga gtccaaggtt gcggccgcgc gccgaccag ctttccttgta caaagtggtt  9540
```

```
gcggccgctt aattaaattt aaatgcccgg gcgtttaaac gcggccgctt aattaaggcc   9600
ggcctgcagc aaacccagaa ggtaattatc caagatgtag catcaagaat ccaatgttta   9660
cgggaaaaac tatggaagta ttatgtaagc tcagcaagaa gcagatcaat atgcggcaca   9720
tatgcaacct atgttcaaaa atgaagaatg tacagataca agatcctata ctgccagaat   9780
acgaagaaga atacgtagaa attgaaaaag aagaaccagc cgaagaaaag aatcttgaag   9840
acgtaagcac tgacgacaac aatgaaaaga agaagataag gtcggtgatt gtgaaagaga   9900
catagaggac acatgtaagg tggaaaatgt aagggcggaa agtaacctta tcacaaagga   9960
atcttatccc ccactactta tccttttata ttttccgtg tcattttgc ccttgagttt   10020
tcctatataa ggaaccaagt tcggcatttg tgaaaacaag aaaaaatttg gtgtaagcta  10080
ttttctttga agtactgagg atacaacttc agagaaattt gtaagtttgt agatctccat  10140
gtctccggag aggagaccag ttgagattag gccagctaca gcagctgata tggccgcgt  10200
ttgtgatatc gttaaccatt acattgagac gtctacagtg aacttaggga cagagccaca  10260
aacaccacaa gagtggattg atgatctaga gaggttgcaa gatagatacc cttggttggt  10320
tgctgaggtt gagggtgttg tggctggtat tgcttacgct gggccctgga aggctaggaa  10380
cgcttacgat tggacagttg agagtactgt ttacgtgtca cataggcatc aaaggttggg  10440
cctaggatcc acattgtaca cacatttgct taagtctatg gaggcgcaag gttttaagtc  10500
tgtggttgct gttataggcc ttccaaacga tccatctgtt aggttgcatg aggctttggg  10560
atacacagcc cgggtacat tgcgcgcagc tggatacaag catggtggat ggcatgatgt  10620
tggttttgg caaagggatt ttgagttgcc agctcctcca aggccagtta ggccagttac  10680
ccagatctga ggtaccctga gcttgagctt atgagcttat gagcttagag ctcggatcca  10740
ctagtaacgg ccgccagtgt gctggaattc gcccttgact agataggcgc ccagatcggc  10800
ggcaatagct tcttagcgcc atcccgggtt gatcctatct gtgttgaaat agttgcggtg  10860
ggcaaggctc tctttcagaa agacaggcgg ccaaaggaac ccaaggtgag gtgggctatg  10920
gctctcagtt ccttgtggaa gcgcttggtc taaggtgcag aggtgttagc gggatgaagc  10980
aaaagtgtcc gattgtaaca agatatgttg atcctacgta aggatattaa agtatgtatt  11040
catcactaat ataatcagtg tattccaata tgtactacga tttccaatgt ctttattgtc  11100
gccgtatgta atcggcgtca caaaataatc cccggtgact ttcttttaat ccaggatgaa  11160
ataatatgtt attataattt ttgcgatttg gtccgttata ggaattgaag tgtgcttgcg  11220
gtcgccacca ctcccatttc ataatttac atgtatttga aaaataaaaa tttatggtat  11280
tcaatttaaa cacgtatact tgtaaagaat gatatcttga aagaaatata gtttaaatat  11340
ttattgataa aataacaagt caggtattat agtccaagca aaaacataaa tttattgatg  11400
caagtttaaa ttcagaaata tttcaataac tgattatatc agctggtaca ttgccgtaga  11460
tgaaagactg agtgcgatat tatggtgtaa tacatagcgg ccgggtttct agtcaccggt  11520
taggatccgt ttaaactcga ggctagcgca tgcacataga cacacacatc atctcattga  11580
tgcttggtaa taattgtcat tagattgttt ttatgcatag atgcactcga aatcagccaa  11640
ttttagacaa gtatcaaacg gatgtgactt cagtacatta aaaacgtccg caatgtgtta  11700
ttaagttgtc taagcgtcaa tttgatttac aattgaatat atcctgcccc agccagccaa  11760
cagctcgatt tacagagaac gaatgtcgtg tgatatgtgg aacaaggcaa cgacaacaac  11820
atacatgaat ctcacaatag agtcggggtc gccgagttgt gatgtaatcc atggcatgga  11880
catggtggcc gatcgaaaaa gaaaaagaa atgcatgtat atgtgtgaaa atgagagttt  11940
tttttatcca aataataaaa aaaaattaat tatttacccca aaaaattatt tacatgaccg  12000
atacgtacac tttttttcctt agtaagaaa caccgatttc ttaattacat ttttttatac  12060
atttagaaat tggtttcctt ggaaccgatt tcaaaatgtt cattttttt ttcaaaacca  12120
agttaagaaa tcggttcctt ggaaaacgac ttcttaattg cttttttttt tgttttgttt  12180
taaaattgtt tgtattttta ttttttttgt tattaattgt ctatatttgt gttctgtta  12240
aattgaaaac aatattattt ttcatatgtt gttaattctt aatttcttat gcatatttta  12300
tgttttatca ttttttaaga gttgaaatcc tttgtatttt cattttattt gattattata  12360
atacataatt aaacaacaac ttaattgaaa ttaaaaaata tatatttaac tgacaagttg  12420
acttgaacta aaatatttaa attacaaaat agatatgaaa ttacaaacaa tagaacaaaa  12480
tatttaaatt tgaataataa caacaaaaat tttaaatac aaacaatatg gcataaaatt  12540
aatgttgttg gcctgagcct acacaatggg gggaatgcaa cacatggaac atcattttgg  12600
tttacctgat tcttggatat ccatttttggt gtgtatacga gaggagacat gacaaccttt  12660
agaatttctt ttcattttg ggttgggca aattcttggc ttgtgacatg gtgaccaaca  12720
tgcttcattg cacaatttcc caagtaatca tttgtacatg ttatagatac ttttcagcgt  12780
atacacaaga tgtatgtagt tcctatactc atggtgagca tgcttataaa caacaacatg  12840
agaacaaaac atgtgcattt tttgaaattt gtcacagtca cactacctt catctagctt  12900
gaccatgaaa tttctcacta gttgaatctc tctctccagt taattgtctc ctagactaag  12960
aattgtatgt cgcattaatc gaactcaaga acaatgtgag agtttgcctt tttctgtatg  13020
tctttcaatag ccttgtttaa tactttttgta taaacttcac caaatgtaat cactcttgta  13080
acttctctcc cccctttggtt gaacaatgca ttacacctag tataggttga ttttaccaac  13140
acacattgcc agattttgtg ttttcttgag taccaaatta attaactcag tgtccccatc  13200
gccagccacc atcccatgcg agagtccact tttcttgtgg aatcttccta agctaattaa  13260
ttgttagttc agcttggcct taaaacacac atgacaaata ttttttattat aaaacaaaca  13320
cccagtgata caacaatgaa caacacacat gacaactaca atcattaaa taatacaatt  13380
acaatcaaat aatttgggga gggggtcttc aaaacttgat tcaaggttca ttgtatcatc  13440
gaggtattca cccaaaccct ccaaattcaa agagcttgca gaaactggtg gtggttgtgc  13500
atatgtttat gtgggtgtgt ctacggtgat aacataaaac tcaaggcatg tgaagttgaa  13560
gagtttccca aatatagaaa acatagtaat tatttcctca tcatcttgca gcatacatgc  13620
cctgtactga aaacaatcac caacaaatga tacgggaca                         13659
```

| | |
|---|---|
| SEQ ID NO: 28 | moltype = DNA  length = 14619 |
| FEATURE | Location/Qualifiers |
| misc_feature | 1..14619 |
| | note = Hypothetical sequence of Event 9582.812.9.1 containing 5' genomic flank, 9582 T-strand insert, 3' genomic flank |
| source | 1..14619 |
| | mol_type = other DNA |
| | organism = synthetic construct |

```
SEQUENCE: 28
ttaattataa tgactttatt ataaaatgaa caatttcaaa atcttcacac tccaatttta    60
gattccttt  atatcatttt ctattgagta aaccaccatt tccattctta aaaatgtgag   120
gcctcgcata aaagcatgaa aatggcaaaa acatcccaa  aattacattt tatcagtcca   180
gttaatcaat cgtaaggatc ttagtgtctc tattaacata tgatgaggtg acgtgttaag   240
tgttatgcca tgtacttgtt gatctgtcat gttgcgatca cgtcagcata aatcaaaata   300
aaacttttaa agtacaaaat gataataata ttttatttat ttatttcctc tcgcatccca   360
agatgacagt gaagaaaata atttttgag  accgataatt ctaacataca ctattgactt   420
cagattataa agtactgttc aaatatgaaa tttaaatgct attctagacc aaaatctgaa   480
aattaccaaa atttccctca tgcatcaaac tatattgaat ctcattttaa gacaaaatac   540
aattggaaaa attataaaag ctttatttta aacttagaaa attactataa tatttgaatt   600
tttttctaca actatctaga tttttgttta aaattatcaa ataccctga  gccttttgat   660
caagagtatt attgtcttta gttattgtcg aaaatattat caattgacag tataagttta   720
gtcactattt tgattaaata ttatacttt  tttaaggatt aattattata ctttttataac  780
ttaatccttt ttattataaa atgaacaatt ttaaaatctt ctcactccaa ttttatactc   840
actttatatt cttaataata tgttgtatga gcagaactaa actgaaattc cttaaaaaga   900
aagtcttgat attggtatga gtcttgtgaa taaagaatt  gattgaggga ttccactaaa   960
tcttgccact gacttttat  cattgtctat ttttgtttca gaaatcaaat cagtatatat  1020
actttttat  ctgtccattg ttcaatttcg agcgtctcga tatattatgc gcctaaattg  1080
gacatccgag ttaaaagtta tgaccattcg aatttcccga cacccagtca gcatcatcac  1140
accaaaagtt aggcccgaat agtttgaaat tagaaagctc gcaattgagg tctacaggcc  1200
aaattcgctc ttagccgtac aatattactc accggatcct aaccggtgtg atcatgggcc  1260
gcgattaaaa atctcaatta tatttggtct aatttagttt ggtattgagt aaaacaaatt  1320
cggcgccatg cccgggcaag cggccgcaca agtttgtaca aaaaagcagg ctccgcggtg  1380
actgactgaa aagcttgtcg acctgcaggt caacggatca ggatattctt gtttaagatg  1440
ttgaactcta tggaggtttg tatgaactga tgatctgaga ccggataagt tcccttcttc  1500
atagcgaact tattcaaaga atgttttgtg tatcattctt gttacattgt tattaatgaa  1560
aaaatattat tggtcattgg actgaacacg agtgttaaat atggaccagg ccccaaataa  1620
gatccattga tatatgaatt aaataacaag aataaatcga gtcaccaaac cacttgcctt  1680
ttttaacgag acttgttcac caacttgata caaaagtcat tatcctatgc aaatcaataa  1740
tcatacaaaa atatccaata acactaaaaa attaaaagaa atggataatt tcacaatatg  1800
ttatacgata aagaagttac ttttccaaga aattcactga ttttataagc ccacttgcat  1860
tagataaatg gcaaaaaaaa acaaaaagga aaagaaataa agcacgaaga attctagaaa  1920
atacgaaata cgcttcaatg cagtgggacc cacggttcaa ttattgccaa ttttcagctc  1980
caccgtatat ttaaaaaata aaacgataat gctaaaaaaa tataaatcgt aacgatcgtt  2040
aaatctcaac ggctggatct tatgacgacc gttagaaatt gtggttgtcg acgagtcagt  2100
aataaacggc gtcaaagtgg ttgcagccgg cacacacgag tcgtgtttat caactcaaag  2160
cacaaatact tttcctcaac ctaaaaataa ggcaattagc caaaacaac  tttgcgtgta  2220
aacaacgctc aatacacgtg tcattttatt attagctatt gcttcaccgc cttagcttcc  2280
tcgtgaccta gtcgtcctcg tcttttcttc ttcttcttct ataaaacaat acccaaagct  2340
tcttcttcac aattcagatt tcaatttctc aaaatcttaa aaactttctc tcaattctct  2400
ctaccgtgat caaggtaaat ttctgtgttc cttattctct caaaatcttc gattttgttt  2460
tcgttcgatc ccaatttcgt atatgttctt tggtttagat tctgttaatc ttagatcgaa  2520
gacgattttc tgggtttgat cgttagatat catcttaatt ctcgattagg gtttcataaa  2580
tatcatccga tttgttcaaa taatttgagt tttgtcgaat aattactctt cgatttgtga  2640
tttctatcta gatctggtgt tagtttctag tttgtgcgat cgaatttgtc gattaatctg  2700
agtttttctg attaacgagg atctccatgg agaacaatat ccagaaccag tgtgtcccat  2760
acaattgcct caacaatcct gaagttgaga tcctcaacga agagaggagc actggacgcc  2820
ttccccttga catctccctc tccctcacaa ggttcctttt gtctgagttt gttcctggtg  2880
tgggtgtggc ctttggcctc tttgacctca tctgggct   catcaccca  tctgattgga  2940
gcctcttcct tctccagatt gaacaattga ttgagcagag gattgagacc cttgaaagga  3000
acagagccat caccacactt cgtgccttg  ctgacagcta tgaaatctac attgaagcac  3060
tccgtgagtg ggaagccaat cccaacaatg ctcaactccg tgaagatgtg aggattcgct  3120
tgccaacac  agatgacgct ttgatcacag ccatcaacaa tttcacccctc accagctttg  3180
agatccctt  gctctcagtc tatgttcaag ctgcaaacct ccacttgagc ttgcttaggg  3240
atgctgtgtc cttcggacaa ggttgggac  ttgacatagc cactgtcaac aatcactaca  3300
acagactcat caacttgatt catcgctaca ccaaacattg cttggacacc tacaatcaag  3360
gattggaaga acctcagagc accaacactc gccaatgggc aaggttcaac cagtttgaa   3420
gggatctcac actcactgtg cttgacatag ttgctctctt ccccaactat gattgttcga   3480
cctacccaat tcaaaccagc tcccaactta caagggaaat ctacacctcc tcagtcattg   3540
aggacagccc agtttctgcc aacatacccaa atgggttcaa  ccgtgctgag tttggtgtca  3600
gaccacccca tctcatggac ttcatgaact ccttgtttgt gactgccgag actgttaggt   3660
cccaaactgt gtggggaggc caccttgtta gctcccgcaa caccgctggc aaccgcatca   3720
acttcccatc ctatggggtt ttcaatcctg gtggagccat ctggattgca gatgaggacc   3780
caaggccttt ctacagaacc ttgtcagatc ctgtctttgt cagaggaggc tttggcaatc   3840
cacactatgt tcttggtttg agggagtgg  cttttcagca gactggcacc aatcacaccc   3900
gcacattcag aaacagcggc accattgaca gccttgatga gatcccacct caagacaaca   3960
gcggagcacc ctggaacgac tactccatg  tgctcaatca tgtcaccttt gtgcgctggc   4020
ctggtgagat cagcggttca gattcttgga gagcaccaat gttctcatgg acccatcgct   4080
ctgccacacc cacaaacacc attgatccag agagaatcac ccagattccc ttggtgaagg   4140
cacacacact tcagtctgga accacagttg tcagagggcc tggttcact  ggtgagaca    4200
ttctcagacg cacctctgga gggccatttg cttaccacat tgtcaacatc aatgggcaac   4260
ttccccagcg ttacgtgcc  agaatccgct atgcttccac cactcaacttg agaatctatg  4320
tcacagttgc tggtgaaagg atctttgctg tcagttcaa caagacaatg gacactggtg   4380
atccattgac attccagtca ttctcctatg ccaccatcaa cactgcattc acctttccaa   4440
tgagccagtc cagcttcaca gtgggtgcag atacctcag  ctccggcaat gaggtgtaca   4500
ttgaccgctt tgagttgatt ccagtgactg ccacacttga ggctgagtct gacttggagc   4560
gtgctcagaa ggccgtgaat gctctcttca cctcttcaaa tcagattggg ctcaagacag   4620
atgtgactga ctaccatata gaccgtgttt ccaatcttgt tgagtgcctc tctgatgagt   4680
```

```
tctgcttgga tgagaagaaa gagttgtcag agaaggtcaa gcacgccaag aggctctctg   4740
atgagaggaa cttgcttcaa gatcccaact tcagagggat caaccgtcaa ttggatcgtg   4800
gatggagggg atcaactgac ataaccattc aaggaggtga cgatgtgttc aaggagaact   4860
atgtcacact cttggggacc tttgatgagt gctacccaac ataccttac cagaagatag    4920
acgaaagcaa gctcaaggcc tacacaagat accagttgaa aggttacatt gaggactctc   4980
aagaccttga aatctacctc atcagataca acgccaaaca tgagacagtc aatgtgcctg   5040
ggactggttc actctggcca cttttcagccc caagccccat tggcaagtgt gcccatcact   5100
cacatcactt ctccttggac atagatgttg gctgcactga cttgaatgag gaccttggtg   5160
tgtgggtgat cttcaagatc aagacccaag atggccatgc aaggttgggc aatcttgagt   5220
ttcttgaaga gaaaccactt gttggagaag cccttgccag agtgaagagg gctgagaaga   5280
aatggaggga caagagagag aagttggagt gggaaacaaa cattgtgtac aaagaagcca   5340
aagaatcagt tgatgctttg tttgtgaact cccaatatga taggctccaa gctgacacca   5400
acatagcaat gattcatgct gcagacaaaa gggttcacag cattcgtgaa gcatacttc    5460
ctgaactctc agtgattcct ggggtcaatg ctgcaatctt tgaagagctt gaaggacgca   5520
tcttcactgc cttctccttg tatgatgcaa ggaatgtcat caagaatggt gacttcaaca   5580
atggcctttc ctgctggaat gtgaaagggc acgtggatgt tgaagagcag aacaatcacc   5640
gctctgtcct tgttgtccct gagtgggaag ctgaagtttc acaagaagtt cgtgtctgcc   5700
ctggtcgtgg ctacattctt cgtgtgactg cttacaaaga aggctatgga gaaggttgtg   5760
tcaccatcca cgagatagag aacaatactg atgaattgaa gttcagcaac tgtgttgagg   5820
aagaggtcta cccaaacaat actgtcactt gcaatgacta cactgcaact caagaagagt   5880
atgagggcac ttacacttct cgcaaccgtg gctatgatgg agcctatgag agcaactcat   5940
ctgtgcctgc tgactatgct tcagcctatg aagagaaggc atacactgat ggaaggcgtg   6000
acaatccttg tgaaagcaac agaggctatg gggactacac accctccca gctggctatg    6060
tgaccaaaga gttggagtac tttcctgaaa ctgacaaggt ttggattgag ataggagaaa   6120
ctgaaggcac attcatagtt gactctgtgg agctttttgct catggaagag tgagtagtta   6180
gcttaatcac ctagagctcg gtcaccagca taattttat taatgtacta aattactgtt     6240
ttgttaaatg caattttgct ttctcggat tttaatatca aaatctattt agaaatacac     6300
aatattttgt tgcaggcttg ctggagaatc gatctgctat cataaaaatt acaaaaaat    6360
tttatttgcc tcaattattt taggattggt attaaggacg cttaaattat ttgtcgggtc    6420
actacgcatc attgtgattg agaagatcag cgatacgaaa tattcgtagt actatcgata   6480
atttatttga aaattcataa gaaaagcaaa cgttacatga attgatgaaa caatacaaag    6540
acagataaag ccacgcacat ttaggatatt ggccgagatt actgaatatt gagtaagatc    6600
acggaatttc tgacaggagc atgtcttcaa ttcagcccaa atggcagttg aaatactcaa    6660
accgccccat atgcaggagc ggatcattca ttgtttgttt ggttgccttt gccaacatgg    6720
gagtccaagg ttgcggccgc gcgccgaaaa caactttgta tacaaaagtt gccgcggtga    6780
ctgactgaac taaacccaga aggtaattat ccaagatgta gcatcaagaa tccaatgttt    6840
acgggaaaaa ctatgcaagt attatgtaag ctcagcaaga agcagatcaa tatgcggcac   6900
atatgcaacc tatgttcaaa aatgaagaat gtacagatac aagatcctat actgccagaa   6960
tacgaagaag aatacgtaga aattgaaaaa gaagaaccag gcgaagaaaa gaatcttgaa    7020
gacgtaagca ctgacgacaa caatgaaaag aagaagataa ggtcggtgat tgtgaaaagag   7080
acatagagga cacatgtaag gtggaaaatg taagggcgga aagtaacctt atcacaaagg    7140
aatcttatcc cccactactt atcctttat attttccgt gtcatttttg cccttgagtt      7200
ttcctatata aggaaccaag ttcggcattt gtgaaaacaa gaaaaaattt ggtgtaagct    7260
attttctttg aagtactgag gatacaactt cagagaaatt tgtaagtttg tagatccaac    7320
aatgacaac aatcccaaca tcaacagtgt cattccttac aactgcctga gcaaccctga    7380
ggttgaggtg ctgggtggag aacggattga gactggttac acacctatcg acatctcgtt    7440
gtcacttacc caattccttt tgtcagagtt cgtgcccggt gctggattcg tgctttggact  7500
tgtcgatatc atttgggaa tcttttggtcc ctctcaatgg gacgccttc ttgtacagat     7560
agagcagtta attaaccaaa gaatagaaga attcgctagg aaccaagcca tctcaaggtt   7620
agaaggcctc agcaaccttt accagattta cgcagaatct tttcgagagt gggaagcaga    7680
cccgaccaat cctgccttaa gagaggaagt gcgcattcaa ttcaatgaca tgaacagcga    7740
gctgacgacc gcaattccgc tcttcgccgt tcagaattac caagttcctc tttttatccgt    7800
gtacgtgcag gctgccaacc tgcacttgtc ggtgctccgc gatgtctccg tgttcggaca   7860
acggtgggc tttgatgccg caactatcaa tagtcgttat aatgatctga ctaggctat     7920
tggcaactat accgattatg ctgttcgctg gtacaacacg ggtctcgaac gtgtctgggg   7980
accggattct agagattggg tcaggtacaa ccagttcagg cgagagttga cactaactgt   8040
cctagacatt gtcgctctct ttcccaacta cgactctagg cgctacccaa tccgtactgt   8100
gtcacaattg acccgggaaa tctacacaaa cccagtcctc gagaacttcg acggtagctt   8160
tcgaggctcg gctcagggca tagagagaag catcaggtct ccacacctga tggacatatt   8220
gaacagtatc acgatctaca ccgatgcgca ccgcgttat tactactggt cagggcatca   8280
gatcatggca tcacccgttg ggttctctgg accagaattc actttccac tttacgggac    8340
tatgggcaat gcagctccac aacaacgtat tgttgctcaa ctcggtcagg gcgtgtatag    8400
aaccttgtcc agcactctat ataggagacc tttcaacatc ggcatcaaca atcaacaatt   8460
gtctgtcgtt gacgggacag aaatttgcct atggaacctcc tcaaatctgc catccgctgt   8520
ctacagaaag agcggaacag ttgatagctt ggatgagatc cctccacaga acaacgt       8580
tccacctagg caagggttta gccatcgcct agccatgtg tccatgttcc gttcaggctt    8640
tagtaatagc agcgttagta tcatcagagc tccgatgttc tcttggatac atcgtagtgc   8700
tgagtttaac aacataattg catccgatag cattactgca tcaagggaa                8760
cttttctttt aatggttctg tcattcagg accaggattc actggaggcg acttggttag    8820
gctgaattct tccggcaaca acatccagaa tagagggtat attgaagtgc ccattcactt   8880
cccatcgaca tctaccagat atcgtgttcg tgtaaggtat gcctctgtta cccctattca    8940
cctcaacgtc aattggggta attcctccat cttttccaat acagtaccag cgacagctac   9000
atccttggat aatctccaat ctagcgattt cggttacttc gaaagtgcca atgccttcac   9060
ctcttcccta ggtaacatag taggtgttag aaatttctcc ggaaccgccg gagtgataat   9120
cgaccgcttc gaattcattc ccgttactgc aacgctcgag gcagagtctg acttggaaag   9180
agcacagaag gcggtgaatg ctctgttcac ttcgtccaat cagattgggc tcaagacaga   9240
tgtgactgac tatcacatcg atcgcgtttc caaccttgtt gagtgcctct ctgatgagtt   9300
ctgtttggat gagaagaagg agttgtccga gaaggtcaaa catgctaagc gacttagtga   9360
tgagcggaac ttgcttcaag atcccaactt cgcgggatc aacaggcaac tagatcgtgg    9420
```

```
atggagggga agtacggaca tcaccattca aggaggtgat gatgtgttca aggagaactg    9480
tgttacgctc ttgggtacct ttgatgagtg ctatccaaca tacctgtacc agaagataga    9540
tgaatcgaaa ctcaaagcct acacaagata ccagttgaga ggttacatcg aggacagtca    9600
agaccttgag atctacctca tcagatacaa cgccaaacat gagacagtca atgtgcctgg    9660
gacgggttca ctctggccac tttcagcccc aagtccccat ggcaagtgtg cccatcactc    9720
acaccacttc tccttggaca tagacgttgg ctgtaccgac ctgaacgaag acctcggtgt    9780
gtgggtgatc ttcaagatca agactcaaga tggccatgcc aggctaggca atctggagtt    9840
tctagaaagg aaaccacttg ttggagaagc cctcgctaga gtgaagaggg ctgagaagaa    9900
gtggagggac aagagagaga agttggaatg ggaaacaaac attgtgtaca aagaagccaa    9960
agaaagcgtt gacgctctgt ttgtgaactc tcagtatgat aggctccaag ctgataccaa   10020
catagctatg attcatgctg cagacaaacg cgttcatagc attcgggaag cttaccttcc   10080
tgaacttagc gtgattccgg gtgtcaatgc tgctatcttt gaagagttag aagggcgcat   10140
cttcactgca ttctccttgt atgatgcgag gaatgtcatc aagaatggtg acttcaacaa   10200
tggcctatcc tgctggaatg tgaaagggca cgtagatgta gaagaacaga acaatcaccg   10260
ctctgtcctt gttgttcctg agtgggaagc agaagtttca caagaagttc gtgtctgtcc   10320
tggtcgtggc tacattcttc gtgttaccgc gtacaaagaa ggatacggag aaggttgcgt   10380
caccatacac gagattgaga acaacaccga cgagctgaag ttcagcaact gcgtcgagga   10440
ggaagtctac ccaaacaaca ccgtaacttg caatgactac actgcgactc aagaggagta   10500
tgagggtact tacacttctc gcaatcgagg atacgatgga gcctatgaga gcaactcttc   10560
tgtacccgct gactatgcat cagcctatga ggagaaggct tacaccgatg gacgtaggga   10620
caatccttgc gaatctaaca gaggctatgg ggactacaca ccgttaccag ccggctatgt   10680
caccaaagag ttagagtact ttccagaaac cgacaagaaa tggattgaga ttggagaaac   10740
ggaaggaaca ttcattgttg atagcgtgga gttacttctg atggaggaat gagtagttag   10800
cttaatcacc tagagctcgg ttacctatca aaatctattt agaaatacac aatattttgt   10860
tgcaggcttg ctggagaatc gatctgctat cataaaaatt acaaaaaaat tttatttgcc   10920
tcaattattt taggattggt attaaggacg cttaaattat ttgtcgggtc actacgcatt   10980
attgtgattg agaagatcag cgatacgaaa tattcgtagt actatcgata atttatttga   11040
aaattcataa gaaaagcaaa cgttacatga attgatgaaa caatacaaag acagataaag   11100
ccacgcacat ttaggatatt ggccgagatt actgaatatt gagtaagatc acggaatttc   11160
tgacaggage atgtcttcaa ttcagcccaa atggcagttg aaatactcaa accgcccat   11220
atgcaggagc ggatcattca ttgtttgttt ggttgccttt gccaacatgg gagtccaagg   11280
ttgcggccgc gcgccgaccc agctttcttg tacaaagtgg ttgcggccgc ttaattaaat   11340
ttaaatgccc gggcgtttaa acgcggccgc ttaattaagg ccggcctgca gcaaacccag   11400
aagtaatta tccaagatgt agcatcaaga atccaatgtt tacgggaaaa actatggaag   11460
tattatgtaa gctcagcaag aagcagatca atatgcggca catatgcaac ctatgttcaa   11520
aaatgaagaa tgtacagata caagatccta tactgccaga atacgaagaa gaatacgtag   11580
aaattgaaaa agaagaacca ggcgaagaaa agaatcttga agacgtaagc actgacgaca   11640
acaatgaaaa gaagaagata aggtcggtga ttgtgaaaga gacatagagg acacatgtaa   11700
ggtggaaaat gtaagggcgg aaagtaacct tatcacaaag gaatcttatc ccccactact   11760
tatccttta tattttccg tgtcatttt gcccttgagt tttcctatat aaggaaccaa   11820
gttcggcatt tgtgaaaaca agaaaaaatt tggtgtaagc tattttcttt gaagtactga   11880
ggatacaact tcagagaaat ttgtaagttt gtagatctcc atgtctccgg agaggagacc   11940
agttgagatt aggccagcta cagcagctga tatggccgcg gtttgtgata tcgttaacca   12000
ttacattgag acgtctacag tgaactttag gacagagcca caaacaccac aagagtggga   12060
tgatgatcta gagaggttgc aagatagata cccttggttg gttgctgagg ttgagggtgt   12120
tgtggctggt attgcttacg ctgggccctg gaaggctagg aacgcttacg attggacagt   12180
tgagagtact gtttacgtgt cacataggca tcaaaggttg ggcctaggat gtacccattgta   12240
cacacatttg cttaagtcta tggaggcgca aggttttaag tctgtggttg ctgtttatagg   12300
ccttccaaac gatccatctg ttaggttgca tgaggctttg ggatacacag cccggggtac   12360
attgcgcgca gctggataca agcatggtgg atggcatgat gttggttttt ggcaaaggga   12420
ttttgagttg ccagctcctc caaggccagt taggccagtt acccagatct gaggtaccct   12480
gagcttgagc ttatgagctt atgagcttag agctcggatc cactagtaac ggccgccagt   12540
gtgctggaat tcgcccttga ctagataggc gcccagatcg gcggcaatag cttcttagcg   12600
ccatcccggg ttgatcctat ctgtgttgaa atagttgcgg tgggcaaggc tctcttttcag   12660
aaagacaggc ggccaaagga acccaaggtg aggtgggcta tggctctcag ttcctttgtgg   12720
aagcgcttgg tctaaggtgc agaggtgtta gcgggatgaa gcaaaagtgt ccgattgtaa   12780
caagatatgt tgatcctacg taaggatatt aaagtatgta ttcatcacta ataatcag   12840
tgtattccaa tatgtactac gatttccaat gtctttattg tcgccgtatg taatcggcgt   12900
cacaaaataa tccccggtga cttttctttta atccaggatg aaatagatg ttattataat   12960
ttttgcgatt tggtccgtta taggaattga agtgtgcttg cggtcgccac cactcccatt   13020
tcataatttt acatgtattt gaaaaataaa aatttatggt attcaattta aacacgtata   13080
cttgtaaaga atgatatctt gaagaaaata tagtttaaat atttattgat aaaataacaa   13140
gtcaggtatt atagtccaag caaaaacata aatttattga tgcaagttta aattcagaaa   13200
tatttcaata actgattata tcagctgata cattgccgta gatgaaagac tgagtgcgat   13260
attatggtgt aatacatagc ggccgggttt ctagtcaccg gttaggatcc gtttaaactc   13320
gaggctagcg catgcacata gacacacaca tcatctcatt gatgcttggt aataattgtc   13380
attagattgt tttatgcat agatgcactc gaaatcagcc aattttagac aagtatcaaa   13440
cggatgtgac ttcagtacat taaaaacgtc cgcaatgtgc cattggcaac aacctctgat   13500
gccgtaactt tctttgttg gttcagaaat ccaaccgtta tggataatc taaatctca   13560
tacttcatct ttccacaaaa gcacaaattc tcctactagt aggctttaga tgtgttttat   13620
atctctaaaa gcattaaata tttttttattt ttcattcatt atttcataaa agatagtaaa   13680
gtccccttg tctgcagaga aaatggtgaa aaagaaaat aaataaa ataataaagt   13740
gatgtaacat tcatatttt atattatatt ttaattcaaa aactttaatc tcatgtgact   13800
tttatttttc ttttcactac cgaacggagc ctgaagaaat atagcattac tcaaccgtta   13860
tattgctgaa aaattctag taatgaccat ttgaatttct cgagagcttc cgttgttcaa   13920
tttctagcgt ctctatatgt gatgcggcag aatcggaccct ccgagtgaaa agttatgacc   13980
atttgaattt ttcgaaagct tccgttgttt aattcgagc gtctcgatat attatgcggc   14040
tgaatcggac ctccgagtga aaagttatga tcatttgaat tgctcaagag cttccattgt   14100
tcaatttcga acgtctcgat atattatgcg catgaatcag acatccgagt gaaaagttat   14160
```

```
gaccatttga attgctcaag agtttccatt gccccatttt gaacgtctcg atatattatg  14220
cgcctgaatc ggacttccga gttaaatgtt attctcaaga gcttttgttg ttcaatttca  14280
agcgtctcga tatattatgc acctgaatcg gatctccgag tgaaatgtta gttccatttg  14340
aattggtcaa gtgcttccat agcatggtgg gcgagagtac caccctccac caaacaaacc  14400
cactctctat attcctattt ctgtatactt ctctagacaa cgttagtagt aacacaacca  14460
ctctcattag ccttaaccga cccagagaaa acacgcatcg gttaatgcta ttcctttctc  14520
tgaaatcgct tcgaagacaa gaaaagaatt aataaccaaa agaaaccgca cctcatacca  14580
gaaatagctt acatgcctaa cgattttctt tgcttttaa                         14619
```

```
SEQ ID NO: 29          moltype = DNA   length = 15294
FEATURE                Location/Qualifiers
misc_feature           1..15294
                       note = Expected sequence of soybean event 9582.814.19.1
source                 1..15294
                       mol_type = other DNA
                       organism = synthetic construct
SEQUENCE: 29
ttaacaatga ccaagattta tgctatatag aagacttgga gggcttaagg ctatgatata   60
ttatggatga tatggttctg atttgtgtag tttcgaagga tcaaatcaac catttgttgg  120
tacaatggga agaaaaaatg ttttcatcat tccactctat tgaaaagat ccaacaattg   180
taacaccccg acgaatcaca ccggaaagag aagaatccaa agattgtgta ggtatgagac  240
tgtatagttg atgaaaactt aaaaaaatta attggtacta cttataccaa caagatgcat  300
atatttttcg atagcctatc acataagaac ttcatagtta agggtgctta acttggagta  360
gttatgaaat gagtgacctt ttaaaataat tattgtctta ggttattgta tgaaaataaa  420
aaataataat aaatatacat aaaaaataat aattttataa aattaacctt atattatcat  480
taatttattt ttagattttg ttattcatta ttaatatatg aggtataaat gaaaaatata  540
attaatgtca cattaaaaaa ttaaaatgat aattattttg aaacaaatta tttatttta   600
tacgacaatt ataatagaaa tttgagagta aaaaaaaatt gaaaattcat aaaatatatg  660
aatatattca tttctcctat ccgtcaaata aatctgctcc ataatttatc taagcattgg  720
tcttgtagtt cagagtaata aaattttagc aattaatagt tagtacagat acatttaaag  780
aaataaatata ttttagcaac tagaagttta taaaaagttt taaattataa agacttatat  840
ataaatttag taaaactaga tggatgtccc aagtaatttt tatataacta ttctcgtaca  900
acattaatga aaatcttgtt tctattattt atatgtatat tattatttta ttttggaaca  960
atatgggatt aaaaactctt ataaattaaa tcttagaata agttttccta acatgttttt 1020
tttatggatg tttcctaac atgtttggtt atcttagttt tgctttaatt ttgtcggatt  1080
attttttggac tttattaggt aattttgata aaactttag ttgatgttag tagtttactc  1140
ttacataatg atttgatatt gaatgtgtat aattggaagg caataaatga agatcaagcg 1200
tacaagagtt cgccaatcaa gaggatttga agagagtaaa atattatgcg aagtcccatg 1260
tgaagaaaat ccaaccattg gaataaaaaa taagttttt tcttttggaat tgctaatgct 1320
acagcactta ttggtacttg tcctaaaaat gaaactctag ctatatttag cacttgatat 1380
tcatgaatca aacttctcta tgaaataacc gcggtgcgca tcggtgcctg ttgatcccgc 1440
gcaagttggg atcttgaagc aagttccgct catcactaag tcgcttagca tgtttgacct 1500
tctcggacaa ctccttcttc tcttttaattg atcaacagtc agcatcatca caccaaaagt 1560
taggcccgaa tagtttgaaa ttagaaagct cgcaattgag gtctacaggc caaattcgct 1620
cttagccgta caatattact caccggatcc taaccggtgt gatcatgggc cgcgattaaa 1680
aatctcaatt atatttggtc taatttagtt tggtattgag taaaacaaat tcggcgccat 1740
gcccgggcaa gcggccgcac aagtttgtac aaaaaagcag gctccgcgt gactgactga 1800
aaagcttgtc gacctgcagg tcaacggatc aggatattct tgtttaagat gttgaactct 1860
atggaggttt gtatgaactg atgatctagg accggataag ttcccttctt catagcgaac 1920
ttattcaaag aatgttttgt gtatcattct tgttacattg ttattaatga aaaaatatta 1980
ttggtcattg gactgaacac gagtgttaaa tatggaccag gccccaaata agatccattg 2040
atatatgaat taaataacaa gaataaatcg agtcaccaaa ccacttgcct tttttaacga 2100
gacttgttca ccaactgat acaaaagtca ttatcctatg caaatcaata atcatacaaa 2160
aatatccaat aacactaaaa aattaaaaga aatggataat ttcacaatat gttatacgat 2220
aaagaagtta ctttttccaag aaattcactg attttataag cccacttgca ttagataaat 2280
ggcaaaaaaa aacaaaaagg aaaagaaata aagcacgaag aattctagaa aatacgaaat 2340
acgcttcaat gcagtgggac ccacggttca attattgcca attttcagct ccaccgtata 2400
tttaaaaaat aaaacgataa tgctaaaaaa atataaatcg taacgatcgt taaatctcaa 2460
cggctggatc ttatgacgac cgttagaaat tgtggttgtc gacgagtcag taataaacgg 2520
cgtcaaagtg gttcagccgg cacacacga gtcgtgttta tcaactcaaa gcacaaatac 2580
ttttcctcaa cctaaaaata aggcaattag ccaaaaacaa ctttgcgtgt aaacaacgct 2640
caatacacgt gtcattttat tattagctat tgcttcaccg ccttagcttt ctcgtgacct 2700
agtcgtcctc gtctttttctt cttcttcttc tataaaacaa tacccaaagc ttcttcttca 2760
caattcagat ttcaatttct caaaatctta aaaacttct ctcaattctc tctaccgtga 2820
tcaaggtaaa tttctgtgtt cctatttctc tcaaaatctt cgattttgtt ttcgttcgat 2880
cccaatttcg tatatgttct ttggtttaga ttctgttaat cttagatcga agacgatttt 2940
ctgggtttga tcgttagata tcatcttaat tctcgattag ggttcataa atatcatccg 3000
atttgtttcaa ataatttgag tttttgtcgaa taattactct tcgattttgtg attctatct 3060
agatctggtg ttagtttcta gtttgtgcga tcgaatttgt cgattaatct gagtttttct 3120
gattaacaga gatctccatg gagaacaata tccagaacca gtgtgtccca tacaattgcc 3180
tcaacaatcc tgaagttgag atcctcaacg aagagaggag cactgacgc cttcccttg   3240
acatctccct ctccctcaca aggttccttt tgtctgagtt tgttcctggt gtgggtgtgg 3300
cctttggcct ctttgacctc atctgggct tcatcacccc atctgattgg agcctcttcc 3360
ttctccagat tgaacaattg attgagcaga gattgaacac cctgaaaagg aacagagcca 3420
tcaccacact tcgtgccctt gctgacagct atgaaatcta cattgaagca ctccgtgagt 3480
gggaagccaa tccccaacaat gctcaactcc gtgaagatgt gaggattcgc tttgccaaca 3540
cagatgacgc ttttgatcaca gccatcaaca atttcacccct caccagctt gagatcccctt 3600
tgctctcagt ctatgtccaa gctgcaaacc tccacttgag cttgcttagg gatgctgtgt 3660
ccttcggaca aggttgggga cttgacatag ccactgtcaa caatcactac aacagactca 3720
```

```
tcaacttgat tcatcgctac accaaacatt gcttgacac ctacaatcaa ggattggaga    3780
acctcagagg caccaacact cgccaatggg caaggttcaa ccagtttaga agggatctca    3840
cactcactgt gcttgacata gttgctctct tccccaacta tgatgttcgc acctacccaa    3900
ttcaaaccag ctcccaactt acaagggaaa tctacacctc ctcagtcatt gaggacagcc    3960
cagtttctgc caacatacc aatggtttca accgtgctga gtttggtgtc agaccacccc    4020
atctcatgga cttcatgaac tccttgtttt tgactgccga gactgttagg tcccaaactg    4080
tgtggggagg ccaccttgtt agctcccgca acaccgctgg caaccgcatc aacttcccat    4140
cctatggggt tttcaatcct ggtggagcca tctggattgc agatgaggac ccaaggcctt    4200
tctacagaac ctttgtcagat cctgtctttg tcagaggagg cttttggcaat ccacactatg    4260
ttcttggttt gaggggagtg gcttttcagc agactggcac caatcacacc cgcacattca    4320
gaaacagcgg caccattgac agccttgatg agatcccacc tcaagacaac agcggagcac    4380
cctggaacga ctactcccat gtgctcaatc atgtcacctt tgtgcgctgg cctggtgaga    4440
tcagcggttc agattcttgg agagcaccaa tgttctcatg gacccatcgc tctgccacac    4500
ccacaaacac cattgatcca gagagaatca cccagattcc cttggtgaag gcacacacac    4560
ttcagtctgg aaccacagtt gtcagagggc ctgggttcac tggtggagac attctcagac    4620
gcacctctgg agggccattt gcttacacca ttgtcaacat caatgggcaa cttccccagc    4680
gttaccgtgc cagaatccgc tatgcttcca ccactaactt gagaatctat gtcacagttg    4740
ctggtgaaag gatctttgct ggtcagttca acaagacaat ggacactggt gatccattga    4800
cattccagtc attctcctat gccaccatca acactgcatt caccttttcca atgagccagt    4860
ccagcttcac agtgggtgca gatacccttca gctccggcaa tgaggtgtac attgaccgct    4920
ttgagttgat tccagtgact gccacacttg aggctgagtc tgacttggag cgtgctcaga    4980
aggccggtga tgctctcttc acctcttcaa atcagattgg gctcaagaca gatgtgactg    5040
actaccatat agaccgtgtt tccaatcttg ttgagtgcct ctctgatgag ttctgcttga    5100
atgagaagaa agagttgtca gagaaggtca agcacgccaa gaggctctct gatgagagga    5160
acttgcttca agatcccaac ttcagaggga tcaaccgtca attggatcgt ggatgggggg    5220
gatcaactga cataaccatt caaggaggtg acgatgtgtt gaggagaac tatgtcacac    5280
tcttggggac ctttgatgag tgctacccaa catacctttta ccagaagata gacgaaagca    5340
agctcaaggc ctacacaaga taccagttga gaggttacat tgaggactct caagaccttg    5400
aaatctacct catcagatac aacgccaaac atgagacagt caatgtgcct gggactggtt    5460
cactcgtgcc acttttcagcc ccaagcccca ttggcaagtg tgcccatcac tcacatcact    5520
tctccttgga catagatgtt ggctgcactg acttgaatga ggaccttggt gtgtgggtga    5580
tcttcaagat caagacccaa gatgccatg caaggtttggg caatcttgag tttcttgaag    5640
agaaaccact tgttggagaa gcccttgcca gagtgaagag ggctgagaag aaatggaggg    5700
acaagagaga aagttggag tgggaaacaa acattgtgta caaagaagcc aaagaatcag    5760
ttgatgcttt gtttgtgaac tccaaatatg ataggctcca agctgacacc aacatagcaa    5820
tgattcatgc tgcagacaaa agggttcaca gcattcgtga agcataccttt cctgaactct    5880
cagtgattcc tgggtcaat gctgcaatct tgaagagct tgaaggacgc atcttcactg    5940
ccttctcctt gtatgatgca aggaatgtca tcaagaatgg tgacttcaac aatggccttt    6000
cctgctgaa tgtgaaaggg cacgtggatg ttgaagagca gaacaatcac cgctctgtcc    6060
ttgttgtccc tgagtgggaa gctgaagttt cacaagaagt tcgtgtctgc cctggtcgtg    6120
gctacattct tcgtgtgact gcttacaaag aaggctatgg agaaggttgt gtcaccatcc    6180
acgagatag gaacaatact gatgaattga agttcagcaa ctgtgttgag gaagaggtct    6240
acccaaacaa tactgtcact tgcaatgact acactgcaac tcaagaagag tatgagggca    6300
cttacacttc tcgcaaccgt ggctatgatg agcctatga gagcaactca tctgtgcctg    6360
ctgactatgc ttcagcctat gaagagaagg catacactga tggaaggcgt gacaatcctt    6420
gtgaaagcaa cagaggctat ggggactaca cacccctccc agctggctat gtgaccaaag    6480
agttgagta ctttcctgaa actgacaagg tttggattga gatatggagaa actgaaggca    6540
cattcatagt tgactctgtg gagcttttgc tcatggaaga gtgagtagtt agcttaatca    6600
cctagagctc ggtcaccagc ataatttttta ttaatgtact aaattactgt tttgttaaat    6660
gcaatttgtc tttctcggga ttttaatatc aaaatctatt tagaaataca caatatttttg    6720
ttgcagcttt gctggagaat cgatctgcta tcataaaaat tacaaaaaaa ttttattttgc    6780
ctcaattatt ttaggattgg tattaaggac gcttaaatta tttgtcgggt cactacgcat    6840
cattgtgatt gagaagatca gcgatacgaa atattcgtag tactatcgat aatttatttg    6900
aaaattcata agaaaagcaa acgttacatg aattgatgaa acaatacaaa gacagataaa    6960
gccacgcaca tttaggatat tggccgagat tactgaatat tgataagat cacggaatttt    7020
ctgacaggag catgtcttca attcagccca aatggcagtt gaaatactca aaccgcccca    7080
tatgcaggag cggatcattc attgtttgtt tggttgcctt tgccaacatg ggagtccaag    7140
gttgcggccg cgcgccgaaa caactttgt atacaaaagt tgccgcgtg actgactgaa    7200
ctaaacccag aagtaatta tccaagatgt agcatccaaga atccaatgtt tacgggaaaa    7260
actatgaag tattatgtaa gctcagcaag aagcagatca atatgcggca catatgcaac    7320
ctatgttcaa aaatgaagaa tgtacagata caagatccta tactgccaga atacgaagaa    7380
gaatacgtag aaattgaaaa agaagaacca ggcgaagaaa agaatcttga agacgtaagc    7440
actgacgaca acaatgaaaa gaagaagata aggtcggtga ttgtgaaaga gacatagagg    7500
acacatgtga ggtggaaaat gtaagggcgg aaagtaactt tatcacaaag gaatcttatc    7560
ccccactact tatccttttta tattttttccg tgtcatttttt gcccttgagt tttcctatat    7620
aaggaaccaa gttcggcatt tgtgaaaaca agaaaaaatt tggtgtaagc tattttcttt    7680
gaagtactga ggatacaact tcagagaaat ttgtaagttt gtagatccaa caatggacaa    7740
caatcccaac atcaacgagt gcattcctta caactgcctg agcaaccctg aggttgaggt    7800
gctgggtgga gaacggattg agactggtta cacaccttac gacatctctgt tgtcacttac    7860
ccaattcctt ttgtcagagt tcgtgccggg tgctggattc gtgcttggac ttgtcgatat    7920
catttgggga atctttggtc cctctcaatg ggacgccttt cttgtacaga tagagcagtt    7980
aattaaccaa agaatagaag aattcgctag gaaccaagcc atctcaaggt tagaaggcct    8040
cagcaacctt taccagattt acgcagaatc ttttcgagag tgggaagcag acccgaccaa    8100
tcctgcctta agagaggaga tgcgcattca attcaatgac atgaacagcg cgctgacgac    8160
cgcaattccg ctcttcgccc ttcagaatta ccagttcct ctttttatccg tgtacgtgca    8220
ggctgccaac ctgcacttgt cggtgctccg cgatgtctcc gtgttcggac aacggtgggg    8280
ctttgatgcc gcaactatca atagtcgtta taatgatctg actaggctta ttggcaacta    8340
taccgattat gctgttcgct ggtacaacac gggtctcgaa cgtgtctggg accggattc    8400
tagagattgg gtcaggtaca accagttcag gcgagagttg acactaactg tcctagacat    8460
```

```
tgtcgctctc tttcccaact acgactctag gcgctaccca atccgtactg tgtcacaatt   8520
gacccgggaa atctacacaa acccagtcct cgagaacttc gacgtagct ttcgaggctc    8580
ggctcagggc atagagagaa gcatcaggtc tccacacctg atggacatat tgaacagtat   8640
cacgatctac accgatgcgc accgcggtta ttactactgg tcagggcatc agatcatggc   8700
atcacccgtt gggttctctg gaccagaatt cactttccca ctttacggga ctatgggcaa   8760
tgcagctcca caacaacgta ttgttgctca actcggtcag ggcgtgtata gaaccttgtc   8820
cagcactcta tataggagac cttttcaacat cggcatcaac aatcaacaat tgtctgtgct   8880
tgacgggaca gaatttgcct atggaacctc ctcaaatctg ccatccgctg tctacagaaa   8940
gagcggaaca gttgatagct tggatgagat ccctccacag aacaacaacg ttccacctag   9000
gcaagggttt agccatcgcc ttagccatgt gtccatgttc cgttcaggct ttagtaatag   9060
cagcgttagt atcatcagag ctccgatgtt ctcttggata catcgtagtg ctgagtttaa   9120
caacataatt gcatccgata gcattactca gatcccagct gtcaagggga actttctctt   9180
taatggttct gtcatttcag gaccaggatt cactggaggc gacttggtta ggctgaattc   9240
ttccgcaac aacatccaga atagagggta tattgaagtg cccattcact tcccatcgac    9300
atctaccaga tatcgtgttc gtgtaaggta tgcctctgtt accccctatt acctcaacgt   9360
caattggggt aattcctcca tcttttccaa tacagtacca gcgacagcta catccttgga   9420
taatctccaa tctagcgatt tcggttactt cgaaagtgcc aatgccttca cctcttccct   9480
aggtaacata gtaggtgtta gaaatttctc cggaaccgcc ggagtgataa tcgaccgctt   9540
cgaattcatt cccgttactg caacgctcga ggcagagtct gacttggaaa gagcacagaa   9600
ggcggtgaat gctctgttca cttcgtccaa tcagattggg ctcaagacag atgtgactga   9660
ctatcacatc gatcgcgttt ccaaccttgt tgagtgcctc tctgatgagt tctgtttgga   9720
tgagaagaag gagttgtccg agaaggtcaa acatgctagt gcctagtg atgagcggaa     9780
cttgcttcaa gatcccaact ttcgcgggat caacaggcaa ctagatcgtg gatggagggg   9840
aagtacggac atcaccattc aaggaggtga tgatgtgttc aaggagaact atgttacgct   9900
cttgggtacc tttgatgagt gctatccaac atacctgtac cagaagatag atgaatcgaa   9960
actcaaagcc tacacaagat accagttgag aggttacatc gaggacagtc aagaccttga  10020
gatctacctc atcagataca acgccaaaca tgaacagtca atgtgcctg gacgggttc    10080
actctggcca ctttcagccc caagtccat cggcaagtgt gcccatcact cacaccactt   10140
ctccttggac atagacgttg gctgtaccga cctgaacgaa gacctcggtg tgtgggtgat  10200
cttcaagatc aagactcaag atggccatgc caggctaggc atctgtgatt ttctagaaga   10260
gaaaccactt gttggagaag ccctcgctag agtgaagagg gctgagaaga gtggagggga  10320
caagagagag aagttggaat gggaaacaaa cattgtgtac aaagaagcca agaaagcgt   10380
tgacgctctg tttgtgaact ctcagtatga taggctccaa gctgatacca acatagctat  10440
gattcatgct gcagacaaac gcgttcatag cattcgggaa gcttaccttc ctgaacttag  10500
cgtgattccg ggtgtcaatg ctgctatctt tgaagagtta gaagggcgca tcttcactgg  10560
attctccttg tatgatgcga ggaatgtcat caagaatggt gacttcaaca atggcctatc  10620
ctgctggaat gtgaaagggc acgtagatgt agaagaacag aacaatcacc gctctgtcct  10680
tgttgttcct gagtgggaag cagaagtttc acaagaagtt cgtgtctgtc ctggtcgtgg  10740
ctacattctt cgtgttaccg cgtacaaaga aggatacgga gaaggttgcg tcaccataca  10800
cgagattgag aacaacaccg acgagctgaa gttcagcaac tgcgtcgagg aggaagtcta  10860
cccaaacaac accgtaactt gcaatgacta cactgcgact caagaggagt atgagggtac  10920
ttacacttct cgcaatcgag gatacgatgg agcctatgag agcaactctt ctgtacccgc  10980
tgactatgca tcagcctatg aggagaaggc ttacaccgat gatgaggagg acaatccttg  11040
cgaatctaac agaggctatg gggactacac accgttacca gccggctatg tcaccaaaga  11100
gttagagtac tttccagaaa ccgacaaggt ttggattgag attggagaaa cggaaggaac  11160
attcattgtt gatagcgtgg agttacttct gatggaggaa tgagtagtta gcttaatcac  11220
ctagagctcg gttacctatc aaaatctatt tagaaataca caatattttg ttgcaggctt  11280
gctggagaat cgatctgcta tcataaaaat tacaaaaaaa ttttattttgc ctcaattatt  11340
ttaggattgg tattaaggac gcttaaatta tttgtcgggt cactacgcat cattgtgatt  11400
gagaagatca gcgatacgaa atattcgtag tactatcgat aatttatttg aaaattcata  11460
agaaaagcaa acgttacatg aattgatgaa acaatacaaa gacagataaa gccacgcaca  11520
tttaggatat tggccagagat tactgaatat tgagtaagat cacggaattt ctgacaggag  11580
catgtcttca attcagccca aatggcagtt gaaatactca aaccgcccca tatgcaggag  11640
cggatcattc attgtttgtt tggttgcctt tgccaacatg ggagtccaag gttgcggccg  11700
cgcgccgacc cagcttttctt gtacaaagtg gttgcgccg cttaattaaa tttaaatgcc    11760
cgggcgttta aacgcggccg cttaattaag gccggcctgc agcaaaccca gaaggtaatt   11820
atccaagatg tagcatcaag aatccaatgt ttacgggaaa aactatggaa gtattatgta   11880
agctcagcaa gaagcagatc aatatgcggc acatatgcaa cctatgttca aaatgaagaa   11940
atgtacagat acaagatcct atactgccag aatacgaaga agaatacga gaaattgaaa    12000
aagaagaacc aggcgaagaa aagaatcttg aagacgtaag cactgacgac aacaatgaaa   12060
agaagaagat aaggtcggtg attgtgaaag agacatagag gacacatgta aggtggaaaa   12120
tgtaagggcg gaaagtaacc ttatcacaaa ggaatcttat cccccactac ttatcctttt   12180
atattttttcc gtgtcatttt tgccgcttgag ttttcctata taaggaacca agttcggcat   12240
ttgtgaaaac aagaaaaaat ttggtgtaag ctattttctt ggatactg aggatacaac      12300
ttcagagaaa tttgtaagtt tgtagatctc catgttctccg gagaggagac cagttgagat   12360
taggccagct acagcagctg atatggccgg ggtttgtgat atcgttaacc attcattga    12420
gacgtctaca gtgaactta ggacagagcc acaaacacca caagagtgga ttgatgatct    12480
agagaggttg caagatagat acccttggtt ggttgctgag gttgagggtg ttgtggctgg   12540
tattgcttac gctgggccct ggaaggctag gaacgcttac gattgacag ttgagagtac     12600
tgtttacgtg tcacataggc atcaaaggtt gggcctagga tccacattgt acacacattt   12660
gcttaagtct atggaggcgc aaggttttaa gtctgtggtt gctgttatag gccttccaaa   12720
cgatccatct gttaggttgc atgaggcttt gggatacaca gccgggtta cattgcgcgc   12780
agctggatac aagcatggtg gatggcatga tgttggtttt tggcaaaggg attttgagtt   12840
gccagctcct ccaaggccag ttaggccagt tacccagatc tgagcttgag 12900
cttatgagct tatgagctta gagctcggat ccactagtaa cggccgccag tgtgctggaa   12960
ttcgcccttg actagatagg cgcccagatc ggcggcaata gcttcttagc gccatcccgg   13020
gttgatccta tctgtgttga aatagttgcg gtgggcaagg ctctctttca gaaagacagg   13080
cggccaaagg aacccaaggt gaggtgggct atggctctca gttccttgtg gaagcgcttg   13140
gtctaaggtg cagaggtgtt agcgggatga agcaaaagtg tccgattgta acaagatatg   13200
```

```
ttgatcctac gtaaggatat taaagtatgt attcatcact aatataatca gtgtattcca    13260
atatgtacta cgatttccaa tgtctttatt gtcgccgtat gtaatcggcg tcacaaaata    13320
atccccggtg actttctttt aatccaggat gaaataatat gttattataa tttttgcgat    13380
ttggtccgtt ataggaattg aagtgtgctt gcggtcgcca ccactcccat ttcataattt    13440
tacatgtatt tgaaaaataa aaatttatgg tattcaattt aaacacgtat acttgtaaag    13500
aatgatatct tgaaagaaat atagtttaaa tatttattga taaaataaca agtcaggtat    13560
tatagtccaa gcaaaaacat aaatttattg atgcaagttt aaattcagaa atatttcaat    13620
aactgattat atcagctggt acattgccgt agatgaaaga ctgagtgcga tattatggtg    13680
taatacatag cggccgggtt tctagtcacc ggttaggatc cgtttaaact cgaggctagc    13740
gcatgcacat agacacacac atcatctcat tgatgcttgg taataattgt cattagattg    13800
tttttatgca tagatgcact cgaaatcagc caattttaga caagtatcaa acggatgtga    13860
cttcagtaca ttaaaaacgt ccgcaatatg atattcatta attttatatt atctaaaaga    13920
gttaaaagag aaaaaagaaa tatgacaatt tttttctttc acatcttcta acctaaaagt    13980
atgactctat ggaggctaag tttagaaaaa gatacggatc tagggtgtgg aaacatcaat    14040
ggtcaactcc ttttatattt caatcaattg ggttttgctt tatctttaca ttttctcctt    14100
ttatttttca cgtctattca aatctacttg ttagcgggtg attactcttt tttcttttat    14160
agatgccaat tatttctctc ctatgtatta aattagagta tattgtcttg aaagtgactt    14220
agtattttag tttatagtct cttaaagaac gacacctttt attcttaact ctctttatca    14280
agttttaatt taaaattatt ttaaattaag tatgcataca tatcttaata ttttttcttaa   14340
ttatttttaa attccctaaa tttaatgttt tcatacaatg taagagatat acatattaat    14400
tatatttaaa gataaaactt actttcctgc aataaaataa agaaaaggac agtcatacaa    14460
ttatataatt aatccagaat atttatagct tttaaacatt tattttctat caattaagta    14520
ataactttaa ataaaattaa gagtactttt ttatactcca aagaatttat ttattttcaa    14580
caaaatcgtc tgactgtttc aattgatcat tatcagccta gcataaccta aatttcattt    14640
tcaaacataa cttttggcac caaatcaccc ggcattgcaa aaaagtcttt tgcgatatga    14700
ccctccacga cgcagaacca ctgttattca ttaccatcct ttttaatcct aatttcccat    14760
acacttaccc tttccatgac atcttcaaag cctttatttt gcttttcttg tttaagctgt    14820
tttaacctaa tttcatgcat ataaacaaag agtaaagcaa aggcaaatat ttgtacgtat    14880
agttttagaa cagaaaagga aagtaaatta tagagataat gaagtttgct cttttaaatt    14940
cgtcgtgatg ttatccatca tatctaaatg cttattcctg ttttttgtctt ttttctcttt   15000
taccggagtt tattttatat aattaattaa agttagtaga tctatattct ttttcataga    15060
taatccatct tctttggagg cacatcgatc attaatcata gagttttgag aagcattatc    15120
actaaagctt caattaatta tatccaataa acggtattgg tgtatgatgt tatgatagca    15180
aatagataat ctaatctata cgagccacaa aagggggcatg aactctatct cgaagaaatt   15240
ggagatgaag ggattgagat tggcaccttg tgctattatt gcccactaat catt          15294
```

STACKED HERBICIDE TOLERANCE EVENT 8264.44.06.1, RELATED TRANSGENIC SOYBEAN LINES, AND DETECTION THEREOF

CROSS-REFERENCE TO RELATED APPLICATIONS

This application is a Divisional Application of U.S. application Ser. No. 17/224,694, filed Apr. 7, 2021, which is a Divisional Application of U.S. application Ser. No. 16/434,995, filed Jun. 7, 2019, and issued as U.S. Pat. No. 10,973,229, which is a Divisional Application of U.S. application Ser. No. 15/399,674, filed Jan. 5, 2017, and issued as U.S. Pat. No. 10,400,250, which is a continuation of U.S. application Ser. No. 13/991,246, filed Sep. 18, 2013, and issued as U.S. Pat. No. 9,540,655, which is a National Stage filing of International Application Serial No. PCT/US2011/063129, filed Dec. 2, 2011 and designating the United States, which claims priority to U.S. Provisional Application Ser. No. 61/419,706, filed Dec. 3, 2010, U.S. Provisional Application Ser. No. 61/471,845, filed Apr. 5, 2011, U.S. Provisional Application Ser. No. 61/511,664, filed Jul. 26, 2011, and U.S. Provisional Application Ser. No. 61/521,798, filed Aug. 10, 2011, the disclosures of each of which are expressly incorporated herein by reference.

INCORPORATION BY REFERENCES OF MATERIAL SUBMITTED ELECTRONICALLY

Incorporated by reference in its entirety is a computer-readable nucleotide/amino acid sequence listing submitted concurrently herewith and identified as follows: 95 kilobytes xml file named "Dowl.xml", created on Aug. 29, 2022.

BACKGROUND OF THE INVENTION

Glyphosate (N-phosphonomethylglycine), a broad-spectrum herbicide, inhibits 5-enolpyruvylshikimate-3-phosphate synthase (EPSPS), an enzyme in the shikimate biosynthetic pathway that produces the essential aromatic amino acids in plant cells. Inhibition of EPSPS effectively disrupts protein synthesis and thereby kills the affected plant cells. Because glyphosate is non-selective, it kills both weeds and crop plants. Thus it is useful with crop plants when one can modify the crop plants to be resistant to glyphosate, allowing the desirable plants to survive exposure to the glyphosate.

Recombinant DNA technology has been used to isolate mutant EPSP synthases that are glyphosate-resistant. Such glyphosate-resistant mutant EPSP synthases can be transformed into plants and confer glyphosate-resistance upon the transformed plants. By way of example, a glyphosate tolerance gene was isolated from *Agrobacterium* strain CP4 as described in U.S. Pat. No. 5,633,435. This reference and all references cited herein are hereby incorporated by reference.

Other glyphosate tolerance genes have been created through the introduction of mutations. These include the AroA gene isolated by Comai and described at U.S. Pat. Nos. 5,094,945, 4,769,061 and 4,535,060. A single mutant has been utilized, as described in U.S. Pat. No. 5,310,667, by substituting an alanine residue for a glycine residue between amino acid positions 80 and 120. Double mutants have been described in U.S. Pat. Nos. 6,225,114 and 5,866,775 in which, in addition to the above mutation, a second mutation (a threonine residue for an alanine residue between positions 170 and 210) was introduced into a wild-type EPSPS gene.

Other work resulted in the production of glyphosate resistant maize through the introduction of a modified maize EPSPS gene bearing mutations at residue 102 (changing threonine to isoleucine) and residue 106 (changing proline to serine) of the amino acid sequence encoded by GenBank Accession No. X63374. See U.S. Pat. Nos. 6,566,587 and 6,040,497.

Examples of events providing resistance to glyphosate in soybeans include soybean line GTS 40-3-2 (Padgette et al. 1995), soybean event MON89788 (U.S. Pat. No. 7,608,761), U.S. Pat. No. 7,608,761 relates to soybean event MON89788, each of which was produced by inserting the cp4 epsps gene into soybean.

The widespread adoption of the glyphosate tolerant cropping system and the increasing use of glyphosate has contributed to the prevalence of glyphosate-resistant and difficult-to-control weeds in recent years. In areas where growers are faced with glyphosate resistant weeds or a shift to more difficult-to-control weed species, growers can compensate for glyphosate's weaknesses by tank mixing or alternating with other herbicides that will control the missed weeds.

One popular and efficacious tankmix partner for controlling broadleaf escapes in many instances has been 2,4-dichlorophenoxyacetic acid (2,4-D). 2,4-D, which has been used as a herbicide for more than 60 years, provides broad spectrum, post-emergence control of many annual, biennial, and perennial broadleaf weeds including several key weeds in corn, soybeans, and cotton. Key weeds controlled by 2,4-D (560-1120 g ac/ha rates) in row crop production include *Ambrosia artemisiifolia, Ambrosia trifida, Xanthium strumarium, Chenopodium album, Helianthus annuus, Ipomoea* sp., *Abutilon theophrasti, Conyza Canadensis*, and *Senna obtusifolia*. 2,4-D provides partial control of several key weeds including *Polygonum pensylvanicum, Polygonum persicaria, Cirsium arvense, Taraxacum officinale*, and *Amaranthus* sp. including *Amaranthus rudis*, and *Amaranthus palmeri*.

A limitation to further use of 2,4-D is that its selectivity in dicot crops like soybean or cotton is very poor, and hence 2,4-D is not typically used on (and generally not near) sensitive dicot crops. Additionally, 2,4-D's use in grass crops is somewhat limited by the nature of crop injury that can occur. 2,4-D in combination with glyphosate has been used to provide a more robust burndown treatment prior to planting no-till soybeans and cotton; however, due to these dicot species' sensitivity to 2,4-D, these burndown treatments must occur at least 14-30 days prior to planting (Agriliance, 2005).

One organism that has been extensively researched for its ability to degrade 2,4-D is *Ralstonia eutropha*, which contains a gene that codes for tfdA (Streber et al., 1987), an enzyme which catalyzes the first step in the mineralization pathway. (See U.S. Pat. No. 6,153,401 and GENBANK Acc. No. M16730). tfdA has been reported to degrade 2,4-D (Smejkal et al., 2001). The products that result from the degradation have little to no herbicidal activity compared to 2,4-D. tfdA has been used in transgenic plants to impart 2,4-D resistance in dicot plants (e.g., cotton and tobacco) normally sensitive to 2,4-D (Streber et al. (1989), Lyon et al. (1989), Lyon (1993), and U.S. Pat. No. 5,608,147).

A number of tfdA-type genes that encode proteins capable of degrading 2,4-D have been identified from the environment and deposited into the Genbank database. Many homologues are similar to tfdA (>85% amino acid identity). However, there are a number of polynucleotide sequences that have a significantly lower identity to tfdA (25-50%), yet have the characteristic residues associated with α-ketoglutarate dioxygenase Fe (II) dioxygenases.

An example of a 2,4-D-degrading gene with low sequence identity (<35%) to tfdA is the aad-12 gene from *Delftia acidovorans* (US Patent App 2011/0203017). The aad-12 gene encodes an S-enantiomer-specific α-ketoglutarate-dependent dioxygenase which has been used in plants to confer tolerance to certain phenoxy auxin herbicides, including, but not limited to: phenoxyacetic acid herbicides such as 2,4-D and MCPA; and phenoxybutanoic acid herbicides, such as 2,4-DB and MCPB) and pyridyloxyalkanoic acid herbicides (e.g., pyridyloxyacetic acid herbicides such as triclopyr and fluroxypyr), and including acid, salt, or ester forms of the active ingredient(s). (See, e.g., WO 2007/053482).

Glufosinate-ammonium ("glufosinate") is a non-systemic, non-selective herbicide in the phosphinothricin class of herbicides. Used primarily for post-emergence control of a wide range of broadleaf and grassy weeds, L-phosphinothricin, the active ingredient in glufosinate, controls weeds through the irreversible inhibition of glutamine-synthase, an enzyme which is necessary for ammonia detoxification in plants. Glufosinate herbicides are sold commercially, for example, under the brand names Ignite®, BASTA, and Liberty®.

The enzyme phosphinothricin N-acetyl transferase (PAT), isolated from the soil bacterium *Streptomyces viridochromogenes*, catalyzes the conversion of L-phosphinothricin to its inactive form by acetylation. A plant-optimized form of the gene expressing PAT has been used in soybeans to confer tolerance to glufosinate herbicide. One such example of glufosinate resistant soybeans is event A5547-127. Most recently, the use of glufosinate herbicide in combination with the glufosinate-tolerance trait has been proposed as a non-selective means to effectively manage ALS- and glyphosate resistant weeds.

The expression of heterologous or foreign genes in plants is influenced by where the foreign gene is inserted in the chromosome. This could be due to chromatin structure (e.g., heterochromatin) or the proximity of transcriptional regulation elements (e.g., enhancers) close to the integration site (Weising et al., *Ann. Rev. Genet* 22:421-477, 1988), for example. The same gene in the same type of transgenic plant (or other organism) can exhibit a wide variation in expression level amongst different events. There may also be differences in spatial or temporal patterns of expression. For example, differences in the relative expression of a transgene in various plant tissues may not correspond to the patterns expected from transcriptional regulatory elements present in the introduced gene construct.

Thus, large numbers of events are often created and screened in order to identify an event that expresses an introduced gene of interest to a satisfactory level for a given purpose. For commercial purposes, it is common to produce hundreds to thousands of different events and to screen those events for a single event that has desired transgene expression levels and patterns. An event that has desired levels and/or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

BRIEF SUMMARY OF THE INVENTION

The subject invention can provide, in part, effective means for managing weed resistance, which helps preserve the usefulness of herbicide-tolerant technologies. The subject invention can also provide growers with great flexibility and convenience in weed control options.

More specifically, the present invention relates in part to the soybean (*Glycine max*) event designated pDAB8264.44.06.1 ("Event pDAB8264.44.06.1") having representative seed deposited with American Type Culture Collection (ATCC) with Accession No. PTA-11336, and progeny derived thereof. The subject invention includes soybean plants comprising Event pDAB8264.44.06.1 (and includes soybean plants comprising a transgenic insert in a genomic segment comprising SEQ ID NO:1 and SEQ ID NO:2).

The transgenic insert present in the subject event and deposited seed comprises three herbicide tolerance genes: aad-12, 2mepsps, and a pat gene. The aad-12 gene, derived from *Delftia acidovorans*, encodes the aryloxyalkanoate dioxygenase (AAD-12) protein, which confers tolerance to, e.g., 2,4-dichlorophenoxyacetic acid and pyridyloxyacetate herbicides. The 2mepsps gene, a modified EPSPS sequence isolated from maize, produces a protein which confers tolerance to glyphosate herbicides. The pat gene, from the soil bacterium *Streptomyces viridochromogenes*, confers tolerance to the herbicide glufosinate.

Other aspects of the invention comprise progeny plants, soybeans, seeds, and/or regenerable parts of the plants and seeds and progeny comprising soybean event pDAB8264.44.06.1, as well as food or feed products made from any thereof. The invention also includes plant parts of Event pDAB8264.44.06.1 that include, but are not limited to, pollen, ovule, flowers, shoots, roots, leaves, nuclei of vegetative cells, pollen cells, and other plant cells that comprise Event pDAB8264.44.06.1. The invention further relates to soybean plants having tolerance to multiple herbicides including phenoxyacetic acid herbicides, phenoxybutanoic acid herbicides, pyridyloxyalkanoic acid herbicides, glyphosate, and/or glufosinate. Such soybean plants may also be stacked with genes that confer tolerance to various other non-selective and selective herbicides, including but not limited to dicamba, imidazolinone, and HPPD herbicides. The invention further includes novel genetic compositions Event pDAB8264.44.06.1 and aspects of agronomic performance of soybean plants comprising Event pDAB8264.44.06.1.

This invention relates in part to plant breeding and herbicide tolerant plants. This invention includes a novel transformation event in soybean plants comprising a polynucleotide, as described herein, inserted into a specific site within the genome of a soybean cell.

In some embodiments, said event/polynucleotide can be "stacked" with other traits, including, for example, agronomic traits and/or insect-inhibitory proteins. However, the subject invention includes plants having the single event, as described herein.

In some embodiments, the subject herbicide tolerance event can be combined in a breeding stack with an insect resistance event. In some of these embodiments, the insect resistance event comprises a cry1F gene and a cry1Ac gene. Some such events and stacks are specifically exemplified herein, including soybean event 9582.812.9.1 ("the 812 Event") and soybean event 9582.814.19.1 ("the 814 Event"). Plants, plant cells, and seeds, for example, comprising any combination of the subject events are included in the subject invention. In some embodiments, the subject invention includes the Soybean Event 9582.812.9.1 (812 Event), alone, as discussed in more detail below.

The additional traits may be stacked into the plant genome, or into the same locus as Event pDAB8264.44.06.1, for example via plant breeding, re-transformation of the transgenic plant containing Event DAS-8264.44.06.1, or addition of new traits through targeted integration via homologous recombination.

Other embodiments include the excision of a portion or all of the transgenic insert and/or flanking sequences of Event DAS-8264.44.06.1. Upon excision, another and/or additional insert can be targeted to the specific chromosomal site of Event DAS-8264.44.06.1. The exemplified insert can be replaced, or further insert(s) can be stacked, in this manner, with the exemplified insert of the subject soybean event.

In one embodiment, the present invention encompasses a soybean chromosomal target site located on chromosome 6. In some embodiments, the target site comprises a heterologous nucleic acid. In some embodiments, the soybean chromosomal target site is located between or within the genomic flanking sequences set forth in SEQ ID NO:1 and SEQ ID NO:2.

In one embodiment, the present invention encompasses a method of making a transgenic soybean plant comprising inserting a heterologous nucleic acid at a position on chromosome 6. In another embodiment, the heterologous nucleic acid is inserted on chromosome 6 near or between various exemplified polynucleotide segments as described herein.

Additionally, the subject invention provides assays for detecting the presence of the subject event in a sample (of soybeans, for example). The assays can be based on the DNA sequence of the recombinant construct, inserted into the soybean genome, and on the genomic sequences flanking the insertion site. Kits and conditions useful in conducting the assays are also provided.

Thus, the subject invention relates in part to the cloning and analysis of the DNA sequences of the whole exemplified insert and the border regions thereof (in transgenic soybean lines). These sequences are unique. Based on these insert and border (and junction) sequences, event-specific primers can be and were generated. PCR analysis demonstrated that the events can be identified by analysis of the PCR amplicons generated with these event-specific primer sets. Thus, these and other related procedures can be used to uniquely identify soybean lines comprising the event of the subject invention.

The subject invention also relates in part to realtime or endpoint TaqMan PCR assays for the detection of event 8264.44.06.1. Some embodiments are directed to assays that are capable of high throughput zygosity analysis. The subject invention further relates, in part, to the use of a GMFL01-25-J19 (GenBank: AK286292.1) reference gene for use in determining zygosity. These and other related procedures can be used to uniquely identify the zygosity of Event pDAB8264.44.06.1 and breed soybean lines comprising the event.

BRIEF DESCRIPTION OF THE FIGURES

FIG. 1 is a plasmid map of pDAB8264.

FIG. 2 is a schematic diagram depicting primer locations for soybean Event pDAB8264.44.06.1.

FIG. 3 is a schematic diagram depicting primer locations and genomic DNA deletion in soybean Event pDAB8264.44.06.1.

FIG. 4 is a schematic diagram depicting primer locations for the TaqMan assay detection of soybean Event pDAB8264.44.06.1.

BRIEF DESCRIPTION OF THE SEQUENCES

SEQ ID NO:1 provides the 5' flanking border sequence for the subject soybean Event pDAB8264.44.06.1.
SEQ ID NO:2 provides the 3' flanking border sequence for the subject soybean Event pDAB8264.44.06.1.
SEQ ID NO:3 provides primer 4406_WF1.
SEQ ID NO:4 provides primer 4406_WF2.
SEQ ID NO:5 provides primer 4406_WF3.
SEQ ID NO:6 provides primer 4406_WF4.
SEQ ID NO:7 provides primer 4406_WR5.
SEQ ID NO:8 provides primer 4406_WR6.
SEQ ID NO:9 provides primer 4406_WR7.
SEQ ID NO:10 provides primer 4406_WR8.
SEQ ID NO:11 provides primer ED_v1_C1.
SEQ ID NO:12 provides primer PAT_12.
SEQ ID NO:13 provides sequence for plasmid pDAB8264.
SEQ ID NO:14 provides partial 5' soybean genomic flanking and partial 5' insert sequence.
SEQ ID NO:15 provides partial 3' soybean genomic flanking and partial 3' insert sequence.
SEQ ID NO:16 provides a 98 base pair sequence spanning the 5' integration junction.
SEQ ID NO:17 provides a 131 base pair sequence spanning the 3' integration junction.
SEQ ID NO:18 provides primer 4406_5'F.
SEQ ID NO:19 provides primer 4406_5'R.
SEQ ID NO:20 provides probe 4406_5'P.
SEQ ID NO:21 provides primer 4406_3'F.
SEQ ID NO:22 provides primer 4406_3'R.
SEQ ID NO:23 provides probe 4406_3'P.
SEQ ID NO:24 provides primer GMS116F.
SEQ ID NO:25 provides primer GMS116R.
SEQ ID NO:26 provides probe GMS116Probe
SEQ ID NO:27 provides the sequence of soybean Event pDAB8264.44.06.1, including the 5' genomic flanking sequence, insert, and 3' genomic flanking sequence.
SEQ ID NO:28 provides the expected sequence of Soybean Event 9582.812.9.1, including the 5' genomic flanking sequence, pDAB9582 T-strand insert, and 3' genomic flanking sequence.
SEQ ID NO:29 provides the expected sequence of Soybean Event 9582.814.19.1, including the 5' genomic flanking sequence, pDAB9582 T-strand insert, and 3' genomic flanking sequence.

DETAILED DESCRIPTION OF THE INVENTION

The invention described herein includes novel transformation events of soybean plants (soybean) comprising a cassette for the expression of multiple herbicide tolerance genes inserted into a specific locus within the genome of a soybean cell.

The exemplified transgenic insert comprising Event pDAB8264.44.06.1 includes genetic elements for the expression of three different herbicide tolerance genes: (1) a synthetic aad-12 gene; (2) an EPSPS sequence from maize encoding a protein containing mutations, as compared to the wild-type EPSPS polypeptide: at amino acid residues 102 (from threonine to isoleucine) and 106 (from proline to serine) and which confers resistance or tolerance to glyphosate herbicides; and (3) a pat gene which confers tolerance or resistance to the glufosinate herbicides. The aad-12 gene was derived from *Delftia acidovorans* and encodes an aryloxyalkanoate dioxygenase (AAD-12) protein enzyme capable of deactivating herbicides having an α-ketoglutarate moiety, including phenoxyalkanoate herbicides (e.g., phenoxyacetic acid herbicides such as 2,4-D and MCPA; phenoxypropionic acid herbicides such as dichlorprop, mecoprop and their enantiomers; and phenoxybutanoic acid herbicides such as 2,4-DB and MCPB) and pyridyloxyalkanoic acid herbicides (e.g., pyridyloxyacetic acid herbicides such as triclopyr and fluroxypyr), including acid, salt, or ester forms of the active ingredient(s)

More specifically, the subject invention relates in part to transgenic soybean Event pDAB8264.44.06.1, plant lines comprising these events, and the cloning and analysis of the DNA sequences of this insert, and/or the border regions thereof. Plant lines of the subject invention can be detected using sequences disclosed and suggested herein.

This invention relates in part to plant breeding and herbicide tolerant plants. In some embodiments, said polynucleotide sequence can be "stacked" with other traits (such as other herbicide tolerance gene(s) and/or gene(s) that encode insect-inhibitory proteins or inhibitory RNA sequences, for example). However, the subject invention also includes plants having a single event, as described herein.

In some embodiments, the subject herbicide tolerance event can be combined in a breeding stack with an insect resistance event. In some embodiments, the insect resistance event is selected from the group consisting of the 812 Event and the 814 Event (as defined in greater detail below), each of which comprises a cry1F gene and a cry1Ac gene. Plants, plant cells, and seeds, for example, comprising any combination of the subject events are included in the subject invention. The subject invention also includes the novel 812 Event, alone, in certain embodiments, including plants, plant cells, and seeds, for example.

U.S. provisional application Ser. No. 61/471,845, filed Apr. 5, 2011, relates in part to soybean lines comprising Soybean Event 9582.812.9.1 (the 812 Event). Seeds comprising this event were deposited and made available to the public without restriction (but subject to patent rights), with the American Type Culture Collection (ATCC), 10801 University Boulevard, Manassas, VA, 20110. The deposit, designated as ATCC Deposit No. PTA-11602, was made on Jan. 20, 2011. This deposit was made and will be maintained in accordance with and under the terms of the Budapest Treaty with respect to seed deposits for the purposes of patent procedure.

U.S. provisional application Ser. No. 61/511,664 (filed Jul. 26, 2011) and 61/521,798 (filed Aug. 10, 2011) relates in part to soybean lines comprising soybean event 9582.814.19.1 (the 814 Event). Seeds comprising this event were deposited with the American Type Culture Collection (ATCC), 10801 University Boulevard, Manassas, VA, 20110. The deposit, ATCC Patent Deposit Designation PTA-12006, was received by the ATCC on Jul. 21, 2011. This deposit was made and will be maintained in accordance with and under the terms of the Budapest Treaty with respect to seed deposits for the purposes of patent procedure.

The subject invention also includes plants, seeds, and plant cells, for example, comprising SEQ ID NO:27 (Event pDAB8264.44.06.1; the 4406 Event), SEQ ID NO:28 (the 812 Event), and/or SEQ ID NO:29 (the 814 Event), and variants of these sequences having, for example, at least 95,%, 96%, 97%, 98%, or 99% identity with such sequences. It is not uncommon for some variation (such as deletion of some segments) to occur upon integration of an insert sequence within the plant genome. This is discussed in more detail in Example 7, for example.

The subject invention also provides assays for detecting the presence of the subject event in a sample. Aspects of the subject invention include methods of designing and/or producing any diagnostic nucleic acid molecules exemplified or suggested herein, particularly those based wholly or partially on the subject flanking sequences.

In some embodiments, a polynucleotide segment exemplified or described herein (such as SEQ ID NO:1, SEQ ID NO:2, and/or the insert therebetween, as depicted in FIG. 2 for example) can be excised and subsequently re-targeted with additional polynucleotide sequence(s).

In some embodiments, this invention relates to herbicide-tolerant soybean lines, and the identification thereof. The subject invention relates in part to detecting the presence of the subject event in order to determine whether progeny of a sexual cross contain the event of interest. In addition, a method for detecting the event is included and is helpful, for example, for complying with regulations requiring the pre-market approval and labeling of foods derived from recombinant crop plants, for example. It is possible to detect the presence of the subject event by any well-known nucleic acid detection method such as polymerase chain reaction (PCR) or DNA hybridization using nucleic acid probes. Event-specific PCR assays are discussed herein. (See e.g. Windels et al. (Med. Fac. Landbouww, Univ. Gent 64/5b: 459462, 1999) for another example.) Some of these examples relate to using a primer set spanning the junction between the insert and flanking DNA. More specifically, one primer included sequence from the insert and a second primer included sequence from flanking DNA.

Exemplified herein is soybean Event pDAB8264.44.06.1, and its selection and characterization for stability and expression in soybean plants from generation to generation. Both flanking sequences of Event pDAB8264.44.06.1 have been sequenced and are described herein as SEQ ID NO:1 and SEQ ID NO:2. Event specific assays were developed. It has also been mapped onto the soybean genome (soybean chromosome 6). Event pDAB8264.44.06.1 can be introgressed into elite cultivars where it will confer tolerance to phenoxy auxin, glyphosate and glufosinate herbicides in inbred and hybrid soybean lines.

The subject EPSPS gene encodes a mutant 5-enolpyruvyl-3-phosphoshikimic acid synthase (EPSPS). The wild-type EPSPS gene was originally isolated from *Zea mays*, and the sequence was deposited under GenBank accession number X63374. See also U.S. Pat. No. 6,566,587 (in particular, SEQ ID No. 3 therein).

To obtain high expression of heterologous genes in plants, it may be preferred to reengineer said genes so that they are more efficiently expressed in plant cells. Modification of the wild-type plant EPSPS nucleotide sequence can provide such resistance when expressed in a plant cell. As described in the '587 patent, when comparing an EPSPS polypeptide to the wild-type polypeptide, modification to substitute isoleucine for threonine at residue 102 and substitute serine for proline at position 106 of the protein, the result is the double mutant EPSPS polypeptide (2mEPSPS) used in the subject insert. When expressed in a plant cell, it provides tolerance to glyphosate. The subject EPSPS gene, also referred to as the "2mepsps gene" or DMMG, can alternatively be optimized to improve expression in both dicotyledonous plants as well as monocotyledonous plants, and in particular in soybean. Codon usage can be selected based upon preferred hemicot codon usage, i.e. redesigned such that the protein is encoded by codons having a bias toward both monocot and dicot plant usage. Deleterious sequences and superfluous restriction sites can be removed to increase the efficiency of transcription/translation of the 2mepsps coding sequence and to facilitate DNA manipulation steps. A hemicot-optimized version of the subject monocot gene is further detailed in U.S. Ser. No. 13/303,502 (filed Nov. 23, 2011, claiming priority to Dec. 3, 2010) entitled, "OPTIMIZED EXPRESSION OF GLYPHOSATE RESISTANCE ENCODING NUCLEIC ACID MOLECULES IN PLANT CELLS."

As previously referenced herein, the introduction and integration of a transgene into a plant genome involves some random events (hence the name "event" for a given insertion that is expressed). That is, with many transformation techniques such as *Agrobacterium* transformation, the "gene gun," and WHISKERS, it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

During the process of introducing an insert into the genome of plant cells, it is not uncommon for some deletions or other alterations of the insert and/or genomic flanking sequences to occur. Thus, the relevant segment of the plasmid sequence provided herein might comprise some minor variations. The same is true for the flanking sequences provided herein. Thus, a plant comprising a polynucleotide having some range of identity with the subject flanking and/or insert sequences is within the scope of the subject invention. Identity to the sequence of the present invention can be a polynucleotide sequence having at least 65% sequence identity, more preferably at least 70% sequence identity, more preferably at least 75% sequence identity, more preferably at least 80% identity, and more preferably at least 85% 86%, 87%, 88%, 89%, 90%, 91%, 92%, 93%, 94%, 95%, 96%, 97%, 98%, 99% sequence identity with a sequence exemplified or described herein. Hybridization and hybridization conditions as provided herein can also be used to define such plants and polynucleotide sequences of the subject invention. The sequence which comprises the flanking sequences plus the full insert sequence can be confirmed with reference to the deposited seed.

As "events" are originally random events, as part of this disclosure at least 2500 seeds of a soybean line comprising Event pDAB8264.44.06.1 have been deposited and made available to the public without restriction (but subject to patent rights), with the American Type Culture Collection (ATCC), 10801 University Boulevard, Manassas, VA, 20110. The deposit has been designated as ATCC Deposit No. PTA-11336. 100 packets (25 seeds per packet) of *Glycine max* seeds ("Soybean Seed *Glycine max* L.: pDAB8264.44.06.1") were deposited on behalf of Dow AgroSciences LLC and MS Technologies, LLC on Sep. 14, 2010. The deposit was tested on Oct. 4, 2010, and on that date, the seeds were viable. This deposit was made and will be maintained in accordance with and under the terms of the Budapest Treaty with respect to seed deposits for the purposes of patent procedure. The deposit will be maintained without restriction at the ATCC depository, which is a public depository, for a period of 30 years, or five years after the most recent request, or for the effective life of the patent, whichever is longer, and will be replaced if it becomes nonviable during that period.

As part of this disclosure at least 2500 seeds of a soybean line comprising Event pDAB9582.812.9.1 and Event pDAB8264.44.06.1 (the subject herbicide tolerance event and the 812 insect resistance event) have been deposited and made available to the public without restriction (but subject to patent rights), with the American Type Culture Collection (ATCC), 10801 University Boulevard, Manassas, VA, 20110. The deposit has been identified as "Designation: pDAB9582.812.9.1:: Event pDAB8264.44.06.1" by the ATCC. 100 packets (25 seeds per packet) of *Glycine max* seeds ("Soybean Seed *Glycine max* L.: pDAB8264.44.06.1") were deposited on Nov. 18, 2011. This deposit was made and will be maintained in accordance with and under the terms of the Budapest Treaty with respect to seed deposits for the purposes of patent procedure. The deposit will be maintained without restriction at the ATCC depository, which is a public depository, for a period of 30 years, or five years after the most recent request, or for the effective life of the patent, whichever is longer, and will be replaced if it becomes nonviable during that period.

The deposited seeds are part of the subject invention. Clearly, soybean plants can be grown from these seeds, and such plants are part of the subject invention. The subject invention also relates to DNA sequences contained in these soybean plants that are useful for detecting these plants and progeny thereof. Detection methods and kits of the subject invention can be directed to identifying any one, two, or even all three of these events, depending on the ultimate purpose of the test.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR § 1.822 is used.

As used herein, the term "progeny" denotes the offspring of any generation of a parent plant which comprises soybean Event pDAB8264.44.06.1.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the soybean native genome flanking the insertion point, the identification or detection of one or the other junction sequences in a plant's genetic material being sufficient to be diagnostic for the event. Included are the DNA sequences that span the insertions in herein-described soybean events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates in part to event identification using such flanking, junction, and insert sequences. Related PCR primers and amplicons are included in the invention. According to the subject invention, PCR analysis methods using amplicons that span across inserted DNA and its borders can be used to detect or identify commercialized transgenic soybean varieties or lines derived from the subject proprietary transgenic soybean lines.

The binary plasmid, pDAB8264 (SEQ ID NO:13) comprises the genetic elements depicted in FIG. 1. The following genetic elements (T-strand border sequences are not included) are contained within the T-strand region of pDAB8264. In Table 1, the residue numbering of the genetic elements is provided with respect to SEQ ID NO:13 disclosed herein.

TABLE 1

Residue Numbering of the Genetic Elements Comprising Binary Plasmid pDAB8264 (SEQ ID NO: 13).

| Genetic Element | Position | Reference |
|---|---|---|
| RB7 MARv3 (Matrix Attachment Region) | 137 bp-1302 bp | Thompson and Myatt, (1997) Plant Mol. Biol., 34: 687-692. ; WO9727207 |
| Intervening Sequence | 1303 bp-1341 bp | Not applicable |
| Histone H4A7 48 3'UTR (Untranslated Region) | 1342 bp-2002 bp | Chabouté et al., (1987) Plant Mol. Biol., 8: 179-191 |
| Intervening Sequence | 2003 bp-2025 bp | Not applicable |
| 2mepsps v1 | 2026 bp-3363 bp | U.S. Pat. No. 6,566,587 |
| OTPc (optimized transit peptide) | 3364 bp-3735 bp | U.S. Pat. No. 5,510,471 |
| Intervening Sequence | 3736 bp-3748 bp | Not applicable |
| Intron 2 | 3749 bp-4214 bp | Chaubet et al., (1992) J. Mol. Biol., 225: 569-574 |
| Histone H4A7 48 Promoter | 4215 bp-5169 bp | Chabouté et al., (1987) Plant Mol. Biol., 8: 179-191 |
| Intervening Sequence | 5170 bp-5261 bp | Not applicable |
| AtUbi 10 Promoter (Arabidopsis thaliana Ubiquitin 10 Promoter) | 5262 bp-6583 bp | Callis, et al., (1990) J. Biol. Chem., 265: 12486-12493 |
| Intervening Sequence | 6584 bp-6591 bp | Not applicable |
| aad-12 v1 | 6592 bp-7473 bp | WO 2007/053482 |
| Intervening Sequence containing stop codons in all 6-frames | 7474 bp-7575 bp | Not applicable |
| AtuORF23 3' UTR (Agrobacterium tumefaciens Open Reading Frame 23 UTR) | 7576 bp-8032 bp | U.S. Pat. No. 5,428,147 |
| Intervening Sequence | 8033 bp-8146 bp | Not applicable |
| CsVMV Promoter (Cassava Vein Mosaic Virus Promoter) | 8147 bp-8663 bp | Verdaguer et al., (1996) Plant Mol. Biol., 31: 1129-1139 |
| Intervening Sequence | 8664 bp-8670 bp | Not applicable |
| pat v6 | 8671 bp-9222 bp | Wohlleben et al., (1988) Gene 70: 25-37 |

TABLE 1-continued

Residue Numbering of the Genetic Elements Comprising Binary Plasmid pDAB8264 (SEQ ID NO: 13).

| Genetic Element | Position | Reference |
|---|---|---|
| Intervening Sequence containing stop codons in all 6-frames | 9223 bp-9324 bp | Not applicable |
| AtuORF1 3'UTR (Agrobacterium tumefaciens Open Reading Frame 1 UTR) | 9325 bp-10028 bp | Huang et al., (1990) J. Bacteriol. 172: 1814-1822 |

SEQ ID NOs: 14 and 15, respectively, are the 5' and 3' flanking sequences together with 5' and 3' portions of the insert sequence, as described in more detail below, and thus include the 5' and 3' "junction" or "transition" sequences of the insert and the genomic DNA. With respect to SEQ ID NO:14, residues 1-570 are 5' genomic flanking sequence, and residues 571-859 are residues of the 5' end of the insert. With respect to SEQ ID NO:15, residues 1-220 are residues of the 3' end of the insert, and residues 221-1719 are 3' genomic flanking sequence. The junction sequence or transition with respect to the 5' end of the insert thus occurs at residues 570-571 of SEQ ID NO:14. The junction sequence or transition with respect to the 3' end of the insert thus occurs at residues 220-221 of SEQ ID NO:15. Polynucleotides of the subject invention include those comprising, for example, 5, 10, 20, 50, 100, 150, or 200 bases, or possibly more, and any increments therebetween, on either side of the junction sequence. Thus, a primer spanning the junction sequence could comprise, for example, 5-10 bases that would hybridize with flanking sequence and 5-10 bases that would hybridize with insert sequence. Probes and amplicons could be similarly designed, although they would often be longer than primers.

The subject sequences (including the flanking sequences) are unique. Based on these insert and flanking sequences, event-specific primers were generated. PCR analysis demonstrated that these soybean lines can be identified in different soybean genotypes by analysis of the PCR amplicons generated with these event-specific primer sets. Thus, these and other related procedures can be used to uniquely identify these soybean lines. The sequences identified herein are unique.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit soybean breeding programs as well as quality control, especially for commercialized transgenic soybean seeds. PCR detection kits for these transgenic soybean lines can also now be made and used. This can also benefit product registration and product stewardship.

Furthermore, flanking soybean/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of the subject disclosure, it should be clear that the subject invention includes seeds available under ATCC Deposit No. PTA-11336. The subject invention also includes a herbicide-tolerant soybean plant grown from a seed deposited with the ATCC under accession number PTA-11336. The subject invention further includes parts of said plant, such as leaves, tissue samples, seeds produced by said plant, pollen, and the like (wherein they comprise a transgenic insert flanked by SEQ ID NO:1 and SEQ ID NO:2).

Still further, the subject invention includes descendant and/or progeny plants of plants grown from the deposited seed, preferably a herbicide-resistant soybean plant wherein said plant has a genome comprising a detectable wild-type genomic DNA/insert DNA junction sequence as described herein. As used herein, the term "soybean" means *Glycine max* and includes all varieties thereof that can be bred with a soybean plant.

The invention further includes processes of making crosses using a plant of the subject invention as at least one parent. For example, the subject invention includes an $F_1$ hybrid plant having as one or both parents any of the plants exemplified herein. Also within the subject invention is seed produced by such $F_1$ hybrids of the subject invention. This invention includes a method for producing an $F_1$ hybrid seed by crossing an exemplified plant with a different (e.g. in-bred parent) plant and harvesting the resultant hybrid seed. The subject invention includes an exemplified plant that is either a female parent or a male parent. Characteristics of the resulting plants may be improved by careful consideration of the parent plants.

A herbicide-tolerant soybean plant of the subject invention can be bred by first sexually crossing a first parental soybean plant consisting of a soybean plant grown from seed of any one of the lines referred to herein, and a second parental soybean plant, thereby producing a plurality of first progeny plants; then selecting a first progeny plant that is resistant to a herbicide (or that possesses at least one of the events of the subject invention); selfing the first progeny plant, thereby producing a plurality of second progeny plants; and then selecting from the second progeny plants a plant that is resistant to a herbicide (or that possesses at least one of the events of the subject invention). These steps can further include the back-crossing of the first progeny plant or the second progeny plant to the second parental soybean plant or a third parental soybean plant. A soybean crop comprising soybean seeds of the subject invention, or progeny thereof, can then be planted.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The DNA molecules of the present invention can be used as molecular markers in a marker assisted breeding (MAB) method. DNA molecules of the present invention can be used in methods (such as, AFLP markers, RFLP markers, RAPD markers, SNPs, and SSRs) that identify genetically linked agronomically useful traits, as is known in the art. The herbicide-resistance trait can be tracked in the progeny of a cross with a soybean plant of the subject invention (or progeny thereof and any other soybean cultivar or variety) using the MAB methods. The DNA molecules are markers for this trait, and MAB methods that are well known in the art can be used to track the herbicide-resistance trait(s) in soybean plants where at least one soybean line of the subject invention, or progeny thereof, was a parent or ancestor. The methods of the present invention can be used to identify any soybean variety having the subject event.

Methods of the subject invention include a method of producing a herbicide-tolerant soybean plant wherein said method comprises introgessing Event pDAB8264.44.06.1 into a soybean cultivar. More specifically, methods of the present invention can comprise crossing two plants of the subject invention, or one plant of the subject invention and any other plant. Preferred methods further comprise selecting progeny of said cross by analyzing said progeny for an event detectable according to the subject invention. For example, the subject invention can be used to track the subject event through breeding cycles with plants comprising other desirable traits, such as agronomic traits such as those tested herein in various Examples. Plants comprising the subject event and the desired trait can be detected, identified, selected, and quickly used in further rounds of breeding, for example. The subject event/trait can also be combined through breeding, and tracked according to the subject invention, with an insect resistant trait(s) and/or with further herbicide tolerance traits. One embodiment of the latter is a plant comprising the subject event combined with a gene encoding resistance to the herbicide dicamba.

Thus, the subject invention can be combined with, for example, additional traits encoding glyphosate resistance (e.g., resistant plant or bacterial glyphosate oxidase (GOX)), glyphosate acetyl transferase (GAT), additional traits for glufosinate resistance (e.g. bialaphos resistance (bar)), traits conferring acetolactate synthase (ALS)-inhibiting herbicide resistance (e.g., imidazolinones [such as imazethapyr], sulfonylureas, triazolopyrimidine sulfonanilide, pyrmidinyl-thiobenzoates, and other chemistries [Csr1, SurA, et al.]), bromoxynil resistance traits (e.g., Bxn), traits for resistance to dicamba herbicide (see, e.g., U.S. 2003/0135879), traits for resistance to inhibitors of HPPD (4-hydroxlphenyl-pyruvate-dioxygenase) enzyme, traits for resistance to inhibitors of phytoene desaturase (PDS), traits for resistance to photosystem II inhibiting herbicides (e.g., psbA), traits for resistance to photosystem I inhibiting herbicides, traits for resistance to protoporphyrinogen oxidase IX (PPO)-inhibiting herbicides (e.g., PPO-1), and traits for resistance to phenylurea herbicides (e.g., CYP76B1). One or more of such traits can be combined with the subject invention to provide the ability to effectively control, delay and/or prevent weed shifts and/or resistance to herbicides of multiple classes.

It will be appreciated by those of skill in the art that the aad-12 gene used in the subject invention also provides resistance to compounds that are converted to phenoxyacetate auxin herbicides (e.g., 2,4-DB, MCPB, etc.). The butyric acid moiety present in the 2,4-DB herbicide is converted through β-oxidation to the phytotoxic 2,4-dichlorophenoxyacetic acid. Likewise, MCPB is converted through β-oxidation to the phytotoxic MCPA. The butanoic acid herbicides are themselves nonherbicidal, but are converted to their respective acid from by β-oxidation within susceptible plants to produce the acetic acid form of the herbicide that is phytotoxic. Plants incapable of rapid β-oxidation are not harmed by the butanoic acid herbicides. However, plants that are capable of rapid β-oxidation and can convert the butanoic acid herbicide to the acetic form are subsequently protected by AAD-12.

Methods of applying herbicides are well known in the art. Such applications can include tank mixes of more than one herbicide. Preferred herbicides for use according to the subject invention are combinations of glyphosate, glufosinate, and a phenoxy auxin herbicide (such as 2,4-D; 2,4-DB; MCPA; MCPB). Other preferred combinations include glyphosate plus 2,4-D or glufosinate plus 2,4-D mixtures. These three types of herbicides can be used in advantageous combinations that would be apparent to one skilled in the art having the benefit of the subject disclosure. One or more of the subject herbicides can be applied to a field/area prior to planting it with seeds of the subject invention. Such applications can be within 14 days, for example, of planting seeds of the subject invention. One or more of the subject herbicides can also be applied after planting prior to emergence. One or more of the subject herbicides can also be applied to the ground (for controlling weeds) or over the top of the weeds and/or over the top of transgenic plants of the subject invention. The subject three herbicides can be rotated or used in combination to, for example, control or prevent weeds that might to tolerant to one herbicide but not another. Various application times for the subject three types of herbicides can be used in various ways as would be known in the art.

Additionally, the subject event can be stacked with one or more additional herbicide tolerance traits, one or more additional input (e.g., insect resistance (e.g., the 812 Event or the 814 Event), fungal resistance, or stress tolerance, et al.) or output (e.g., increased yield, improved oil profile, improved fiber quality, et al.) traits, both transgenic and nontransgenic. Thus, the subject invention can be used to provide a complete agronomic package of improved crop quality with the ability to flexibly and cost effectively control any number of agronomic pests.

Methods to integrate a polynucleotide sequence within a specific chromosomal site of a plant cell via homologous recombination have been described within the art. For instance, site specific integration as described in U.S. Patent Application Publication No. 2009/0111188 A1, describes the use of recombinases or integrases to mediate the introduction of a donor polynucleotide sequence into a chromosomal target. In addition, International Patent Application No. WO 2008/021207 describes zinc finger mediated-homologous recombination to integrate one or more donor polynucleotide sequences within specific locations of the genome. The use of recombinases such as FLP/FRT as described in U.S. Pat. No. 6,720,475, or CRE/LOX as described in U.S. Pat. No. 5,658,772, can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060).

Other various methods for site specific integration within plant cells are generally known and applicable (Kumar et al., *Trends in Plant Sci.* 6(4) (2001) pp. 155-159). Furthermore, site-specific recombination systems which have been identified in several prokaryotic and lower eukaryotic organisms may be applied to use in plants. Examples of such systems include, but are not limited too; the R/RS recombinase system from the pSR1 plasmid of the yeast *Zygosaccharomyces rouxii* (Araki et al. (1985) J. Mol. Biol. 182: 191-203), and the Gin/gix system of phage Mu (Maeser and Kahlmann (1991) Mol. Gen. Genet. 230: 170-176).

In some embodiments of the present invention, it can be desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. The newly integrated transgenes should maintain the transgene expression characteristics of the existing transformants. Moreover, the development of assays for the detection and confirmation of the newly integrated event would be overcome as the genomic flanking sequences and chromosomal location of the newly integrated event are already identified. Finally, the integration of a new transgene into a specific chromosomal location which is linked to an existing transgene would expedite the introgression of the transgenes into other genetic backgrounds by sexual out-crossing using conventional breeding methods.

In some embodiments of the present invention, it can be desirable to excise polynucleotide sequences from a transgenic event. For instance transgene excision as described in U.S. patent application Ser. No. 13/011,666, describes the use of zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

The subject invention discloses herein a specific site on chromosome 6 in the soybean genome that is excellent for insertion of heterologous nucleic acids. Also disclosed is a 5' flanking sequence and a 3' flanking sequence, which can also be useful in identifying and/or targeting the location of the insertion/targeting site on chromosome 6. Thus, the subject invention provides methods to introduce heterologous nucleic acids of interest into this pre-established target site or in the vicinity of this target site. The subject invention also encompasses a soybean seed and/or a soybean plant comprising any heterologous nucleotide sequence inserted at the disclosed target site or in the general vicinity of such site. One option to accomplish such targeted integration is to excise and/or substitute a different insert in place of the pat expression cassette exemplified herein. In this general regard, targeted homologous recombination, for example and without limitation, can be used according to the subject invention.

As used herein gene, event or trait "stacking" is combining desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

The subject event enables transgenic expression of three different herbicide tolerance proteins resulting in tolerance to combinations of herbicides that would control nearly all broadleaf and grass weeds. This multi-herbicide tolerance trait expression cassette/transgenic insert can be stacked with other herbicide tolerance traits (e.g., glyphosate resistance, glufosinate resistance, imidazolinone resistance, dicamba resistance, HPPD resistance, bromoxynil resistance, et al.), and insect resistance traits (such as Cry1F, Cry1Ab, Cry1Ac, Cry 34/45, Cry1Be, Cry1Ca, Cry1Da, Cry1Ea, Cry1Fa, vegetative insecticidal proteins ("VIPS")—including VIP3A, and the like), for example. Additionally, the herbicide tolerance proteins in the expression cassette/transgenic insert of the subject invention can serve as one or more selectable marker sto aid in selection of primary transformants of plants genetically engineered with a second gene or group of genes.

These combinations of traits give rise to novel methods of controlling weeds (and like) species, due to the newly acquired resistance or inherent tolerance to herbicides (e.g., glyphosate). Thus, novel methods for controlling weeds using Event pDAB8264.44.06.1 are within the scope of the invention.

The use of the subject transgenic traits, stacked or transformed individually into crops, provides a tool for controlling other herbicide tolerant volunteer crops that do not contain genes for conferring tolerance to phenoxy, pyridyloxy, glyphosate and/or glufosinate herbicides.

A preferred plant, or a seed, of the subject invention comprises in its genome the insert sequences, as identified herein, together with at least 20-500 or more contiguous flanking nucleotides on both sides of the insert, as described herein. Unless indicated otherwise, reference to flanking sequences refers to those identified with respect to SEQ ID NO:1 and SEQ ID NO:2. Again, the subject events include heterologous DNA inserted between the subject flanking genomic sequences immediately adjacent to the inserted DNA. All or part of these flanking sequences could be expected to be transferred to progeny that receives the inserted DNA as a result of a sexual cross of a parental line that includes the event.

The subject invention includes tissue cultures of regenerable cells of a plant of the subject invention. Also included is a plant regenerated from such tissue culture, particularly where said plant is capable of expressing all the morphological and physiological properties of an exemplified variety. Preferred plants of the subject invention have all the physiological and morphological characteristics of a plant grown from the deposited seed. This invention further comprises progeny of such seed and seed possessing the quality traits of interest.

Manipulations (such as mutation, further transfection, and further breeding) of plants or seeds, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when
  (i) it is predominantly derived from the initial variety, or from a variety that is itself predominantly derived from the initial variety, while retaining the expression of the essential characteristics that result from the genotype or combination of genotypes of the initial variety;
  (ii) it is clearly distinguishable from the initial variety; and
  (iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial canola variety without the premium value traits grown in the same region.

"Agronomically elite" means that a line has desirable agronomic characteristics such as yield, maturity, disease resistance, and the like, in addition to the herbicide tolerance due to the subject event(s). Agronomic traits, taken individually or in any combination, as set forth in Examples, below, in a plant comprising an event of the subject invention, are within the scope of the subject invention. Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the soybean genomic flanking sequence meets the insert sequence). For example, this includes a polynucleotide probes, primers, and/or amplicons designed to identify one or both junction sequences (where the insert meets the flanking sequence), as indicated in the Table 1. One common design is to have one primer that hybridizes in the flanking region, and one primer that hybridizes in the insert. Such primers are often each about at least 15 residues in length. With this arrangement, the primers can be used to generate/amplify a detectable amplicon that indicates the presence of an event of the subject invention. These primers can be used to generate an amplicon that spans (and includes) a junction sequence as indicated above.

The primer(s) "touching down" in the flanking sequence is typically not designed to hybridize beyond about 200 bases or so beyond the junction. Thus, typical flanking primers would be designed to comprise at least 15 residues of either strand within 200 bases into the flanking sequences from the beginning of the insert. That is, primers comprising a sequence of an appropriate size from (or hybridizing to) residues within 100 to 200-500 or so bases from either or both junction sequences identified above are within the scope of the subject invention. Insert primers can likewise be designed anywhere on the insert, but residues on the insert (including the complement) within 100 to 200-500 or so bases in from the junction sequence(s) identified above, can be used, for example, non-exclusively for such primer design.

One skilled in the art will also recognize that primers and probes can be designed to hybridize, under a range of standard hybridization and/or PCR conditions, to segments of sequences exemplified herein (or complements thereof), wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

It should be noted that errors in PCR amplification can occur which might result in minor sequencing errors, for example. That is, unless otherwise indicated, the sequences listed herein were determined by generating long amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the "insert" are illustrated in the Figures and are discussed in more detail below in the Examples. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a soybean plant. DNA sequences are provided that comprise the subject transgene/genomic insertion region junction sequence provided herein, segments comprising a junction sequence identified herein, and complements of any such exemplified sequences and any segments thereof. The insertion region junction sequence spans the junction between heterologous DNA inserted into the genome and the DNA from the soybean cell flanking the insertion site. Such sequences can be diagnostic for the given event.

Based on these insert and border sequences, event-specific primers can be generated. PCR analysis demonstrated that soybean lines of the subject invention can be identified in different soybean genotypes by analysis of the PCR amplicons generated with these event-specific primer sets. These and other related procedures can be used to uniquely identify these soybean lines. Thus, PCR amplicons derived from such primer pairs are unique and can be used to identify these soybean lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of soybean genomic sequence from one or more of the aforementioned soybean plants and/or sequences that are useful as primer sequences for the production of an amplicon product diagnostic for one or more of these soybean plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence identified herein, or complements thereof, and a similar length of flanking soybean DNA sequence (such as SEQ ID NO:1 and SEQ ID NO:2 and segments thereof) from these sequences, or complements thereof. Such sequences are useful as DNA primers in DNA amplification methods. The amplicons produced using these primers are diagnostic for any of the soybean events referred to herein. Therefore, the invention also includes the amplicons produced by such DNA primers and homologous primers.

This invention also includes methods of detecting the presence of DNA, in a sample, that corresponds to the soybean event referred to herein. Such methods can comprise: (a) contacting the sample comprising DNA with a primer set that, when used in a nucleic acid amplification reaction with DNA from at least one of these soybean events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to said event, wherein said method comprises: (a) contacting the sample comprising DNA with a probe that hybridizes under stringent hybridization conditions with DNA from at least one of said soybean events and which does not hybridize under the stringent hybridization conditions with a control soybean plant (non-event-of-interest DNA); (b) subjecting the sample and probe to stringent hybridization conditions; and (c) detecting hybridization of the probe to the DNA.

In still further embodiments, the subject invention includes methods of producing a soybean plant comprising Event pDAB8264.44.06.1, wherein said method comprises the steps of: (a) sexually crossing a first parental soybean line (comprising an expression cassettes of the present invention, which confers said herbicide resistance trait to plants of said line) and a second parental soybean line (that lacks this herbicide tolerance trait) thereby producing a plurality of progeny plants; and (b) selecting a progeny plant by the use of molecular markers. Such methods may optionally comprise the further step of back-crossing the progeny plant to the second parental soybean line to producing a true-breeding soybean plant that comprises said herbicide tolerance trait.

According to another aspect of the invention, methods of determining the zygosity of progeny of a cross with said event is provided. Said methods can comprise contacting a sample, comprising soybean DNA, with a primer set of the subject invention. Said primers, when used in a nucleic-acid amplification reaction with genomic DNA from at least one of said soybean events, produces a first amplicon that is diagnostic for at least one of said soybean events. Such methods further comprise performing a nucleic acid amplification reaction, thereby producing the first amplicon; detecting the first amplicon; and contacting the sample comprising soybean DNA with said primer set (said primer set, when used in a nucleic-acid amplification reaction with genomic DNA from soybean plants, produces a second amplicon comprising the native soybean genomic DNA homologous to the soybean genomic region; and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject soybean event DNA in a sample and can be applied to methods for breeding soybean plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said soybean events, whether from a soybean plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence. An "isolated" polynucleotide connotes that the polynucleotide is in a non-natural state—operably linked to a heterologous promoter, for example. A "purified" protein likewise connotes that the protein is in a non-natural state.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., with regards to endpoint TaqMan and real-time PCR applications, one will select 1.5 mM to about 4.0 mM $MgCl_2$ at temperature of about 60° C. to about 75° C. and may vary hold times, as described herein, for increasing stringency. For other hybridization techniques one will typically employ relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0×sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence as set forth herein in one of the exemplified sequences, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject soybean event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of the present invention. Following this method, an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the soybean genome that is excellent for an insertion, the subject invention also includes a soybean seed and/or a soybean plant comprising at least one non-aad12/pat/2mepsps coding sequence in or around the general vicinity of this genomic location. One option is to substitute a different insert in place of the insert exemplified herein. In these general regards, targeted homologous recombination, for example, can be used according to the subject invention. This type of technology is the subject of, for example, WO 03/080809 A2 and the corresponding published U.S. application (U.S. 2003/0232410). Thus, the subject invention includes plants and plant cells comprising a heterologous insert (in place of or with multi-copies of the exemplified insert), flanked by all or a recognizable part of the flanking sequences identified herein as SEQ ID NO:1 and SEQ ID NO:2. An additional copy (or additional copies) of the exemplified insert or any of its components could also be targeted for insertion in this/these manner(s).

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention.

Unless otherwise indicated, all percentages are by weight and all solvent mixture proportions are by volume unless otherwise noted.

The following abbreviations are used unless otherwise indicated.

bp base pair
° C. degrees Celcius
DNA deoxyribonucleic acid
DIG digoxigenin
EDTA ethylenediaminetetraacetic acid
kb kilobase
μg microgram
μL microliter
mL milliliter
M molar mass
OLP overlapping probe
PCR polymerase chain reaction
PTU plant transcription unit
SDS sodium dodecyl sulfate
SOP standard operating procedure
SSC a buffer solution containing a mixture of sodium chloride and sodium citrate, pH 7.0
TBE a buffer solution containing a mixture of Tris base, boric acid and EDTA, pH 8.3
V volts

EXAMPLES

Example 1: Transformation and Selection of the 2mEPSPS and AAD-12 Soybean Event 8264.44.06.1

Transgenic soybean (*Glycine max*) containing the Soybean Event 8264.44.06.1 was generated through *Agrobacterium*-mediated transformation of soybean cotyledonary node explants. The disarmed *Agrobacterium* strain EHA101 (Hood et al., 2006), carrying the binary vector pDAB8264 (FIG. 1) containing the selectable marker, pat, and the genes of interest, aad-12 and 2mepsps v1, within the T-strand DNA region, was used to initiate transformation.

*Agrobacterium*-mediated transformation was carried out using a modified procedure of Zeng et al. (2004). Briefly, soybean seeds (cv Maverick) were germinated on basal media and cotyledonary nodes were isolated and infected with *Agrobacterium*. Shoot initiation, shoot elongation, and rooting media were supplemented with cefotaxime, timentin and vancomycin for removal of *Agrobacterium*. Glufosinate selection was employed to inhibit the growth of non-transformed shoots. Selected shoots were transferred to rooting medium for root development and then transferred to soil mix for acclimatization of plantlets.

Terminal leaflets of selected plantlets were leaf painted with glufosinate to screen for putative transformants. The screened plantlets were transferred to the greenhouse, allowed to acclimate and then leaf-painted with glufosinate to reconfirm tolerance and deemed to be putative transformants. The screened plants were sampled and molecular analyses for the confirmation of the selectable marker gene and/or the gene of interest were carried out. $T_0$ plants were allowed to self fertilize in the greenhouse to give rise to $T_1$ seed.

This event, Soybean Event 8264.44.06.1, was generated from an independent transformed isolate. The $T_1$ plants were backcrossed and introgressed into elite varieties over subsequent generations. The event was selected based on its unique characteristics such as single insertion site, normal Mendelian segregation and stable expression, and a superior combination of efficacy, including herbicide tolerance and agronomic performance. The following examples contain the data which were used to characterize Soybean Event 8264.44.06.1.

Example 2: Characterization of AAD-12, 2mEPSPS and PAT Protein in Soybean Event 8264.44.06.1

The biochemical properties of the recombinant AAD-12, 2mEPSPS and PAT protein derived from the transgenic soybean event pDAB8264.44.06.1 were characterized. Quantitative enzyme-linked immunosorbent assay (ELISA) was used to characterize the biochemical properties of the protein and confirm expression of AAD-12, PAT and 2mEPSPS protein.

Example 2.1: Expression of the AAD-12 Protein in Plant Tissues

Levels of AAD-12 protein were determined in soybean event 8264.44.06.1. The soluble, extractable AAD-12 protein was measured using a quantitative enzyme-linked immunosorbent assay (ELISA) method from soybean leaf tissue.

Samples of soybean tissues were isolated from the test plants and prepared for expression analysis. The AAD-12 protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an AAD-12 ELISA kit in a sandwich format. The kit was used following the manufacturer's suggested protocol.

Detection analysis was performed to investigate the expression stability and heritability both vertically (between generations) and horizontally (between lineages of the same generation) in soybean event 8264.44.06.1. At the T4 generation soybean event 8264.44.06.1 expression was stable (not segregating) and consistent across all lineages. Field expression level studies were performed on soybean event; average expression across all lineages was approximately 200-400 ng/cm$^2$.

Example 2.2: Expression of the 2mEPSPS Protein in Plant Tissues

Levels of 2mEPSPS protein were determined in soybean event 8264.44.06.1. The soluble, extractable 2mEPSPS protein was measured using a quantitative enzyme-linked immunosorbent assay (ELISA) method from soybean leaf tissue.

Samples of soybean tissues were isolated from the test plants and prepared for expression analysis. The 2mEPSPS protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using a 2mEPSPS ELISA kit in a sandwich format. The kit was used following the manufacturer's suggested protocol.

Detection analysis was performed to investigate the expression stability and heritability both vertically (between generations) and horizontally (between lineages of the same generation) in soybean event 8264.44.06.1. At the T4 generation soybean event 8264.44.06.1 expression was stable (not segregating) and consistent across all lineages. Field expression level studies were performed on soybean event 8264.44.06.1. Average expression across all lineages was approximately 5,000-17,500 ng/cm$^2$. These expression levels were higher than the positive control which expressed the 2mEPSPS protein.

Example 2.3: Expression of the PAT Protein in Plant Tissues

Levels of PAT protein were determined in soybean event 8264.44.06.1. The soluble, extractable PAT protein was measured using a quantitative enzyme-linked immunosorbent assay (ELISA) method from soybean leaf tissue.

Samples of soybean tissues were isolated from the test plants and prepared for expression analysis. The PAT protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using a PAT ELISA kit in a sandwich format. The kit was used following the manufacturer's suggested protocol.

Detection analysis was performed to investigate the expression stability and heritability both vertically (between generations) and horizontally (between lineages of the same generation) in soybean event 8264.44.06.1. At the T4 generation soybean event 8264.44.06.1 expression was stable (not segregating) and consistent across all lineages. Field expression level studies were performed on soybean event 8264.44.06.1. Average expression across all lineages was approximately 15-25 ng/cm$^2$.

Example 3: Cloning and Characterization of DNA Sequence in the Insert and the Flanking Border Regions of Soybean Event pDAB8264.44.06.1

To characterize and describe the genomic insertion site, the sequence of the flanking genomic T-DNA border regions of soybean event pDAB8264.44.06.1 were determined. In total, 2,578 bp of soybean event pDAB8264.44.06.1 genomic sequence was confirmed, comprising 570 bp of 5' flanking border sequence (SEQ ID NO:1), 1,499 bp of 3' flanking border sequence (SEQ ID NO:2). PCR amplification based on the soybean Event pDAB8264.44.06.1 border sequences validated that the border regions were of soybean origin and that the junction regions are unique sequences for event pDAB8264.44.06.1. The junction regions could be used for event-specific identification of soybean event pDAB8264.44.06.1. In addition, the T-strand insertion site was characterized by amplifying a genomic fragment corresponding to the region of the identified flanking border sequences from the genome of wild type soybean. Comparison of soybean event pDAB8264.44.06.1 with the wild type genomic sequence revealed about 4,357 bp deletion from the original locus. Overall, the characterization of the insert and border sequence of soybean event pDAB8264.44.06.1 indicated that an intact copy of the T-strand was present in the soybean genome.

TABLE 2

Primers and sequences used to analyze Soybean Event pDAB8264.44.06.1

| SEQ ID NO: | Primer Name | Size (bp) | Sequence (5' to 3') | Purpose |
|---|---|---|---|---|
| SEQ ID NO: 3 | 4406_WF1 | 25 | AGGTTGTCATTCCGCTGAAGAAGAT | confirmation of 5' border genomic DNA, used with ED_v1_C1 |
| SEQ ID NO: 4 | 4406_WF2 | 25 | CACAGTGGACAATTCTGATTTCTGG | confirmation of 5' border genomic DNA, used with ED_v1_C |
| SEQ ID NO: 5 | 4406_WF3 | 25 | GGATTGCATCTGAAACGGATCATAT | confirmation of 5' border genomic DNA, used with ED_v1_C1 |
| SEQ ID NO: 6 | 4406_WF4 | 25 | GGAATGTTGAACCACCCATGATTAA | confirmation of 5' border genomic DNA, used with ED_v1_C |
| SEQ ID NO: 7 | 4406-WR5 | 25 | CATGTATGTTGTTGTCGTTGCCTTG | confirmation of 3' border genomic DNA, used with PAT_12 |
| SEQ ID NO: 8 | 4406-WR6 | 25 | AACATTTTGAAATCGGTTCCAAGGA | confirmation of 3' border genomic DNA, used with PAT_12 |
| SEQ ID NO: 9 | 4406-WR7 | 25 | AGGCTCAGGCCAACAACATTAATTT | confirmation of 3' border genomic DNA, used with PAT_12 |
| SEQ ID NO: 10 | 4406-WR8 | 27 | GGAGAGAAGTCGCAACAGTGATTACAT | confirmation of 3' border genomic DNA, used with PAT_12 |
| SEQ ID NO: 11 | ED_v1_C1 | 26 | GAGTAAAGGAGACCGAGAGGATGGTT | confirmation of 5' border genomic DNA, used with 4406_WF1, 4406_WF2, 4406_WF3, or 4406_WF4, |
| SEQ ID NO: 12 | PAT_12 | 24 | GAACGCTTACGATTGGACAGTTGA | confirmation of 3' border genomic DNA, used with 4406_WR5, 4406_WR62, 4406_WR7, or 4406_W R8 |

TABLE 3

PCR conditions for amplification of border regions and event-specific sequences in soybean event pDAB8264.44.06.1.

| Target Sequence | Primeret | PCH Mixture | Pre-denature (° C./min) | Denature (° C./sec.) | Anneal (° C./sec.) | Extension (° C./min:sec) | Final Extension (° C./min) |
|---|---|---|---|---|---|---|---|
| 5' border | 4406-WF1/ED_v1_C1 | D | 95/3 | 98/10 | 66/30 32 cycles | 68/4:00 | 72/10 |
| 5' border | 4406-WF3/ED_v1_C1 | D | 95/3 | 98/10 | 66/30 32 cycles | 68/4:00 | 72/10 |
| 3' border | 4406-WR5/PAT_12 | D | 95/3 | 98/10 | 66/30 35 cycles | 68/4:00 | 72/10 |
| 3' border | 4406-WR7/PAT_12 | D | 95/3 | 98/10 | 66/30 32 cycles | 68/4:00 | 72/10 |
| 3' border | 4406-WR8/PAT_12 | D | 95/3 | 98/10 | 66/30 35 cycles | 68/4:00 | 72/10 |
| Across the insert locus | 4406-WF1/4406-WR5 | D | 95/3 | 98/10 | 66/30 32 cycles | 68/10:00 | 72/10 |
| Across the insert locus | 4406-WF3/4406-WR7 | D | 95/3 | 98/10 | 66/30 32 cycles | 68/10:00 | 72/10 |

TABLE 4

PCR mixture for amplification of border regions and event specific sequences in soybean event pDAB8264.44.06.1.

| PCR Mixture A | | PCR Mixture B | |
|---|---|---|---|
| Reagent | 1× reaction (μL) | Reagent | 1× reaction (μL) |
| H20 | 0.8 | H20 | 14.6 |
| AccPrime pfx SuperMix | 20 | 10× LA Taq buffer | 2 |
| — | — | MgCl2 (25 mM) | 0.6 |
| — | — | dNTP (2.5 uM) | 1.6 |
| 10 uM primer | 0.2 | 10 uM primer | 0.1 |
| gDNA digestion | 1 | gDNA digestion | 1 |
| — | — | LA Taq (5 U/ul) | 0.1 |
| rxn vol: | 22 | rxn vol: | 20 |
| PCR Mixture C | | PCR Mixture D | |
| Reagent | 1× reaction (μL) | Reagent | 1× reaction (μL) |
| H20 | 28 | H20 | 11.6 |
| 10× PCR buffer II (Mg-plus) | 5 | 10× PCR buffer II (Mg-plus) | 2 |
| MgCl$_2$[25 mM] | 1.5 | MgCl$_2$[25 mM] | 0.6 |
| dNTP[2.5 mM] | 8 | dNTP[2.5 mM] | 3.2 |
| Adaptor PCR primer (10 μM) | 1 | primer1 (10 μM) | 0.4 |
| GOI nested primer (10M) | 1 | primer2 (10 μM) | 0.4 |
| DNA binded Beads | 5 | DNA Template | 0.2 |
| LA Taq (5 U/ul) | 0.5 | LA Taq (5 U/ul) | 1.6 |
| rxn vol: | 50 | rxn vol: | 20 |

Example 3.1: Confirmation of Soybean Genomic Sequences

The 5' and 3' flanking borders aligned to a *Glycine max* whole genome shotgun sequence from chromosome 6, indicating that the transgene of soybean event pDAB8264.44.06.1 was inserted in soybean genome chromosome 6. To confirm the insertion site of soybean event pDAB8264.44.06.1 transgene from the soybean genome, PCR was carried out with different pairs of primers (FIG. 2 and Table 3). Genomic DNA from soybean event pDAB8264.44.06.1 and other transgenic or non-transgenic soybean lines was used as a template. Thus, to confirm if the 5' border sequences are correct, 2mepsps specific primers, for example ED_v1_C1 (SEQ ID NO:11), and two primers designed according to the cloned 5' end border sequence and/or its alignment sequence on soybean genome chromosome 6, designated 4406-WF1 (SEQ ID NO:3) and 4406-WF3 (SEQ ID NO:5), were used for amplifying the DNA segment that spans the 2mepsps gene to 5' end border sequence. Similarly, for confirmation of the cloned 3' end border sequence, a pat specific primer, for example PAT-12 (SEQ ID NO:12), and three primers designed according to the cloned 3' end border sequence, designated 4406-WR5 (SEQ ID NO:7), 4406-WR7 (SEQ ID NO:9) and 4406-WR8 (SEQ ID NO:10), were used for amplifying DNA segments that span the pat gene to 3' end border sequence. DNA fragments with predicted sizes were amplified only from the genomic DNA of soybean event pDAB8264.44.06.1 with each primer pair, one primer located on the flanking border of soybean event pDAB8264.44.06.1 and one transgene specific primer, but not from DNA samples from other transgenic soybean lines or non-transgenic control. The results indicate that the cloned 5' and 3' border sequences are the flanking border sequences of the T-strand insert for soybean event pDAB8264.44.06.1.

To further confirm the DNA insertion in the soybean genome, a PCR amplification spanning the two soybean sequences was completed. Two primers designed according to the 5' end border sequence, 4406-WF1 (SEQ ID NO:3) and 4406-WF3 (SEQ ID NO:5), and two primers for the 3' end border sequence, 4406-WR5 (SEQ ID NO:7) and 4406-WR7 (SEQ ID NO:9), were used to amplify DNA segments which contained the entire transgene, the 5' end border sequence, and the 3' border sequence. As expected, PCR amplification with the primer pair of 4406-WF1 (SEQ ID NO:3) and 4406-WR5 (SEQ ID NO:7) amplified an approximately 12 kb DNA fragment from the genomic DNA of soybean event pDAB8264.44.06.1 and a 6 kb DNA fragment from the non-transgenic soybean controls and other soybean transgenic lines. Similarly, PCR reactions completed with the primer pair of 4406-WF3 (SEQ ID NO:5) and 4406-WR7 (SEQ ID NO:9) produced an approximately 12 kb DNA fragment from the sample of soybean event pDAB8264.44.06.1 and a 6 kb DNA fragment from all the other soybean control lines, correspondingly. These results demonstrated that the transgene of soybean event pDAB8264.44.06.1 was inserted into the site of soybean genome chromosome 6. Aligning the identified 5' and 3' border sequences of soybean event pDAB8264.44.06.1 with a *Glycine max* whole genome shotgun sequence from chromosome 6 revealed about 4.4 kb deletion from the original locus. (FIG. 3).

Example 4: Soybean Event pDAB8264.44.06.1 Characterization Via Southern Blot

Southern blot analysis was used to establish the integration pattern of soybean event pDAB8264.44.06.1. These experiments generated data which demonstrated the integration and integrity of the aad-12, pat and 2mepsps v1 transgenes within the soybean genome. Soybean event pDAB8264.44.06.1 was characterized as a full length, simple integration event containing a single copy of the aad-12, pat and 2mepsps v1 PTU from plasmid pDAB8264.

Southern blot data suggested that a T-strand fragment inserted into the genome of soybean event pDAB8264.44.06.1. Detailed Southern blot analysis was conducted using a probe specific to the aad-12, pat and 2mepsps v1 insert, contained in the T-strand integration region of pDAB8264, and descriptive restriction enzymes that have cleavage sites located within the plasmid and produce hybridizing fragments internal to the plasmid or fragments that span the junction of the plasmid with soybean genomic DNA (border fragments). The molecular weights indicated from the Southern hybridization for the combination of the restriction enzyme and the probe were unique for the event, and established its identification patterns. These analyses also showed that the plasmid fragment had been inserted into soybean genomic DNA without rearrangements of the aad-12, pat and 2mepsps v1 PTU.

Example 4.1: Soybean Leaf Sample Collection and Genomic DNA (gDNA) Isolation

Genomic DNA was extracted from leaf tissue harvested from individual soybean plants containing soybean event pDAB8264.44.06.1. In addition, gDNA was isolated from a conventional soybean plant, Maverick, which contains the genetic background that is representative of the substance line, absent the aad-12 and 2mepsps v1 genes. Individual genomic DNA was extracted from lyophilized leaf tissue following the standard cetyltrimethylammonium bromide CTAB method. Following extraction, the DNA was quantified spectrofluorometrically using Pico Green reagent (Invitrogen, Carlsbad, Calif.). The DNA was then visualized on an agarose gel to confirm values from the Pico Green analysis and to determine the DNA quality.

Example 4.2: DNA Digestion and Separation

For Southern blot molecular characterization of soybean event pDAB8264.44.06.1, ten micrograms (10 μg) of genomic DNA was digested. Genomic DNA from the soybean pDAB8264.44.06.1 and non-transgenic soybean line Maverick was digested by adding approximately five units of selected restriction enzyme per μg of DNA and the corresponding reaction buffer to each DNA sample. Each sample was incubated at approximately 37° C. overnight. The restriction enzymes BstZ17I, HinDIII, NcoI, NsiI, and PacI were used individually for the digests (New England Biolabs, Ipswich, Mass.). In addition, a positive hybridization control sample was prepared by combining plasmid DNA, pDAB8264 with genomic DNA from the non-transgenic soybean variety, Maverick. The plasmid DNA/genomic DNA cocktail was digested using the same procedures and restriction enzyme as the test samples. After the digestions were incubated overnight, NaCl was added to a final concentration of 0.1M and the digested DNA samples were precipitated with isopropanol. The precipitated DNA pellet was resuspended in 20 μl of 1× loading buffer (0.01% bromophenol blue, 10.0 mM EDTA, 5.0% glycerol, 1.0 mM Tris pH 7.5). The DNA samples and molecular size markers were then electrophoresed through 0.85% agarose gels with 0.4×TAE buffer (Fisher Scientific, Pittsburgh, Pa.) at 35 volts for approximately 18-22 hours to achieve fragment separation. The gels were stained with ethidium bromide (Invitrogen, Carlsbad, Calif.) and the DNA was visualized under ultraviolet (UV) light Example 4.3: Southern Transfer and Membrane Treatment Southern blot analysis was performed essentially as described by, Memelink, J.; Swords, K.; Harry J.; Hoge, C.; (1994) Southern, Northern, and Western Blot Analysis. Plant Mol. Biol. Manual F1:1-23. Briefly, following electrophoretic separation and visualization of the DNA fragments, the gels were depurinated with 0.25M HCl for approximately 20 minutes, and then exposed to a denaturing solution (0.4 M NaOH, 1.5 M NaCl) for approximately 30 minutes followed by neutralizing solution (1.5 M NaCl, 0.5 M Tris pH 7.5) for at least 30 minutes. Southern transfer was performed overnight onto nylon membranes using a wicking system with 10×SSC. After transfer the DNA was bound to the membrane by UV crosslinking following by briefly washing membrane with a 2×SSC solution. This process produced Southern blot membranes ready for hybridization.

Example 4.4: DNA Probe Labeling and Hybridization

The DNA fragments bound to the nylon membrane were detected using a labeled probe. Probes were generated by a PCR-based incorporation of a digoxigenin (DIG) labeled nucleotide, [DIG-11]-dUTP, into the DNA fragment amplified from plasmid pDAB8264 using primers specific to gene elements. Generation of DNA probes by PCR synthesis was carried out using a PCR DIG Probe Synthesis Kit (Roche Diagnostics, Indianapolis, Ind.) following the manufacturer's recommended procedures.

Labeled probes were analyzed by agarose gel electrophoresis to determine their quality and quantity. A desired amount of labeled probe was then used for hybridization to the target DNA on the nylon membranes for detection of the specific fragments using the procedures essentially as described for DIG Easy Hyb Solution (Roche Diagnostics, Indianapolis, Ind.). Briefly, nylon membrane blots containing fixed DNA were briefly washed with 2×SSC and pre-hybridized with 20-25 mL of pre-warmed DIG Easy Hyb solution in hybridization bottles at approximately 45-55° C. for about 2 hours in a hybridization oven. The pre-hybridization solution was then decanted and replaced with approximately 15 mL of pre-warmed DIG Easy Hyb solution containing a desired amount of specific probes denatured by boiling in a water bath for approximately five minutes. The hybridization step was then conducted at approximately 45-55° C. overnight in the hybridization oven.

At the end of the probe hybridization, DIG Easy Hyb solutions containing the probes were decanted into clean tubes and stored at approximately −20° C. These probes could be reused for twice according to the manufacturer's recommended procedure. The membrane blots were rinsed briefly and washed twice in clean plastic containers with low stringency wash buffer (2×SSC, 0.1% SDS) for approximately five minutes at room temperature, followed by washing twice with high stringency wash buffer (0.1×SSC, 0.1% SDS) for 15 minutes each at approximately 65° C. The membrane blots briefly washed with 1× Malcic acid buffer from the DIG Wash and Block Buffer Set (Roche Diagnostics, Indianapolis, Ind.) for approximately 5 minutes. This was followed by blocking in a 1× blocking buffer for 2 hours and an incubation with anti-DIG-AP (alkaline phosphatase) antibody (Roche Diagnostics, Indianapolis, Ind.) in 1× blocking buffer also for a minimum of 30 minutes. After 2-3 washes with 1× washing buffer, specific DNA probes remain bound to the membrane blots and DIG-labeled DNA standards were visualized using CDP-Star Chemiluminescent Nucleic Acid Detection System (Roche Diagnostics, Indianapolis, Ind.) following the manufacturer's recommendation. Blots were exposed to chemiluminescent film for one or more time points to detect hybridizing fragments and to visualize molecular size standards. Films were developed with an All-Pro 100 Plus film developer (Konica Minolta, Osaka, Japan) and images were scanned. The number and sizes of detected bands were documented for each probe (Table 5). DIG-labeled DNA Molecular Weight Marker II (DIG MWM II) and DIG-labeled DNA Molecular Weight Marker VII (DIG MWM VII), visible after DIG detection as described, were used to determine hybridizing fragment size on the Southern blots.

TABLE 5

Length of probes used in Southern analysis of soybean event pDAB8264.44.06.1.

| Probe Name | Genetic Element | Length (bp) |
| --- | --- | --- |
| 2mEPSPS | 2mEPSPS | 1238 |
| aad-2 | aad-12 | 671 |
| specR | Spectinomycin resistance gene | 750 |
| OriRep | Ori Rep | 852 |
| trfA | Replication initiation protein trfA | 1119 |

Example 4.5: Southern Blot Results

Expected and observed fragment sizes with a particular digest and probe, based on the known restriction enzyme sites of the aad-12 and 2mepsps PTU, are given in Table 6. Expected fragment sizes are based on the plasmid map of pDAB8264 and observed fragment sizes are approximate results from these analyses and are based on the indicated sizes of the DIG-labeled DNA Molecular Weight Marker II and Mark VII fragments.

Two types of fragments were identified from these digests and hybridizations: internal fragments where known enzyme sites flank the probe region and are completely contained within the insertion region of the aad-12 and 2mepsps PTU PTU, and border fragments where a known enzyme site is located at one end of the probe region and a second site is expected in the soybean genome. Border fragment sizes vary by event because, in most cases, DNA fragment integration sites are unique for each event. The border fragments provide a means to locate a restriction enzyme site relative to the integrated DNA and to evaluate the number of DNA insertions. Southern blot analyses completed on multiple generations of soybean containing event pDAB8264.44.06.1 produced data which suggested that a low copy, intact aad-12 and 2mepsps PTU from plasmid pDAB8264 was inserted into the soybean genome of soybean event pDAB8264.44.06.1.

TABLE 6

Predicted and Observed Hybridizing Fragments in Southern Blot Analysis.

| DNA Probe | Restriction Enzymes | Samples | Expected Fragment Sizes (bp) [1] | Observed Fragment Size (bp)[2] |
|---|---|---|---|---|
| aad-12 | BstZ17I | pDAB8264 | 4994 | ~5000 |
| | | Maverick | none | none |
| | | Soybean Event pDAB8264.44.06.1 | 4994 | ~5000 |
| | Hind III | pDAB8264 | 4731 | ~4700 |
| | | Maverick | none | none |
| | | Soybean Event pDAB8264.44.06.1 | >4078 | ~7400 |
| | Nco I | pDAB8264 | 7429 | ~7400 |
| | | Maverick | none | none |
| | | Soybean Event pDAB8264.44.06.1 | >3690 | ~3800 |
| | Nsi I | pDAB8264 | 4974 | ~5000 |
| | | Maverick | none | none |
| | | Soybean Event pDAB8264.44.06.1 | 4974 | ~5000 |
| | Pac I | pDAB8264 | 6768 | ~6800 |
| | | Maverick | none | none |
| | | Soybean Event pDAB8264.44.06.1 | 6768 | ~6800 |
| 2mEPSPS | BstZ17I | pDAB8264 | 11024 | ~11000 |
| | | Maverick | none | none |
| | | Soybean Event pDAB8264.44.06.1 | >4858 | ~16000 |
| | Nco I | pDAB8264 | 5203 | ~5200 |
| | | Maverick | none | none |
| | | Soybean Event pDAB8264.44.06.1 | >3756 | ~6100 |
| | Nsi I | pDAB8264 | 11044 | 11000 |
| | | Maverick | none | |
| | | Soybean Event pDAB8264.44.06.1 | >5199 | ~5300 |
| | Pac I | pDAB8264 | 6768 | ~6800 |
| | | Maverick | none | none |
| | | Soybean Event pDAB8264.44.06.1 | 6768 | ~6800 |

TABLE 6-continued

Predicted and Observed Hybridizing Fragments in Southern Blot Analysis.

| DNA Probe | Restriction Enzymes | Samples | Expected Fragment Sizes (bp) [1] | Observed Fragment Size (bp)[2] |
|---|---|---|---|---|
| SpecR | Hind III | pDAB8264 | 9322 | ~9300 |
| | | Maverick | none | none |
| | | Soybean Event pDAB8264.44.06.1 | none | none |
| OriRep + trfA | Pac I | pDAB8264 | 9210 | ~9200 |
| | | Maverick | none | none |
| | | Soybean Event pDAB8264.44.06.1 | none | none |

The restriction enzymes NcoI and HinD III bind and cleave unique restriction sites in plasmid pDAB8264. Subsequently, these enzymes were selected to characterize the aad-12 gene insert in soybean event pDAB8264.44.06.1. Border fragments of greater than 4,078 bp or greater than 3,690 bp were predicted to hybridize with the probe following HinD III and NcoI digests, respectively (Table 6). Single aad-12 hybridization bands of approximately 7,400 bp and approximately 3,800 bp were observed when HinDIII and NcoI were used, respectively. The hybridization of the probe to bands of this size suggests the presence of a single site of insertion for the aad-12 gene in the soybean genome of soybean event pDAB8264.44.06.1. Restriction enzymes BstZ17I, NsiI and PacI was selected to release a fragment which contains the aad-12 plant transcription unit (PTU; promoter/gene/terminator) (Table 6). The predicted approximately 5,000, approximately 5,000, and approximately 6,800 bp fragments were observed with the probe following BstZ17I, NsiI and PacI digestions, respectively. Results obtained with the enzyme digestion of the pDAB8264.44.06.1 samples followed by probe hybridization indicated that an intact aad-12 PTU from plasmid pDAB8264 was inserted into the soybean genome of soybean event pDAB8264.44.06.1. In addition, the molecular weight sizes of the hybridization bands produced for the HinDIII, NcoI, NsiI, and BstZ17I restriction fragments indicate that the aad-12 PTU also contained the linked pat PTU.

The restriction enzymes BstZ17I, NcoI and NsiI bind and cleave restriction sites in plasmid pDAB8264. Subsequently, these enzymes were selected to characterize the 2mepsps gene insert in soybean event pDAB8264.44.06.1. Border fragments of greater than 4,858 bp, greater than 3,756, or greater than 5,199 bp were predicted to hybridize with the probe following the BstZ17I, NcoI and NsiI digests respectively (Table 6). Single 2mepsps hybridization bands of approximately 16,000 bp, approximately 6,100 bp and approximately 5,300 bp were observed when BstZ17I, NcoI and NsiI were used, respectively. The hybridization of the probe to bands of this size suggests the presence of a single site of insertion for the 2mepsps gene in the soybean genome of soybean event pDAB8264.44.06.1. Restriction enzyme PacI was selected to release a fragment which contains the 2mepsps plant transcription unit (PTU; promoter/gene/terminator) (Table 6). The predicted approximately 6,800 bp fragment was observed with the probe following the PacI digestions. Results obtained with the enzyme digestion of the pDAB8264.44.06.1 sample followed by probe hybridization indicated that an intact 2mepsps PTU from plasmid pDAB8264 was inserted into the soybean genome of soybean event pDAB8264.44.06.1.

Example 4.6: Absence of Backbone Sequences

Southern blot analysis was also conducted to verify the absence of the spectinomycin resistance gene (specR), Ori Rep element and replication initiation protein trfA (trf A element) in soybean event pDAB8264.44.06.1. No specific hybridization to spectinomycin resistance, Ori Rep element or trf A element is expected when appropriate positive (pDAB8264 plus Maverick) and negative (Maverick) controls are included for Southern analysis. Following Hind III digestion and hybridization with specR specific probe, one expected size band of approximately 9,300 bp was observed in the positive control sample (pDAB8264 plus maverick) but absent from samples of the negative control and soybean event pDAB8264.44.06.1. Similarly, one expected size band of approximately 9,200 bp was detected in the positive control sample (pDAB8264 plus maverick) but absent from the samples of the negative control and soybean event pDAB8264.44.06.1 after Pac I digestion and hybridization with mixture of OriRep specific probe and trfA specific probe. These data indicate the absence of spectinomycin resistance gene, Ori Rep element and replication initiation protein trfA in soybean event pDAB8264.44.06.1.

Example 5: Agronomic, Yield and Herbicide Tolerance Evaluation

The agronomic characteristics and herbicide tolerance of soybean Event pDAB8264.44.06.1 were studied in yield trials at multiple geographical locales during a single growing season. No agronomically meaningful unintended differences were observed between soybean Event pDAB8264.44.06.1 and the Maverick control plants. The results of the study demonstrated that soybean Event pDAB8264.44.06.1 was agronomically equivalent to the Maverick control plants. In addition, soybean Event pDAB8264.44.06.1 provided robust herbicide tolerance when sprayed with a tankmix of glyphosate and 2,4-D.

The following agronomic characteristics were measured and recorded for all test entries at each location.

1.) Emergence: Calculated by dividing Stand count by number of seeds planted in a one meter section and multiplying by 100.
2.) Seedling Vigor at V1: Vigor is an overall estimate of the health of the plot. Results were rated on a scale of 0-100% with 0% representing a plot with all dead plants and 100% representing plots that look very healthy.
3.) Rated overall visual crop injury, chlorosis and necrosis at 1 day, 7 days, and 14 days after V3 chemical application. Observations were made for any signs of epinasty which is typical of 2,4-D injury. Epinasty is exhibited as twisting or drooping of leaves and stems. All crop injuries used a 0 to 100% scale, where 0% indicates no injury and 100% indicates complete plant death.
4.) Flowering date: This measurement records the date when 50% of the plants in the plot begin to flower. The number of days from planting to when 50% of the plants in each plot were flowering was recorded.
5.) Stand count at R2 or R1: Is a visual estimate of the average vigor of plants in each plot, determined by counting the number of plants in a representative one meter section of one row per plot, and taking note at the R2 or R1 growth stage.
6.) Rated overall visual crop injury, chlorosis and necrosis at 1 day, 7 days, and 14 days after R2 chemical application. Observations were made for any signs of epinasty which is typical of 2,4-D injury. Epinasty is exhibited as twisting or drooping of leaves and stems. All crop injuries used a 0 to 100% scale where 0% indicates no injury and 100% indicates complete plant death.
7.) Disease incidence at R6 growth stage: Is a visual estimate of disease incidence used to record the severity of disease in the plot. Rated on a scale of 0-100%. Where 0% indicates no disease present and 100% indicates all plants in plot had disease.
8.) Insect damage at R6 growth stage: Is a visual estimate of insect damage used to record the severity of insect damage in the plot. Recorded the percentage of plant tissue in the plot damaged by insects using a 0-100% scale. Where 0% indicates no insect damage present and 100% indicates all plants in plot had insect damage.
9.) Plant height at senescence: The average height of the plants in each plot was recorded. Plants were measured from the soil surface to the tip after the leaves had fallen. Measurements were recorded in centimeters. If the plot was lodged, a representative group of plants were stood-up to obtain a measurement.
10.) Days to maturity. Recorded date when 95% of the pods in a plot reached physiological maturity and the plants were a dry down color. The numbers of days to elapse since planting were calculated.
11.) Lodging: Recorded a visual estimate of lodging severity at harvest time. Recorded on a 0 to 100% scale, where 0% indicates no lodging and 100% indicates all plants in a plot flat on the ground.
12.) Shattering: Recorded a visual estimate of pod shattering at harvest time. Recorded as an estimate of percentage of pods shattered per plot. 0-100% scale with 0% indicating no shattering and 100% indicating all pods shattered.
13.) Yield: Recorded the weight of grain harvested from each plot. Harvested the entire 2 row plot and recorded seed weight and moisture. Calculations of bu/acre were made by adjusting to 13% moisture.
14.) 100 seed weight: For each plot 100 seeds were counted out and the weight was recorded in grams.

Herbicide tolerance of soybean Event pDAB8264.44.06.1 was assessed following the application of a tankmix of 2,4-D and glyphosate at 2,185 g ae/ha mixed with 2% weight per weight ammonium sulfate (AMS). The herbicides were sprayed as a V3/R2 sequential herbicide treatment. This herbicide treatment was completed by spraying soybean plants at the V3 growth stage of development followed by a second sequential application at the R2 growth stage of development. The V3 growth stage is characterized when the unifoliolate and first three trifoliolate leaves are fully developed. The R2 growth stage is characterized by a single open flower at one of the two uppermost nodes on the main stem with a fully developed leaf.

These trials were set up using a randomized complete block design with four replications for every treatment. Each plot was 2 rows wide and rows were spaced 30 inches apart. Plots were planted to a total length of 12.5 ft with a 2.5 to 3.0 ft alley between plots. Maverick control plants were expected to die from herbicide applications so they were grown in a separate plot; away from the transgenic soybean plant rows.

The results of soybean Event pDAB8264.44.06.1 sprayed with the 2,4-D and glyphosate herbicide tank mix as compared to unsprayed soybean Event pDAB8264.44.06.1 are summarized. Table 7 presents the means from an analysis comparing soybean Event pDAB8264.44.06.1 sprayed with a tankmix of 2,4-D and glyphosate to unsprayed soybean Event pDAB8264.44.06.1. The herbicide application did not damage soybean Event pDAB8264.44.06.1, these plants performed equivalently as compared to unsprayed soybean Event pDAB8264.44.06.1 plants for the reported agronomic characteristics listed in Table 7. With the exception of some early transient injury 1 and 7 daa (days after application) at the V3 stage of development and at 1, 7 and 14 daa at the R2 stage of development, soybean Event pDAB8264.44.06.1 showed robust tolerance to the 2,4-D and glyphosate tank mix. In contrast, none of the Maverick plants were surviving after being sprayed with the herbicide treatment.

TABLE 7

Comparison of soybean Event pDAB8264.44.06.1 sprayed and unsprayed with a tank mix of 2,4-D glyphosate.

soybean Event pDAB8264.44.06.1

| Trait: Agronomic Characteristics | Sprayed | Non-sprayed |
|---|---|---|
| Emergence (%) | 90.2 | 84.0 |
| Vigor V1-V3 (%) | 93.4 | 88.4 |
| Rated overall visual crop injury after V3 herbicide application; Injury 1 daa (%) | 1.3 | 0.0 |
| Rated overall visual crop injury after V3 herbicide application; Injury 7 daa (%) | 1.1 | 0.0 |
| Rated overall visual crop injury after V3 herbicide application; 14 daa (%) | 0.0 | 0.0 |
| Days to flower (days from planting) | 38.6 | 38.5 |
| Stand count R2 | 26.1 | 22.5 |
| Rated overall visual crop injury after R2 herbicide application; Injury 1 daa (%) | 2.8 | 0.4 |
| Rated overall visual crop injury after R2 herbicide application; Injury 7 daa (%) | 2.8 | 0.0 |
| Rated overall visual crop injury after R2 herbicide application; Injury 14 daa (%) | 1.7 | 0.1 |
| Disease incidence (%) | 1.5 | 1.2 |
| Insect damage (%) | 6.9 | 7.6 |
| Height (cm) | 112.3 | 110.3 |
| Maturity (days from planting) | 114.0 | 113.7 |
| Lodging (%) | 16.4 | 18.1 |
| Shattering (%) | 0.1 | 0.1 |
| Yield (bu/acre) | 44.8 | 43.9 |
| 100 seed weight (g) | 12.3 | 12.1 |

Agronomic equivalence of soybean Event pDAB8264.44.06.1 as compared to the control line, Maverick, was assessed. These trials were set up using a block design with two replications. Each plot was 2 rows wide and rows were spaced 30 inches apart. Plots were planted to a total length of 12.5 ft with a 2.5 to 3.0 foot alley between plots.

Table 8 presents the means from the analysis comparing the agronomic equivalence of soybean Event pDAB8264.44.06.1 with the control line, Maverick. The agronomic data is indicative that soybean Event pDAB8264.44.06.1 performs equivalently to Maverick plants, and does not result in agronomically meaningful unintended differences.

TABLE 8

Comparison of soybean Event pDAB8264.44.06.1 to Maverick control lines in yield trials.

| | Maverick | | pDAB8264.44.06.1 | |
|---|---|---|---|---|
| Emergence (%) | 86.2 | A | 83.2 | A |
| Vigor V1 (1 poor-9 good) | 91.0 | A | 89.7 | A |
| Days to flower (days from planting) | 41.2 | A | 40.7 | A |
| Stand count R1 | 22.7 | A | 22.2 | A |
| Disease incidence (%) | 1.8 | A | 2.1 | A |
| Insect damage (%) | 7.8 | A | 8.0 | A |
| Height (cm) | 110.3 | A | 112.3 | A |
| Maturity (days from planting) | 119.7 | A | 119.1 | A |
| Lodging (%) | 16.1 | B | 20.6 | A |
| Shattering | 0.2 | A | 0.4 | A |
| Yield (bu/acre) | 45.7 | A | 43.7 | A |
| 100 seed weight | 13.2 | A | 12.6 | B |

For each trait values not followed by the same letter are different according to Student's T-distribution statistical analysis.

Example 6: Event Specific TaqMan Assay

Two event specific TAQMAN assays were developed to detect the presence of soybean event pDAB8264.44.06.1 and to determine zygosity status of plants in breeding populations. Soybean event pDAB8264.44.06.1 contains the T-strand of the binary vector pDAB8264 (FIG. 1). For specific detection of soybean event pDAB8264.44.06.1, specific Taqman primers and probes were designed according to the DNA sequences located in the 5' (SEQ ID NO:14) or 3' (SEQ ID NO:15) insert-to-plant junction (FIG. 4). One event specific assay for soybean event pDAB8264.44.06.1 was designed to specifically detect a 98 bp DNA fragment (SEQ ID NO:16) that spans the 5' integration junction using two primers and a target-specific MGB probe synthesized by Applied Biosystems (ABI) containing the FAM reporter at its 5'end. Another event specific assay for soybean event pDAB8264.44.06.1 was designed to specifically target a 131 bp DNA fragment (SEQ ID NO:17) that spans the 3' integration junction using two specific primers and a target-specific MGB probe synthesized by ABI containing the FAM reporter at its 5'end. Specificity of this Taqman detection method for soybean event pDAB8264.44.06.1 was tested against 11 different events which contain the 2mEPSPS and aad-12 PTUs and a control non-transgenic soybean variety (Maverick) in duplex format with the soybean specific endogenous reference gene, GMFL01-25-J19 (*Glycine max* cDNA, GenBank: AK286292.1).

Example 6.1: gDNA Isolation gDNA samples of 11 different soybean events and non-transgenic soybean varieties were tested in this study. Genomic DNA was extracted using modified Qiagen MagAttract plant DNA kit (Qiagen, Valencia, Calif.). Fresh soybean leaf discs, 8 per sample, were used for gDNA extraction. The gDNA was quantified with the Pico Green method according to vendor's instructions (Molecular Probes, Eugene, Oreg.). Samples were diluted with DNase-free water resulting in a concentration of 10 ng/μL for the purpose of this study.

Example 6.2: Taqman Assay and Results

Specific Taqman primers and probes were designed for a soybean event pDAB8264.44.06.1 specific Taqman assay. These reagents can be used with the conditions listed below to detect the transgene within soybean event pDAB8264.44.06.1. Table 9 lists the primer and probe sequences that were developed specifically for the detection of soybean event pDAB8264.44.06.1.

TABLE 9

Taqman PCR Primers and Probes.

| SEQ ID NO: | Name | Description | Sequence |
|---|---|---|---|
| *Event Target Reaction* | | | |
| SEQ ID NO: 18 | 4406_5'F | Event specific forward Primer | TTGTTCTTGTTGTTTCCTCTTTAGGA |
| SEQ ID NO: 19 | 4406_5'R | Event specific reverse Primer | GACCTCAATTGCGAGCTTTCTAAT |
| SEQ ID NO: 20 | 4406_5'P | Event specific probe used with 4406_5'F and 4406_5'R | 5'FAM/CATGGAGGTCCGAATAG-MGB |
| SEQ ID NO: 21 | 4406_3'F | Event specific forward Primer | AAACGTCCGCAATGTGTTATTAAG |
| SEQ ID NO: 22 | 4406_3'R | Event specific reverse Primer | CGTTGCCTTGTTCCACATATCA |
| SEQ ID NO: 23 | 4406_3'P | Event specific probe used with 4406_3'F and 4406_3'R | 5'FAM/ACAGAGAACGAATGTC-MGB |
| *Reference System Reaction* | | | 5' to 3' sequence |
| SEQ ID NO: 24 | GMS116 F | Forward Primer | GTAATATGGGCTCAGAGGAATGGT |
| SEQ ID NO: 25 | GMS116 R | Reverse Primer | ATGGAGAAGAACATTGGAATTGC |
| SEQ ID NO: 26 | GMS116 Probe | Probe | 5'HEX/CCATGGCCCGGTACCATCTGGTC/3BHQ_1/3' |

The multiplex PCR conditions for amplification are as follows: 1× Roche PCR Buffer, 0.4 µM event specific forward primer, 0.4 µM event specific reverse primer, 0.4 µM Primer GMS116 F, 0.4 µM Primer GMS116 R, 0.2 µM Event specific probe, 0.2 µM GMS116 Probe, 0.1% PVP, 20 ng gDNA in a total reaction of 10 The cocktail was amplified using the following conditions: i) 95° C. for 10 min., ii) 95° C. for 10 sec, iii) 60° C. for 30 sec, iv) 72° C. for 1 sec v) repeat step ii-iv for 35 cycles, v) 40° C. hold. The Real time PCR was carried out on the Roche LightCycler 480. Data analysis was based on measurement of the crossing point (Cp value) determined by LightCycler 480 software, which is the PCR cycle number when the rate of change in fluorescence reaches its maximum.

The Taqman detection method for soybean event pDAB8264.44.06.1 was tested against 11 different events which contain the 2mEPSPS and aad-12 PTUs and non-transgenic soybean varieties in duplex format with soybean specific endogenous reference gene, GMFL01-25-J19 (GenBank: AK286292.1). The assays specifically detected the soybean event pDAB8264.44.06.1 and did not produce or amplify any false-positive results from the controls (i.e. the 11 different events which contain the 2mEPSPS and aad-12 PTUs and non-transgenic soybean varieties). The event specific primers and probes can be used for the detection of the soybean event pDAB8264.44.06.1 and these conditions and reagents are applicable for zygosity assays.

Example 7: Full Length Sequence of Soybean Event pDAB8264.44.06.1

SEQ ID NO:27 provides the full length sequence of soybean Event pDAB8264.44.06.1. This sequence contains the 5' genomic flanking sequence, the integrated T-strand insert from pDAB8264 and the 3' genomic flanking sequence. With respect to SEQ ID NO:27, residues 1-1494 are 5' genomic flanking sequence, residues 1495-1497 are a three base pair insertion, residues 1498-11,774 are the pDAB8264 T-strand insert, and residues 11,775-13,659 are 3' flanking sequence. The junction sequence or transition with respect to the 5' end of the insert thus occurs at residues 1494-1495 of SEQ ID NO:27. The junction sequence or transition with respect to the 3' end of the insert thus occurs at residues 11,774-11,775 of SEQ ID NO:27. SEQ ID NO:27 is the polynucleotide sequence of soybean Event pDAB8264.44.06.1 and was assembled from an alignment of multiple PCR contigs which were produced via PCR amplification reactions and sequenced using the ABI Big Dye® Terminator sequencing reaction kit (Applied Biosystems, Foster City, Calif.).

Example 8: Breeding Stack of Soybean Event pDAB8264.44.06.1 and Soybean Insect Tolerant Event pDAB9582.812.9.1

Example 8.1: Sexual Crossing of Soybean Event pDAB8264.44.06.1 and Soybean Insect Tolerant Event pDAB9582.812.9.1

Soybean event pDAB8264.44.06.1 was sexually crossed with soybean event pDAB9582.812.9.1. The anthers of soybean event pDAB8264.44.06.1 were manually rubbed across the stigma of soybean event pDAB9582.812.9.1, thereby fertilizing soybean event pDAB9582.812.9.1. The resulting F1 progeny which contained integration events from both soybean event pDAB9582.812.9.1 and soybean event pDAB8264.44.06.1 were screened for tolerance to 2,4-D and glyphosate herbicides to identify progeny plants which contained both integration events. Next, the F1 progeny plants were self-fertilized to produce an F2 offspring which was confirmed to segregate independently for both events. The F2 plants were sprayed with a single herbicide application containing both 2,4-D (1120 g ae/ha) and glyphosate (1120 g ae/ha). The resulting F2 plants were screened using a Taqman zygosity based assay to identify plants that were homozygous for both events. Selfing of these F2 homozygous plants produced an F3 offspring that were homozygous for both soybean event pDAB9582.812.9.1 and soybean event pDAB8264.44.06.1. The resulting event was labeled as soybean event pDAB9582.812.9.1::pDAB8264.44.06.1.

Example 8.2: Determination of the Zygosity Status of Soybean Event pDAB9582.812.9.1::pDAB8264.44.06.1

To determine the zygosity status of plants produced from the breeding cross of soybean event pDAB8264.44.06.1 and soybean event pDAB9582.812.9.1, separate event specific TAQMAN® assays were developed to detect the presence of either the pDAB9582.812.9.1 or pDAB8264.44.06.1 integration events. Segregating F2 plants, produced from the self fertilization of a breeding cross of soybean event pDAB9582.812.9.1 and soybean event pDAB8264.44.06.1, were tested with these event specific TAQMAN® assays to identify individual plants which contained both soybean event pDAB9582.812.9.1 and soybean event pDAB8264.44.06.1, and were homozygous for both events.
gDNA Isolation gDNA samples from segregating F2 plants of the breeding stack of soybean event pDAB9582.812.9.1::pDAB8264.44.06.1 were tested in this study. Fresh soybean leaf discs, 4 per plant, were collected from 3,187 segregating F2 plants of the breeding stack of soybean event pDAB9582.812.9.1::pDAB8264.44.06.1. Genomic DNA was extracted from these samples using a modified Qiagen MagAttract Plant DNA Kit® (Qiagen, Valencia, Calif.).
TAQMAN® Assay and Results TAQMAN® primers and probes as previously described were designed for the use of individual event specific assays for soybean events pDAB9582.812.9.1 (U.S. Provisional Application No. 61/471,845) and pDAB8264.44.06.1 (described above). These reagents were used with the conditions listed below to determine the zygosity of each integration event contained within the breeding stack of soybean event pDAB9582.812.9.1::pDAB8264.44.06.1.

The multiplex PCR conditions for amplification are as follows: 1× Roche PCR Buffer, 0.4 µM event pDAB8264.44.06.1 specific forward primer, 0.4 µM event pDAB8264.44.06.1 specific reverse primer 0.4 µM event pDAB9582.812.9.1 specific forward primer, 0.4 µM event pDAB9582.812.9.1 specific reverse primer, 0.4 µM Primer GMS116 F, 0.4 µM Primer GMS116 R, 0.2 µM Event pDAB9582.812.9.1 specific probe, 0.2 µM Event pDAB8264.44.06.1 specific probe, 0.2 µM GMS116 Probe, 0.1% PVP, 20 ng gDNA in a total reaction of 10 µl. The cocktail was amplified using the following conditions: i) 95° C. for 10 min., ii) 95° C. for 10 sec, iii) 60° C. for 30 sec, iv) 72° C. for 1 sec v) repeat step ii-iv for 35 cycles, v) 40° C. hold. The Real time PCR was carried out on the Roche LightCycler® 480. Data analysis was based on measurement of the crossing point (Cp value) determined by LightCycler® 480 software, which is the PCR cycle number when the rate of change in fluorescence reaches its maximum.

A total of 3,187 segregating F2 plants, produced from the breeding cross of soybean event pDAB9582.812.9.1 and soybean event pDAB8264.44.06.1 were tested with the event specific TAQMAN® assays to determine the zygosity of individual plants for both soybean event pDAB9582.812.9.1 and soybean event pDAB8264.44.06.1. The results from these assays indicated that soybean event pDAB9582.812.9.1 and soybean event pDAB8264.44.06.1 were both present and detected in 2,360 plants. The zygosity status (also described as ploidy level) of each integration event is indicated in Table 9b. Of the 2,360 identified plants, 237 were determined to contain two copies of soybean event pDAB9582.812.9.1 and soybean event pDAB8264.44.06.1.

TABLE 9b

Event specific TAQMAN® zygosity analysis of the breeding stack of soybean event pDAB9582.812.9.1::pDAB8264.44.06.1

| Zygosity status for pDAB9582.812.9.1::pDAB8264.44.06.1 | Number of plants |
|---|---|
| Homozygous::Homozygous | 237 |
| Homozygous::Hemizygous | 506 |
| Homozygous::Null | 287 |
| Hemizygous::Homozygous | 542 |
| Hemizygous::Hemizygous | 1075 |
| Hemizygous::Null | 540 |

Example 8.3: Characterization of Protein Expression in the Breeding Stack of Soybean Event pDAB9582.812.9.1::pDAB8264.44.06.1

The biochemical properties of the recombinant Cry1F, Cry1Ac, AAD12, 2mEPSPS, and PAT proteins expressed in the breeding stack of soybean event pDAB9582.812.9.1::pDAB8264.44.06.1 were characterized. An Enzyme Linked Immunosorbent Assay (ELISA) was used to quantify the expression of PAT. Comparatively, Cry1Ac/Cry1F and AAD12/2mEPSPS proteins were quantified by multiplexed immunoassays utilizing electrochemiluminescent technology from Meso-Scale Discovery (MSD, Gaithersburg, Md.). Collectively, these assays were used to characterize biochemical properties and confirm the robust expression of these proteins in the breeding stack of soybean event pDAB9582.812.9.1::pDAB8264.44.06.1.
Expression of the PAT Protein in Plant Tissues Levels of PAT protein were determined in the breeding stack of F3 soybean event pDAB9582.812.9.1::pDAB8264.44.06.1 which were identified to be homozygous for both event pDAB9582.812.9.1 and event pDAB8264.44.06.1 integrations. The levels of PAT protein expressed from soybean event pDAB9582.812.9.1::pDAB8264.44.06.1 was compared to the parental events, soybean event pDAB9582.812.9.1 and soybean event pDAB8264.44.06.1.

The soluble, extractable PAT protein was obtained from soybean leaf tissue and measured using a quantitative ELISA method (APS 014, Envirologix, Portland, Me.). Samples of soybean leaf tissues were isolated from greenhouse grown test plants at the unifoliate to V1 stage and prepared for expression analysis. The PAT protein was extracted from soybean plant tissues with a phosphate buffered saline solution containing the detergent Tween-20 (PBST) and 1% polyvinylpyrrolidone 40 (PVP-40). The samples were then extracted using a GenoGrinder® at 1500 rpm for 5 minutes. The plant extract was centrifuged; the aqueous supernatant was collected, diluted with appropriate buffer as necessary, and analyzed using the PAT ELISA kit in a sandwich format. The kit was used following the manufacturer's suggested protocol (Envirologix, Portland, Me.).

Detection analysis was performed to investigate the expression and heritability of soybean event pDAB9582.812.9.1::pDAB8264.44.06.1. The F3 generation of the breeding stack, soybean event pDAB9582.812.9.1::

pDAB8264.44.06.1 expressed PAT at higher concentrations than either the parental events, pDAB9582.812.9.1 and pDAB8264.44.06.1. The increased concentration of PAT in soybean event pDAB9582.812.9.1::pDAB8264.44.06.1 breeding stack was expected. The higher concentrations of PAT are a result of soybean event pDAB9582.812.9.1::pDAB8264.44.06.1 containing twice as many copies of the pat coding sequence as compared to either of the parental events (Table 10).

TABLE 10

Average PAT protein expression from soybean event pDAB9582.812.9.1::pDAB8264.44.06.1, and parental events (soybean event pDAB9582.812.9.1 and soybean event pDAB8264.44.06.1).

| Soybean Event | Average PAT Expression (ng/cm$^2$) |
| --- | --- |
| pDAB9582.812.9.1::pDAB8264.44.06.1 | 38.0 |
| pDAB9582.812.9.1 | 11.0 |
| pDAB8264.44.06.1 | 13.3 |

Expression of the Cry1F and Cry1Ac Proteins in Plant Tissues

Levels of Cry1F and Cry1Ac protein were determined in the breeding stack of F3 soybean event pDAB9582.812.9.1::pDAB8264.44.06.1 which were identified to be homozygous for both event pDAB9582.812.9.1 and event pDAB8264.44.06.1 integrations. The levels of Cry1F and Cry1Ac protein expressed from soybean event pDAB9582.812.9.1::pDAB8264.44.06.1 was compared to the parental event, soybean event pDAB9582.812.9.1.

The soluble, extractable Cry1F and Cry1Ac protein was obtained from soybean leaf tissue and measured using a multiplexed electrochemiluminescent MSD assay. Samples of soybean leaf tissue were isolated from greenhouse grown plants at the unifoliate to V1 stage and prepared for expression analysis. The Cry1F and Cry1Ac protein was extracted from soybean plant tissues with a phosphate buffered saline solution containing the detergent Tween-20 (PBST) and 1% polyvinylpyrrolidone 40 (PVP-40). The samples were then extracted using a GenoGrinder® at 1500 rpm for 5 minutes. The plant extract was centrifuged; the aqueous supernatant was collected, diluted with appropriate buffer as necessary, and analyzed using a Cry1F/Cry1Ac multiplex MSD assay from Meso-Scale Discovery. The kit was used following the manufacturer's suggested protocol.

Detection analysis was performed to investigate the expression and heritability of soybean event pDAB9582.812.9.1::pDAB8264.44.06.1. The F3 generation of the breeding stack of soybean event pDAB9582.812.9.1::pDAB8264.44.06.1 expressed Cry1F and Cry1 Ac proteins at concentrations higher than the parental soybean event pDAB9582.812.9.1. (Table 11). These results indicate that soybean event pDAB9582.812.9.1::pDAB8264.44.06.1 plants contained a functionally expressing copy of the cry1F and cry1Ac coding sequences which were inherited from the parental line, soybean event pDAB9582.812.9.1.

TABLE 11

Average Cry1Ac and Cry1F protein expression from soybean event pDAB9582.812.9.1::pDAB8264.44.06.1 as compared to parental event pDAB9582.812.9.1

| Soybean Event | Average Cry1Ac Expression (ng/cm$^2$) | Average Cry1F Expression (ng/cm$^2$) |
| --- | --- | --- |
| pDAB9582.812.9.1::pDAB8264.44.06.1 | 27.1 | 140.5 |
| pDAB9582.812.9.1 | 20.8 | 112.9 |

Expression of the AAD12 and 2mEPSPS Proteins in Plant Tissues

Levels of AAD12 and 2mEPSPS protein were determined in the breeding stack of F3 soybean event pDAB9582.812.9.1::pDAB8264.44.06.1 which were identified to be homozygous for both event pDAB9582.812.9.1 and event pDAB8264.44.06.1 integrations. The levels of AAD12 and 2mEPSPS protein expressed from soybean event pDAB9582.812.9.1::pDAB8264.44.06.1 was compared to the parental event, Soybean Event pDAB8264.44.06.1.

The soluble, extractable AAD12 and 2mEPSPS protein was obtained from soybean leaf tissue and measured using a multiplexed electrochemiluminescent MSD assay. Samples of soybean leaf tissue were isolated from greenhouse grown plants at the unifoliate to V1 stage and prepared for expression analysis. The AAD12 and 2mEPSPS protein was extracted from soybean plant tissues with a phosphate buffered saline solution containing the detergent Tween-20 (PBST) and 1% polyvinylpyrrolidone 40 (PVP-40). The samples were then extracted using a GenoGrinder® at 1500 rpm for 5 minutes. The plant extract was centrifuged; the aqueous supernatant was collected, diluted with appropriate buffer as necessary, and analyzed using a AAD12 and 2mEPSPS multiplex MSD assay from Meso-Scale Discovery. The kit was used following the manufacturer's suggested protocol.

Detection analysis was performed to investigate the expression and heritability of soybean event pDAB9582.812.9.1::pDAB8264.44.06.1. The F3 generation of the breeding stack of soybean event pDAB9582.812.9.1::pDAB8264.44.06.1 expressed AAD12 and 2mEPSPS proteins at concentrations higher than the parental soybean event pDAB8264.44.06.1. (Table 12). These results indicated that soybean event pDAB9582.812.9.1::pDAB8264.44.06.1 plants contained a functionally expressing copy of the aad-12 and 2mEPSPS coding sequences which were inherited from the parental line, soybean event pDAB8264.44.06.1.

TABLE 12

Average AAD12 and 2mEPSPS protein expression from soybean event pDAB9582.812.9.1::pDAB8264.44.06.1 as compared to parental soybean event pDAB8264.44.06.1

| Soybean Event | Average AAD12 Expression (ng/cm$^2$) | Average 2mEPSPS Expression (ng/cm$^2$) |
| --- | --- | --- |
| pDAB9582.812.9.1::pDAB8264.44.06.1 | 479.7 | 410.3 |
| pDAB8264.44.06.1 | 320.4 | 328.9 |

Example 8.4: Herbicide Tolerance of the Breeding Stack of Soybean Event pDAB9582.812.9.1::pDAB8264.44.06.1

Herbicide tolerance of the breeding stack, soybean event pDAB9582.812.9.1::pDAB8264.44.06.1 was assayed during two growing seasons. Soybean event pDAB9582.812.9.1::pDAB8264.44.06.1 seed were planted and grown to maturity. Mature plants were sprayed with a single herbicide application which consisted of a combination of 2,4-D and glyphosate. The resulting tolerance to these herbicides was measured by counting the number of surviving plants. Comparatively, control plants which did not contain the aad-12 and 2mEPSPS genes and were expected to be susceptible to the application of the 2,4-D and glyphosate herbicides were included in the study.

During the first season, herbicide tolerance was assessed in 120 field grown plots of F2 segregating lineages of the breeding stack of soybean event pDAB9582.812.9.1::pDAB8264.44.06.1. Each plot was 1 row wide and rows were spaced 30 inches apart. Plots were planted on 12 foot centers (total planted length 7.5 feet) with a 4.5 foot alley between plots. A total of 4,364 plants from F2 segregating lineages of the breeding stack of soybean event pDAB9582.812.9.1::pDAB8264.44.06.1 were sprayed with a mixture of 2,4-D and glyphosate (1120 g ae/ha). A single spray application of the glyphosate/2,4-D herbicides was made between V3 and V4 growth stages. The V3 growth stage is characterized by the unifoliate and first three trifoliate leaves being fully developed and the V4 growth stage is characterized by the unifoliate and first four trifoliate leaves being fully developed. After the herbicide treatment was completed, the plots were observed and 3,234 plants were identified as being tolerant to the application of the herbicides. The soybean event pDAB9582.812.9.1::pDAB8264.44.06.1 plants which were susceptible to the herbicide application did not contain copies of the aad-12 and 2mEPSPS as a result of Mendelian segregation of the pDAB8264.44.06.1 integration event.

During the second season, herbicide tolerance was assessed in greenhouse grown F3 homozygous plants of soybean event pDAB9582.812.9.1::pDAB8264.44.06.1. The soybean plants were grown in 4 inch pots which contained one plant per pot. A total of 15, F3 homozygous plants were sprayed with a single application of 2,4-D and glyphosate (840 ae/ha). All 15 plants survived after being sprayed with the herbicides, indicating that the soybean event pDAB9582.812.9.1::pDAB8264.44.06.1 plants were tolerant to the application of the herbicides, glyphosate and 2,4-D.

In summary, the aad-12 and 2mEPSPS genes which were present in the soybean event pDAB8264.44.06.1 parental line conferred tolerance to 2,4-D and glyphosate herbicides. These traits were passed and inherited in soybean event pDAB9582.812.9.1::pDAB8264.44.06.1, thereby providing herbicidal tolerance to soybean event pDAB9582.812.9.1::pDAB8264.44.06.1. Comparatively, control plants which did not contain the aad-12 and 2mEPSPS genes were susceptible to the application of the 2,4-D and glyphosate herbicides.

Example 8.5: Characterization of Insecticidal Activity of Soybean Event pDAB9582.812.9.1::pDAB8264.44.06.1

Greenhouse evaluations were conducted to characterize the insecticidal tolerance of the breeding stack of soybean event pDAB9582.812.9.1::pDAB8264.44.06.1 which resulted from the expression of the cry1Ac and cry1F transgenes. Soybean event pDAB9582.812.9.1::pDAB8264.44.06.1 was tested against lab reared soybean pests including *Anticarsia gemmatalis* (velvetbean caterpillar) and *Pseudoplusia includens* (soybean looper). The breeding stack of soybean event pDAB9582.812.9.1::pDAB8264.44.06.1 was compared against the parental soybean events (soybean event pDAB9582.812.9.1 and soybean event pDAB8264.44.06.1) in addition to the non-transformed soybean variety Maverick. This comparison was made to determine whether the level of plant protection provided by the Cry1F and Cry1Ac proteins would be present in the breeding stack which introduced additional transgenes into the genome of the soybean plant. In addition, the breeding stack of soybean event pDAB9582.812.9.1::pDAB8264.44.06.1 and soybean event pDAB8264.44.06.1 were both sprayed with a single herbicide application containing 2,4-D and glyphosate (840 g ae/ha) prior to the insect bioassay to determine whether the spraying of the herbicides had any effect on the plant protection from insects provided by the Cry1F and Cry1Ac proteins.

Greenhouse trials were conducted on approximately three week old plants. Ten plants each were used to evaluate the breeding stack of soybean event pDAB9582.812.9.1::pDAB8264.44.06.1, soybean event pDAB9582.812.9.1, and the negative controls; herbicide sprayed soybean event pDAB8264.44.06.1 and Maverick. For each insect species tested (*Anticarsia gemmatalis* and *Chrysodeixis* (formerly *Pseudoplusia*) *includens*), 3 leaf punches were made from each plant for a total of 30 leaf discs/plant/insect species. The 1.4 cm diameter (or 1.54 cm$^2$) leaf punches were placed in a test arena on top of 2% water agar, infested with one neonate larvae and sealed with a perforated plastic lid. Mortality and leaf consumption were rated four days after infestation. Larvae that were not responsive to gentle probing were considered dead. Leaf damage was assessed by visually scoring the percentage of leaf punch consumed by the insect. Statistical analysis was performed on the data using JMP® Pro 9.0.1 (2010 SAS Institute Inc., Cary, N.C.).

The results (Table 13) obtained from these replicated experiments indicated that the level of insect protection and mortality provided by the Cry1F and Cry1Ac proteins of the breeding stack of soybean event pDAB9582.812.9.1::pDAB8264.44.06.1 were consistent with the parental soybean event pDAB9582.812.9.1. As expected, soybean event pDAB9582.812.9.1::pDAB8264.44.06.1 sustained significantly lower insect damage (0.10-0.15%) than soybean event pDAB8264.44.06.1 (58-76%) and the Maverick (79-91%) control plants for all insects tested. Additionally, high insect mortality (100%) was recorded for all soybean events which contained the cry1F and cry1Ac coding sequences, while the negative controls, Maverick and soybean event pDAB8264.44.06.1 resulted in <10% insect mortality. Thus, the soybean event pDAB9582.812.9.1::pDAB8264.44.06.1 provided protection from insecticidal activity at levels comparable to the parental soybean event pDAB9582.812.9.1.

TABLE 13

Shows the mean percent leaf damage and mortality of
*Pseudoplusia includens* (SBL) and *Anticarsia gemmatalis*
(VBC) fed on various soybean events. (n = 24)

| Soybean events | Insects | Mean % leaf damage | Mean % mortality |
|---|---|---|---|
| Maverick | SBL | 91.46 | 4.2 |
|  | VBC | 78.96 | 0 |
| pDAB8264.44.06.1 | SBL | 75.83 | 0 |
|  | VBC | 58.33 | 8.3 |
| pDAB9582.812.9.1 | SBL | 0.10 | 100 |
|  | VBC | 0.15 | 100 |
| pDAB9582.812.9.1 × pDAB8264.44.06.1 | SBL | 0.10 | 100 |
|  | VBC | 0.10 | 100 |

Example 9: Breeding Stack of Soybean Event pDAB8264.44.06.1 and Soybean Insect Tolerant Event pDAB9582.814.19.1

Example 9.1: Sexual Crossing of Soybean Event pDAB8264.44.06.1 and Soybean Insect Tolerant Event pDAB9582.814.19.1

Soybean event pDAB8264.44.06.1 was sexually crossed with soybean event pDAB9582.814.19.1. The anthers of soybean event pDAB8264.44.06.1 were manually rubbed across the stigma of soybean event pDAB9582.814.19.1, thereby fertilizing soybean event pDAB9582.814.19.1. The resulting F1 progeny which contained integration events from both soybean event pDAB9582.814.19.1 and soybean event pDAB8264.44.06.1 were screened for tolerance to 2,4-D and glyphosate herbicides to identify progeny plants which contained both integration events. Next, the F1 progeny plants were self-fertilized to produce an F2 offspring which was confirmed to segregate independently for both events. The F2 plants were sprayed with a single herbicide application containing both 2,4-D (840 g ae/ha) and glyphosate (840 g ae/ha). The resulting F2 plants were screened using a Taqman zygosity based assay to identify plants that were homozygous for both events. Selfing of these F2 homozygous plants produced an F3 offspring that were homozygous for both soybean event pDAB9582.814.19.1 and soybean event pDAB8264.44.06.1. The resulting event was labeled as soybean event pDAB9582.814.19.1::pDAB8264.44.06.1.

Example 9.2: Determination of the Zygosity Status of Soybean Event pDAB9582.814.19.1::pDAB8264.44.06.1

To determine the zygosity status of plants produced from the breeding cross of soybean event pDAB8264.44.06.1 and soybean event pDAB9582.814.19.1, separate event specific TAQMAN® assays were developed to detect the presence of either the pDAB9582.814.19.1 or pDAB8264.44.06.1 integration events. Segregating F2 plants, produced from the self fertilization of a breeding cross of soybean event pDAB9582.814.19.1 and soybean event pDAB8264.44.06.1, were tested with these event specific TAQMAN® assays to identify individual plants which contained both soybean event pDAB9582.814.19.1 and soybean event pDAB8264.44.06.1, and were homozygous for both events.

gDNA Isolation gDNA samples from segregating F2 plants of the breeding stack of soybean event pDAB9582.814.19.1::pDAB8264.44.06.1 were tested in this study. Fresh soybean leaf discs, 4 per plant, were collected from 37 segregating F2 plants of the breeding stack of soybean event pDAB9582.814.19.1::pDAB8264.44.06.1. Genomic DNA was extracted from these samples using a modified Qiagen MagAttract Plant DNA Kit® (Qiagen, Valencia, Calif.).

TAQMAN® Assay and Results

TAQMAN® primers and probes as previously described were designed for the use of individual event specific assays for soybean events pDAB9582.814.19.1 (U.S. Provisional Application No. 61/471,845) and pDAB8264.44.06.1 (described above). These reagents were used with the conditions listed below to determine the zygosity of each integration event contained within the breeding stack of soybean event pDAB9582.814.19.1::pDAB8264.44.06.1.

The multiplex PCR conditions for amplification are as follows: 1× Roche PCR Buffer, 0.4 µM event pDAB8264.44.06.1 specific forward primer, 0.4 µM event pDAB8264.44.06.1 specific reverse primer 0.4 µM event pDAB9582.814.19.1 specific forward primer, 0.4 µM event pDAB9582.814.19.1 specific reverse primer, 0.4 µM Primer GMS116 F, 0.4 µM Primer GMS116 R, 0.2 µM Event pDAB9582.814.19.1 specific probe, 0.2 µM Event pDAB8264.44.06.1 specific probe, 0.2 µM GMS116 Probe, 0.1% PVP, 20 ng gDNA in a total reaction of 10 µl. The cocktail was amplified using the following conditions: i) 95° C. for 10 min., ii) 95° C. for 10 sec, iii) 60° C. for 30 sec, iv) 72° C. for 1 sec v) repeat step ii-iv for 35 cycles, v) 40° C. hold. The Real time PCR was carried out on the Roche LightCycler® 480. Data analysis was based on measurement of the crossing point (Cp value) determined by LightCycler® 480 software, which is the PCR cycle number when the rate of change in fluorescence reaches its maximum.

A total of 37 segregating F2 plants, produced from the breeding cross of soybean event pDAB9582.814.19.1 and soybean event pDAB8264.44.06.1 were tested with the event specific TAQMAN® assays to determine the zygosity of individual plants for both soybean event pDAB9582.814.19.1 and soybean event pDAB8264.44.06.1. The results from these assays indicated that soybean event pDAB9582.814.19.1 and soybean event pDAB8264.44.06.1 were both present and detected in 23 plants. The zygosity status (also described as ploidy level) of each integration event is indicated in Table 14. Of the 23 identified plants, 1 plant was identified which contained two copies of soybean event pDAB9582.814.19.1 and soybean event pDAB8264.44.06.1.

TABLE 14

Event specific TAQMAN ® zygosity analysis
of the breeding stack of soybean event
pDAB9582.814.19.1::pDAB8264.44.06.1

| Zygosity status for pDAB9582.814.19.1::pDAB8264.44.06.1 | Number of plants |
|---|---|
| Homozygous::Homozygous | 1 |
| Homozygous::Hemizygous | 7 |
| Homozygous::Null | 1 |
| Hemizygous::Homozygous | 3 |
| Hemizygous::Hemizygous | 12 |
| Hemizygous::Null | 5 |
| Null::Homozygous | 0 |
| Null::Hemizygous | 2 |
| Null::Null | 6 |

Example 9.3: Characterization of Protein Expression in the Breeding Stack of Soybean Event pDAB9582.814.19.1::pDAB8264.44.06.1

The biochemical properties of the recombinant Cry1F, Cry1Ac, AAD12, 2mEPSPS, and PAT proteins expressed in the breeding stack of soybean event pDAB9582.814.19.1::pDAB8264.44.06.1 were characterized. An Enzyme Linked Immunosorbent Assay (ELISA) was used to quantify the expression of PAT. Comparatively, Cry1Ac/Cry1F and AAD12/2mEPSPS proteins were quantified by multiplexed immunoassays utilizing electrochemiluminescent technology from Meso-Scale Discovery (MSD, Gaithersburg, Md.). Collectively, these assays were used to characterize the biochemical properties and confirm the robust expression of these proteins in the breeding stack of soybean event pDAB9582.814.19.1::pDAB8264.44.06.1.

Expression of the PAT Protein in Plant Tissues

Levels of PAT protein were determined in the breeding stack of F3 soybean event pDAB9582.814.19.1::pDAB8264.44.06.1 which were identified to be homozygous for both event pDAB9582.814.19.1 and event pDAB8264.44.06.1 integrations. The levels of PAT protein expressed from soybean event pDAB9582.814.19.1::pDAB8264.44.06.1 was compared to the parental events, soybean event pDAB9582.814.19.1 and soybean event pDAB8264.44.06.1.

The soluble, extractable PAT protein was obtained from soybean leaf tissue and measured using a quantitative ELISA method (APS 014, Envirologix, Portland, Me.). Samples of soybean leaf tissues were isolated from greenhouse grown test plants at the unifoliate to V1 stage and prepared for expression analysis. The PAT protein was extracted from soybean plant tissues with a phosphate buffered saline solution containing the detergent Tween-20 (PBST) and 1% polyvinylpyrrolidone 40 (PVP-40). The samples were then extracted using a GenoGrinder® at 1500 rpm for 5 minutes. The plant extract was centrifuged; the aqueous supernatant was collected, diluted with appropriate buffer as necessary, and analyzed using the PAT ELISA kit in a sandwich format. The kit was used following the manufacturer's suggested protocol (Envirologix, Portland, Me.).

Detection analysis was performed to investigate the expression and heritability of soybean event pDAB9582.814.19.1::pDAB8264.44.06.1. The F3 generation of the breeding stack, soybean event pDAB9582.814.19.1::pDAB8264.44.06.1 expressed PAT at higher concentrations than either the parental events, pDAB9582.814.19.1 and pDAB8264.44.06.1. The increased concentration of PAT in soybean event pDAB9582.814.19.1::pDAB8264.44.06.1 breeding stack was expected. The higher concentrations of PAT are a result of soybean event pDAB9582.814.19.1::pDAB8264.44.06.1 containing twice as many copies of the pat coding sequence as compared to either of the parental events (Table 15).

TABLE 15

Average PAT protein expression from soybean event pDAB9582.814.19.1::pDAB8264.44.06.1, and parental events (soybean event pDAB9582.814.19.1 and soybean event pDAB8264.44.06.1).

| Soybean Event | Average PAT Expression (ng/cm$^2$) |
|---|---|
| pDAB9582.814.19.1::pDAB8264.44.06.1 | 20.1 |
| pDAB9582.814.19.1 | 12.0 |
| pDAB8264.44.06.1 | 13.3 |

Expression of the Cry1F and Cry1Ac Proteins in Plant Tissues

Levels of Cry1F and Cry1Ac protein were determined in the breeding stack of F3 soybean event pDAB9582.814.19.1::pDAB8264.44.06.1 which were identified to be homozygous for both event pDAB9582.814.19.1 and event pDAB8264.44.06.1 integrations. The levels of Cry1F and Cry1Ac protein expressed from soybean event pDAB9582.814.19.1::pDAB8264.44.06.1 was compared to the parental event, soybean event pDAB9582.814.19.1.

The soluble, extractable Cry1F and Cry1Ac protein was obtained from soybean leaf tissue and measured using a multiplexed electrochemiluminescent MSD assay. Samples of soybean leaf tissue were isolated from greenhouse grown plants at the unifoliate to V1 stage and prepared for expression analysis. The Cry1F and Cry1Ac protein was extracted from soybean plant tissues with a phosphate buffered saline solution containing the detergent Tween-20 (PBST) and 1% polyvinylpyrrolidone 40 (PVP-40). The samples were then extracted using a GenoGrinder® at 1500 rpm for 5 minutes. The plant extract was centrifuged; the aqueous supernatant was collected, diluted with appropriate buffer as necessary, and analyzed using a Cry1F/Cry1Ac multiplex MSD assay from Meso-Scale Discovery. The kit was used following the manufacturer's suggested protocol.

Detection analysis was performed to investigate the expression and heritability of soybean event pDAB9582.814.19.1::pDAB8264.44.06.1. The F3 generation of the breeding stack of soybean event pDAB9582.814.19.1::pDAB8264.44.06.1 expressed Cry1Ac protein at concentrations higher than the parental soybean event pDAB9582.814.19.1. The F3 generation of the breeding stack of soybean event pDAB9582.814.19.1::pDAB8264.44.06.1 expressed Cry1F protein at concentrations lower than the parental soybean event pDAB9582.814.19.1. (Table 16). Despite the variability in expression levels, these results indicate that soybean event pDAB9582.814.19.1::pDAB8264.44.06.1 plants contained a functionally expressing copy of the cry1F and cry1Ac coding sequences which were inherited from the parental line, soybean event pDAB9582.814.19.1.

TABLE 16

Average Cry1Ac and Cry1F protein expression from soybean event pDAB9582.814.19.1::pDAB8264.44.06.1 as compared to parental event pDAB9582.814.19.1

| Soybean Event | Average Cry1Ac Expression (ng/cm$^2$) | Average Cry1F Expression (ng/cm$^2$) |
|---|---|---|
| pDAB9582.814.19.1::pDAB8264.44.06.1 | 25.3 | 55.7 |
| pDAB9582.814.19.1 | 22.4 | 106.7 |

Expression of the AAD12 and 2mEPSPS Proteins in Plant Tissues

Levels of AAD12 and 2mEPSPS protein were determined in the breeding stack of F3 soybean event pDAB9582.814.19.1::pDAB8264.44.06.1 which were identified to be homozygous for both event pDAB9582.814.19.1 and event pDAB8264.44.06.1 integrations. The levels of AAD12 and 2mEPSPS protein expressed from soybean event pDAB9582.814.19.1::pDAB8264.44.06.1 was compared to the parental event, Soybean Event pDAB8264.44.06.1.

The soluble, extractable AAD12 and 2mEPSPS protein was obtained from soybean leaf tissue and measured using a multiplexed electrochemiluminescent MSD assay. Samples of soybean leaf tissue were isolated from greenhouse grown plants at the unifoliate to V1 stage and prepared for expression analysis. The AAD12 and 2mEPSPS protein was extracted from soybean plant tissues with a phosphate buffered saline solution containing the detergent Tween-20 (PBST) and 1% polyvinylpyrrolidone 40 (PVP-40). The samples were then extracted using a GenoGrinder® at 1500 rpm for 5 minutes. The plant extract was centrifuged; the aqueous supernatant was collected, diluted with appropriate buffer as necessary, and analyzed using a AAD12 and 2mEPSPS multiplex MSD assay from Meso-Scale Discovery. The kit was used following the manufacturer's suggested protocol.

Detection analysis was performed to investigate the expression and heritability of soybean event pDAB9582.814.19.1::pDAB8264.44.06.1. The F3 generation of the breeding stack of soybean event pDAB9582.814.19.1::pDAB8264.44.06.1 expressed AAD12 and 2mEPSPS proteins at concentrations lower than the parental soybean event pDAB8264.44.06.1. (Table 17). Despite the variability in expression levels, these results indicated that soybean event pDAB9582.814.19.1::pDAB8264.44.06.1 plants contained a functionally expressing copy of the aad-12 and 2mEPSPS coding sequences which were inherited from the parental line, soybean event pDAB8264.44.06.1.

TABLE 17

Average AAD12 and 2mEPSPS protein expression from soybean event pDAB9582.814.19.1::pDAB8264.44.06.1 as compared to parental soybean event pDAB8264.44.06.1

| Soybean Event | Average AAD12 Expression (ng/cm$^2$) | Average 2mEPSPS Expression (ng/cm$^2$) |
|---|---|---|
| pDAB9582.814.19.1::pDAB8264.44.06.1 | 261.3 | 127.9 |
| pDAB8264.44.06.1 | 320.4 | 328.9 |

Example 9.4: Herbicide Tolerance of the Breeding Stack of Soybean Event pDAB9582.814.19.1::pDAB8264.44.06.1

Herbicide tolerance of the breeding stack, soybean event pDAB9582.814.19.1::pDAB8264.44.06.1 was assayed. Soybean event pDAB9582.814.19.1::pDAB8264.44.06.1 seed were planted in a greenhouse study and mature plants were sprayed with a single herbicide application which consisted of a combination of 2,4-D and glyphosate. The resulting tolerance to these herbicides was measured by counting the number of surviving plants. Comparatively, control plants which did not contain the aad-12 and 2mEPSPS genes and were expected to be susceptible to the application of the 2,4-D and glyphosate herbicides were included in the study.

Herbicide tolerance was assessed in greenhouse grown F2 plants of soybean event pDAB9582.814.19.1::pDAB8264.44.06.1. The soybean plants were grown in 4 inch pots which contained one plant per pot. A total of 37, F3 homozygous plants were sprayed with a single application of 2,4-D and glyphosate (840 ae/ha) at the unifoliate growth stage. All 25 plants survived after being sprayed with the herbicides, indicating that the soybean event pDAB9582.814.19.1::pDAB8264.44.06.1 plants were tolerant to the application of the herbicides, glyphosate and 2,4-D.

In summary, the aad-12 and 2mEPSPS genes which were present in the soybean event pDAB8264.44.06.1 parental line conferred tolerance to 2,4-D and glyphosate herbicides. These traits were passed and inherited in soybean event pDAB9582.814.19.1::pDAB8264.44.06.1, thereby providing herbicidal tolerance to soybean event pDAB9582.814.19.1::pDAB8264.44.06.1. The soybean event pDAB9582.812.9.1::pDAB8264.44.06.1 plants which were susceptible to the herbicide application did not contain copies of the aad-12 and 2mEPSPS as a result of Mendelian segregation of the pDAB8264.44.06.1 integration event. Additionally, control plants which did not contain the aad-12 and 2mEPSPS genes were susceptible to the application of the 2,4-D and glyphosate herbicides.

Example 9.5: Characterization of Insecticidal Activity of Soybean Event pDAB9582.814.19.1::pDAB8264.44.06.1

Greenhouse evaluations were conducted to characterize the insecticidal tolerance activity of soybean event pDAB9582.814.19.1::pDAB8264.44.06.1 which resulted from the expression of the Cry1Ac and Cry1F transgenes. Soybean event pDAB9582.814.19.1::pDAB8264.44.06.1 was tested against lab reared soybean pests including *Anticarsia gemmatalis* (velvetbean caterpillar) and *Pseudoplusia includens* (soybean looper). The breeding stack of soybean event pDAB9582.814.19.1::pDAB8264.44.06.1 was compared against the parental soybean events (soybean event pDAB9582.814.19.1 and soybean event pDAB8264.44.06.1) in addition to the non-transformed soybean variety Maverick. This comparison was made to determine whether the level of plant protection to insect damage provided by the Cry1F and Cry1Ac proteins would be present in the breeding stack which introduced additional transgenes into the genome of the soybean plant. In addition, the breeding stack of soybean event pDAB9582.814.19.1::pDAB8264.44.06.1 and soybean event pDAB8264.44.06.1 were both sprayed with a single herbicide application containing 2,4-D and glyphosate (840 g ae/ha) prior to the insect bioassay to determine whether the spraying of the herbicides had any effect on the plant protection from insects provided by the Cry1F and Cry1Ac proteins.

Greenhouse trials were conducted on approximately three week old plants. Ten plants each were used to evaluate the breeding stack of soybean event pDAB9582.814.19.1::pDAB8264.44.06.1, soybean event pDAB9582.814.19.1, and the negative controls; herbicide sprayed soybean event pDAB8264.44.06.1 and Maverick. For each insect species tested (*Anticarsia gemmatalis* and *Pseudoplusia includens*), 3 leaf punches were made from each plant for a total of 30 leaf discs/plant/insect species. The 1.4 cm diameter (or 1.54 cm$^2$) leaf punches were placed in a test arena on top of 2% water agar, infested with one neonate larvae and sealed with a perforated plastic lid. Mortality and leaf consumption were rated 4 days after infestation. Larvae that were not responsive to gentle probing were considered dead. Leaf damage was assessed by visually scoring the percentage of leaf punch consumed by the insect. Statistical analysis was performed on the data using JMP® Pro 9.0.1 (2010 SAS Institute Inc., Cary, N.C.).

The results (Table 18) obtained from these replicated experiments indicated that the level of insect damage and mortality provided by the Cry1F and Cry1Ac proteins of the breeding stack of soybean event pDAB9582.814.19.1::pDAB8264.44.06.1 were consistent with the parental soybean event pDAB9582.814.19.1. As expected soybean event pDAB9582.814.19.1::pDAB8264.44.06.1 sustained significantly lower insect damage (0.10-0.12%) than soybean event pDAB8264.44.06.1 (58-76%) and the Maverick (79-91%) control plants for all insects tested. Additionally, high insect mortality (100%) was recorded for all soybean events which contained the cry1F and cry1Ac coding sequences, while the negative controls, maverick and soybean event pDAB8264.44.06.1, resulted in <10% insect mortality.

Thus, the soybean event pDAB9582.814.19.1::pDAB8264.44.06.1 provided protection from insecticidal activity at levels comparable to the parental soybean event pDAB9582.814.19.1.

TABLE 18

Shows the mean percent leaf damage and mortality of *Pseudoplusia includens* (SBL) and *Anticarsia gemmatalis* (VBC) fed on various soybean events. (n = 24)

| Soybean events | Insects | Mean % leaf damage | Mean % mortality |
|---|---|---|---|
| Maverick | SBL | 91.46 | 4.2 |
|  | VBC | 78.96 | 0 |
| pDAB8264.44.06.1 | SBL | 75.83 | 0 |
|  | VBC | 58.33 | 8.3 |
| pDAB9582.814.19.1 | SBL | 0.12 | 100 |
|  | VBC | 0.10 | 100 |
| pDAB9582.814.19.1::pDAB8264.44.06.1 | SBL | 0.10 | 100 |
|  | VBC | 0.10 | 100 |

The invention claimed is:

1. A method of breeding a soybean plant, said method comprising crossing a first soybean plant comprising SEQ ID NO:27 with a second soybean plant to produce a third soybean plant having a genome comprising SEQ ID NO:27.

2. The method of claim 1, further comprising assaying said third soybean plant for the presence of SEQ ID NO:27 in said genome.

3. The method of claim 1, wherein said method is used to introgress a herbicide tolerance trait into the third soybean plant.

* * * * *